US008771755B2

(12) United States Patent
Gojon-Romanillos et al.

(10) Patent No.: US 8,771,755 B2
(45) Date of Patent: Jul. 8, 2014

(54) PREPARATION AND COMPOSITIONS OF HIGHLY BIOAVAILABLE ZEROVALENT SULFUR AND USES THEREOF

(75) Inventors: Gabriel Gojon-Romanillos, San Pedro Garza García (MX); Gabriel Gojon-Zorrilla, San Pedro Garza García (MX)

(73) Assignee: Nuevas Alternativas Naturales, S.A.P.I. de C.V., Monterrey (MX)

( * ) Notice: Subject to any disclaimer, the term of this patent is extended or adjusted under 35 U.S.C. 154(b) by 0 days.

(21) Appl. No.: 13/614,820

(22) Filed: Sep. 13, 2012

(65) Prior Publication Data
US 2013/0064904 A1 Mar. 14, 2013

Related U.S. Application Data

(60) Provisional application No. 61/534,585, filed on Sep. 14, 2011.

(51) Int. Cl.
| A61K 33/04 | (2006.01) |
| A61P 9/00 | (2006.01) |
| A61P 25/28 | (2006.01) |
| A61P 29/00 | (2006.01) |

(52) U.S. Cl.
USPC .......................................... 424/705; 424/703

(58) Field of Classification Search
USPC ................................................ 424/703, 705
See application file for complete search history.

(56) References Cited

U.S. PATENT DOCUMENTS

| 5,100,653 | A | 3/1992 | Campo |
| 7,741,359 | B2 | 6/2010 | Wallace et al. |
| 8,361,514 | B2 | 1/2013 | Gojon-Romanillos |
| 8,389,005 | B2 | 3/2013 | Gojon-Romanillos |
| 2002/0132015 | A1 | 9/2002 | Shacknai et al. |
| 2003/0235571 | A1 | 12/2003 | Gojon-Romanillos |
| 2004/0057972 | A2 | 3/2004 | Shacknai et al. |
| 2008/0199541 | A1 | 8/2008 | Tomaselli et al. |
| 2009/0181081 | A1 | 7/2009 | Gojon-Romanillos |
| 2009/0304819 | A1 | 12/2009 | Gojon-Romanillos |
| 2011/0195945 | A1 | 8/2011 | Ruan et al. |
| 2012/0135091 | A1 | 5/2012 | Roth et al. |

FOREIGN PATENT DOCUMENTS

| EP | 0242553 A1 | 10/1987 |
| RU | 2406477 C1 | 12/2010 |
| WO | WO-2009004082 A2 | 1/2009 |
| WO | WO-2010029021 A1 | 3/2010 |
| WO | WO-2012075242 A2 | 6/2012 |

OTHER PUBLICATIONS

International Search Report and Written Opinion for International Application No. PCT/US12/55205, mailed Nov. 20, 2012.
International Search Report and Written Opinion for International Application No. PCT/MX12/00086, mailed Mar. 27, 2013.
Abdolrasulnia et al., "Transfer of persulfide sulfur from thiocystine to rhodanese," *Biochim. Biophys. Acta.* 567:135-143, 1979 (Abstract only).
Abe et al., "The Possible Role of Hydrogen Sulfide as an Endogenous Neuromodulator," *The Journal of Neuroscience* 16:1066-1071, 1996.
Agarwal et al., "Clinical Relevance of Oxidative Stress in Male Factor Infertility: An Update," *American Journal of Reproductive Immunology* 59:2-11, 2008.
Agarwal et al., "Oxidative stress and antioxidants for idiopathic oligoasthenoteratospermia: Is it justified?," *Indian J. Urol.* 27:74-85, 2011 (Abstract only).
Agarwal et al., "Oxidative stress and antioxidants in male infertility: a difficult balance," *Iranian Journal of Reproductive Medicine* 3:1-8, 2005.
Agarwal et al., "Role of Oxidative Stress in the Pathophysiological Mechanism of Erectile Dysfunction," *Journal of Andrology* 27:335-347, 2006.
Aggarwal, "Nuclear factor-κB:The enemy within," *Cancer Cell* 6:203-208, 2004.
Aggarwal et al., "Inflammation and Cancer: How Friendly is the Relationship for Cancer Patients?," *Curr. Opin. Pharmacol.* 9:351-369, 2009.
Aggarwal et al., "Signal Transducer and Activator of Transcription-3, Inflammation, and Cancer: How Intimate Is the Relationship?," *Ann. N.Y. Acad. Sci.* 1171:59-76, 2009.
Aggarwal et al., "Targeting Inflammatory Pathways for Prevention and Therapy of Cancer: Short-Term Friend, Long-Term Foe," *Clin. Cancer Res.* 15:425-430, 2009.
Aitken et al., "New insights into sperm physiology and pathology," *Handb. Exp. Pharmacol.* 198:99-115, 2010 (Abstract only).
Aitken et al., "Redox regulation of human sperm function: from the physiological control of sperm capacitation to the etiology of infertility and DNA damage in the germ line," *Antioxid. Redox Signal.* 14:367-381, 2011 (Abstract only).
Aleksunes et al., "Transcriptional Regulation of Renal Cytoprotective Genes by Nrf2 and Its Potential Use as a Therapeutic Target to Mitigate Cisplatin-Induced Nephrotoxicity," *J. Pharmacol. Exp. Ther.* 335:2-12, 2010.
Anderson et al., "The effects of focal ischemia and reperfusion on the glutathione content of mitochondria from rat brain subregions," *J. Neurochem.* 81:541-549, 2002.
Anoush et al., "The Protective Effect of Garlic Extract against Acetaminophen-Induced Loss of Mitochondrial Membrane Potential in Freshly Isolated Rat Hepatocytes," *Iranian Journal of Pharmaceutical Sciences* 5:141-150, 2009.
Antosiewicz et al., "c-Jun NH2-Terminal Kinase Signaling Axis Regulates Diallyl Trisulfide-Induced Generation of Reactive Oxygen Species and Cell Cycle Arrest in Human Prostate Cancer Cells," *Cancer Res.* 66:5379-5386, 2006.
Aruoma et al., "The antioxidant action of taurine, hypotaurine and their metabolic precursors," *Biochem. J.* 256:251-255, 1988.

(Continued)

*Primary Examiner* — Frederick Krass
*Assistant Examiner* — Tracy Liu
(74) *Attorney, Agent, or Firm* — Clark & Elbing LLP

(57) ABSTRACT

The present invention features sulfur-rich compositions and preparations thereof that are safe and effective as hydrogen sulfide prodrugs of high bioavailability. The invention also includes methods of treating pathological conditions associated with oxidative stress using sulfur-rich compositions. The invention further includes sulfur-rich compositions as antidotes and medical food for preserving and promoting general health.

4 Claims, 27 Drawing Sheets

(56) References Cited

OTHER PUBLICATIONS

Asano et al., "Aging influences multiple indices of oxidative stress in the heart of the Fischer 344/NNia x Brown Norway/BiNia rat," Redox. Rep. 12:167-180, 2007 (Abstract only).
Badaloo et al., "Cysteine supplementation improves the erythrocyte glutathione synthesis rate in children with severe edematous malnutrition," Am. J. Clin. Nutr. 76:646-652, 2002.
Bagnato et al., "Clinical improvement and serum amino acid levels after mud-bath therapy," Int. J. Clin. Pharmacol. Res. 24:39-47, 2004 (Abstract only).
Balaban et al., "Delivery of the bioactive gas hydrogen sulfide during cold preservation of rat liver: effects on hepatic function in an ex vivo model," Artif. Organs 35:508-515, 2011 (Abstract only).
Ballatori et al., "Glutathione dysregulation and the etiology and progression of human diseases," Biol. Chem. 390:191-214, 2009.
Balogh et al., "Effectiveness of balneotherapy in chronic low back pain—a randomized single-blind controlled follow-up study," Forsch Komplementarmed Klass Naturheilkd 12:196-201, 2005 (Abstract only).
Ban et al., "Inhibition of Cell Growth and Induction of Apoptosis via Inactivation of NF-κB by a Sulfurcompound Isolated From Garlic in Human Colon Cancer Cells," J. Pharmacol. Sci. 104:374-383, 2007.
Bansal et al., "Impacts of Oxidative Stress and Antioxidants on Semen Functions," Vet. Med. Int. 2011:1-7, 2011.
Baskar et al., "Hydrogen sulfide gas has cell growth regulatory role," European Journal of Pharmacology 656:5-9, 2011.
Baskar et al., "Hydrogen sulfide-induces DNA damage and changes in apoptotic gene expression in human lung fibroblast cells," The FASEB Journal 21:247-255, 2007.
Baskin et al., "In vitro and in vivo comparison of sulfur donors as antidotes to acute cyanide intoxication," J. Appl. Toxicol. 19:173-183, 1999 (Abstract only).
Bass et al., "Novel Dithiolethione-Modified Nonsteroidal Anti-Inflammatory Drugs in Human Hepatoma HepG2 and Colon LS180 Cells," Clin. Cancer Res. 15:1964-1972, 2009.
Baumber et al., "Reactive Oxygen Species and Cryopreservation Promote DNA Fragmentation in Equine Spermatozoa," J. Androl. 24:621-628, 2003.
Beck-Speier et al., "Sulfite stimulates NADPH oxidase of human neutrophils to produce active oxygen radicals via protein kinase C and Ca2+/calmodulin pathways," Free Radic. Biol. Med. 14:661-668, 1993 (Abstract only).
Becker et al., "Thioredoxin reductase as a pathophysiological factor and drug target," Eur. J. Biochem. 267:6118-6125, 2000.
Beinert, "A tribute to sulfur," Eur. J. Biochem. 267:5657-5664, 2000.
Benavides et al., "Hydrogen sulfide mediates the vasoactivity of garlic," PNAS 104:17977-17982, 2007.
Bender et al., "Hydrotherapy, balneotherapy, and spa treatment in pain management," Rheumatol Int. 25:220-224, 2005.
Benedetti et al., "Antioxidative effects of sulfurous mineral water: protection against lipid and protein oxidation," Eur. J. Clin. Nutr. 63:106-112, 2007 (Abstract only).
Benedetti et al., "Biomarkers of oxidation, inflammation and cartilage degradation in osteoarthritis patients undergoing sulfur-based spa therapies," Clin. Biochem. 43:973-978, 2010 (Abstract only).
Bheemreddy et al., "The Metabolic Fate of Purified Glucoraphanin in F344 Rats," J. Agric. Food Chem. 55:2861-2866, 2007.
Biermann et al., "Inhalative preconditioning with hydrogen sulfide attenuated apoptosis after retinal ischemia/reperfusion injury," Molecular Vision 17:1275-1286, 2011.
Bivalacqua et al., "Superoxide anion production in the rat penis impairs erectile function in diabetes: influence of in vivo extracellular superoxide dismutase gene therapy," J. Sex. Med. 2:187-197, 2005 (Abstract only).
Blackstone et al., "H2S induces a suspended animation-like state in mice," Science 308:518, 2005 (Abstract only).
Blackstone et al., "Suspended animation-like state protects mice from lethal hypoxia," Shock. 27:370-372, 2007 (Abstract only).
Blanco et al., "Diurnal variation in glutathione and cysteine redox states in human plasma," Am. J. Clin. Nutr. 86:1016-1023, 2007.
Blouet et al., "Dietary cysteine alleviates sucrose-induced oxidative stress and insulin resistance," Free Radic. Biol. Med. 42:1089-1097, 2007 (Abstract only).
Blumentals et al., "Role of Polysulfides in Reduction of Elemental Sulfur by the Hyperthermophilic Archaebacterium *Pyrococcus furiosus*," Applied and Environmental Microbiology 56:1255-1262, 1990.
Bordo et al., "The rhodanese/Cdc25 phosphatase superfamily: Sequence-structure-function relations," EMBO Reports 3:741-746, 2002.
Bos et al., "Hydrogen Sulfide-Induced Hypometabolism Prevents Renal Ischemia/Reperfusion Injury," J. Am. Soc. Nephrol. 20:1901-1905, 2009.
Bouckenooghe et al., "Is taurine a functional nutrient?," Curr. Opin. Clin. Nutr. Metab. Care. 9:728-733, 2006 (Abstract only).
Bouma et al., "Induction of torpor: mimicking natural metabolic suppression for biomedical applications," J. Cell. Physiol. 227:1285-1290, 2012 (Abstract only).
Braga et al., "Antioxidant Effect of Sulphurous Thermal Water on Human Neutrophil Bursts: Chemiluminescence Evaluation," Respiration 75:193-201, 2008.
Brancaleone et al., "Biosynthesis of H2S is impaired in non-obese diabetic (NOD) mice," British Journal of Pharmacology 155:673-680, 2008.
Branzoli et al., "Evidence for an Active Site Persulfide Residue in Rabbit Liver Aldehyde Oxidase," The Journal of Biological Chemistry 249:4346-4349, 1974.
Breitkreutz et al., "Improvement of immune functions in HIV infection by sulfur supplementation: two randomized trials," J. Mol. Med. (Berl). 78:55-62, 2000 (Abstract only).
Brigelius-Flohé et al., "Basic Principles and Emerging Concepts in the Redox Control of Transcription Factors," Antioxidants & Redox Signaling 15:2335-2381, 2011.
Britschka et al., "The efficacy of Brazilian black mud treatment in chronic experimental arthritis," Rheumatol. Int. 28:39-45, 2007 (Abstract only).
Brosnan et al., "The Sulfur-Containing Amino Acids: An Overview," J. Nutr. 136:1636S-1640S, 2006.
Bruchhausen et al., "Thiol antioxidants block the activation of antigen-presenting cells by contact sensitizers," J. Invest. Dermatol. 121:1039-1044, 2003.
Bucci et al., "Hydrogen sulphide in heart and systemic circulation," Inflamm. Allergy Drug Targets 10:103-108, 2011 (Abstract only).
Budde et al., "Hydrogen Sulfide Increases Hypoxia-inducible Factor-1 Activity Independently of von Hippel-Lindau Tumor Suppressor-1 in *C. elegans*," Molecular Biology of the Cell 21:212-217, 2010.
Buhl et al., "Systemic glutathione deficiency in symptom-free HIV-seropositive individuals," Lancet. 2:1294-1298, 1989 (Abstract only).
Buskila et al., "Balneotherapy for fibromyalgia at the Dead Sea," Rheumatol. Int. 20:105-108, 2001 (Abstract only).
Bykov et al., "Magneto-peloidotherapy and hydrogen sulfide baths for the correction of dyslipidemia and immune inflammation in patients with ischemic heart disease during resort treatment," Vopr. Kurortol. Fizioter. Lech. Fiz. Kult. 4:17-19, 2009 (Abstract only).
Cai et al., "The novel proangiogenic effect of hydrogen sulfide is dependent on Akt phosphorylation," Cardiovascular Research 76:29-40, 2007.
Calabrese et al., "Labile Sulfur in Human Superoxide Dismutase," Eur. J. Biochem. 56:305-309, 1975.
Caliendo et al., "Synthesis and Biological Effects of Hydrogen Sulfide (H2S): Development of H2S-Releasing Drugs as Pharmaceuticals," J. Med. Chem. 53:6275-6286, 2010.
Calvert et al., "Genetic and Pharmacologic Hydrogen Sulfide Therapy Attenuates Ischemia-Induced Heart Failure in Mice," Circulation 122:11-19, 2010.
Calvert et al., "Hydrogen Sulfide Confers Cardioprotection in the Setting of Diabetes," J. Am. Coll. Cardiol. 55:A116.E1082, 2010 (Abstract only).
Calvert et al., "Hydrogen Sulfide Mediates Cardioprotection Through Nrf2 Signaling," Circulation Research 105:365-374, 2009.

(56) References Cited

OTHER PUBLICATIONS

Calvert et al., "Novel insights into hydrogen sulfide-mediated cytoprotection," *Antioxidants & Redox Signaling* 12:1203-1217, 2010.
Capps et al., "Thermochemistry of Sulfur Atom Transfer. Enthalpies of Reaction of Phosphines with Sulfur, Selenium, and Tellurium, and of Desulfurization of Triphenylarsenic Sulfide, Triphenylantimony Sulfide, and Benzyl Trisulfide," *Inorg. Chem.* 37:2861-2864, 1998.
Cassanelli et al., "Sulfide is an efficient iron releasing agent for mammalian ferritins," *Biochimica et Biophysica Acta* 1547:174-182, 2001.
Cavallini, "Male idiopathic oligoasthenoteratozoospermia," *Asian J. Androl.* 8:143-157, 2006.
Cavallini et al., "Interaction of Proteins with Sulfide," *Eur. J. Biochem.* 14:169-174, 1970.
Cha et al., "Glutathione-Linked Thiol Peroxidase Activity of Human Serum Albumin: A Possible Antioxidant Role of Serum Albumin in Blood Plasma," *Biochemical and Biophysical Research Communications* 222:619-625, 1996.
Chabory et al., "Mammalian glutathione peroxidases control acquisition and maintenance of spermatozoa integrity," *J. Anim. Sci.* 88:1321-1331, 2010.
Chan et al., "Redox Regulation of Angiogenesis: NADPH Oxidase as a Drug Target," *Anti-Angiogenesis Drug Discovery and Development* 1:86-115, 2011.
Chang et al., "Growth inhibitory effect of alk(en)yl thiosulfates derived from onion and garlic in human immortalized and tumor cell lines," *Cancer Lett.* 223:47-55, 2005 (Abstract only).
Chang et al., "Interaction of Methylglyoxal and Hydrogen Sulfide in Rat Vascular Smooth Muscle Cells," *Antioxidants & Redox Signaling* 12:1093-1100, 2010.
Chang et al., "Modulatory influence of sodium 2-propenyl thiosulfate from garlic on cyclooxygenase activity in canine platelets: possible mechanism for the anti-aggregatory effect," *Prostaglandins. Leukot. Essent. Fatty Acids.* 72:351-355, 2005 (Abstract only).
Chang et al., "Sodium 2-propenyl thiosulfate derived from garlic induces phase II detoxification enzymes in rat hepatoma H4IIE cells," *Nutr. Res.* 30:435-440, 2010 (Abstract only).
Chatterji et al., "Generation of reactive oxygen species by a persulfide (BnSSH)," *Bioorg. Med. Chem. Lett.* 15:3921-3924, 2005.
Chatterji et al., "Reaction of Thiols with 7-Methylbenzopentathiepin," *Bioorg. Med. Chem. Lett.* 13:1349-1352, 2003.
Chauncey et al., "The Catalytic Mechanism of Yeast Thiosulfate Reductase," *The Journal of Biological Chemistry* 258:15037-15045, 1983.
Chen et al., "Induction of detoxifying enzymes by garlic organosulfur compounds through transcription factor Nrf2: effect of chemical structure and stress signals," *Free Radic. Biol. Med.* 37:1578-1590, 2004 (Abstract only).
Chen et al., "Molecular Mechanisms of c-Jun N-terminal Kinase-mediated Apoptosis Induced by Anticarcinogenic Isothiocyanates," *The Journal of Biological Chemistry* 273:1769-1775, 1998.
Chen et al., "The Controlled Delivery of Hydrogen Sulfide for the Preservation of Heart Tissue," University of Maryland, 2011.
Chiku et al., "H2S Biogenesis by Human Cystathionine γ-Lyase Leads to the Novel Sulfur Metabolites Lanthionine and Homolanthionine and is Responsive to the Grade of Hyperhomocysteinemia," *Journal of Biological Chemistry* 284:11601-11612, 2009.
Chuah et al., "S-allylcysteine mediates cardioprotection in an acute myocardial infarction rat model via a hydrogen sulfide-mediated pathway," *Am. J. Physiol. Heart Circ. Physiol.* 293:H2693-H2701, 2007.
Cipollone et al., "Common Themes and Variations in the Rhodanese Superfamily," *IUBMB Life* 59:51-59, 2007.
Ciriolo et al., "Transduction of reducing power across the plasma membrane by reduced glutathione: A H-NMR spin-echo study of intact human erythrocytes," *Eur. J. Biochem.* 215:711-718, 1993.

Clark, "Sulfur and Hydrogen Sulfide Recovery," *Kirk-Othmer Encyclopedia of Chemical Technology*, John Wiley & Sons, Inc., 1-27, 2006.
Cocuzza et al., "Clinical Relevance of Oxidative Stress and Sperm Chromatin Damage in Male Infertility: An Evidence Based Analysis," *Int. Braz. J. Urol.* 33:603-621, 2007.
Collman et al., "Using a functional enzyme model to understand the chemistry behind hydrogen sulfide induced hibernation," *PNAS* 106:22090-22095, 2009.
Costantino, "The rhinogenic deafness and SPA therapy: clinical-experimental study," *Clin. Ter.* 159:311-315, 2008 (Abstract only).
Costantino et al., "Effectiveness of sulphur spa therapy with politzer in the treatment of rhinogenic deafness," *Acta Otorhinolaryngol Ital.* 26:7-13, 2006.
Costantino et al., "Possible antioxidant role of SPA therapy with chlorine-sulphur-bicarbonate mineral water," *Amino Acids* 36:161-165, 2009.
Cotgreave, "N-acetylcysteine: pharmacological considerations and experimental and clinical applications," *Adv. Pharmacol.* 38:205-227, 1997 (Abstract only).
Cvek et al., "Targeting of nuclear factor-kappaB and proteasome by dithiocarbamate complexes with metals," *Curr. Pharm. Des.* 13:3155-3167, 2007 (Abstract only).
Czesnikiewicz-Guzik et al., "NADPH oxidase and uncoupled nitric oxide synthase are major sources of reactive oxygen species in oral squamous cell carcinoma: potential implications for immune regulation under high oxidative stress conditions," *J. Physiol. Pharmacol.* 59:139-152, 2008.
Danson et al., "DT-diaphorase: a target for new anticancer drugs," *Cancer Treat. Rev.* 30:437-449, 2004 (Abstract only).
Das et al., "Garlic Compounds Generate Reactive Oxygen Species Leading to Activation of Stress Kinases and Cysteine Proteases for Apoptosis in Human Glioblastoma T98G and U87MG Cells," *Cancer* 110:1083-1095, 2007.
De Beus et al., "Modification of cysteine 111 in Cu/Zn superoxide dismutase results in altered spectroscopic and biophysical properties," *Protein Science* 13:1347-1355, 2004.
de la Asuncion et al., "Mitochondrial glutathione oxidation correlates with age-associated oxidative damage to mitochondrial DNA," *FASEB J.* 10:333-338, 1996.
Dello Russo et al., "Evidence that hydrogen sulphide can modulate hypothalamo-pituitary-adrenal axis function: in vitro and in vivo studies in the rat," *J. Neuroendocrinol.* 12:225-233, 2000 (Abstract only).
d'Emmanuele di Villa Bianca et al., "Hydrogen sulfide as a mediator of human corpus cavernosum smooth-muscle relaxation," *PNAS* 106:4513-4518, 2009.
d'Emmanuele di Villa Bianca et al., "Hydrogen sulfide and erectile function: a novel therapeutic target," *Nat. Rev. Urol.* 8:286-289, 2011 (Abstract only).
Deng et al., "Superoxide dismutase—a target for gene therapeutic approach to reduce oxidative stress in erectile dysfunction," *Methods Mol. Biol.* 610:213-227, 2010 (Abstract only).
Denizalti et al., "The vasorelaxant effect of hydrogen sulfide is enhanced in streptozotocin-induced diabetic rats," *Naunyn Schmiedebergs Arch Pharmacol.* 383:509-517, 2011 (Abstract only).
Deplancke et al., "Hydrogen sulfide induces serum-independent cell cycle entry in nontransformed rat intestinal epithelial cells," *The FASEB Journal* 17:1310-1312, 2003.
Desai et al., "Hydrogen sulfide and the metabolic syndrome," *Expert Rev. Clin. Pharmacol.* 4:63-73, 2011.
Dinkova-Kostova et al., "Extremely potent triterpenoid inducers of the phase 2 response: Correlations of protection against oxidant and inflammatory stress," *PNAS* 102:4584-4589, 2005.
Dinkova-Kostova et al., "The Role of Keap1 in Cellular Protective Responses," *Chemical Research in Toxicology* 18:1779-1791, 2005.
Dirsch et al., "Ajoene, a Compound of Garlic, Induces Apoptosis in Human Promyeloleukemic Cells, Accompanied by Generation of Reactive Oxygen Species and Activation of Nuclear Factor κB," *Mol. Pharmacol.* 53:402-407, 1998.
Distrutti, "Hydrogen sulphide and pain," *Inflamm. Allergy Drug Targets* 10:123-132, 2011 (Abstract only).

(56) References Cited

OTHER PUBLICATIONS

Distrutti et al., "5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity," *J. Pharmacol. Exp. Ther.* 319:447458, 2006.

Distrutti et al., "Evidence That Hydrogen Sulfide Exerts Antinociceptive Effects in the Gastrointestinal Tract by Activating KATP Channels," *Journal of Pharmacology and Experimental Therapeutics* 316:325-335, 2006.

Dombkowski et al., "Hydrogen sulfide as an endogenous regulator of vascular smooth muscle tone in trout," *Am. J. Physiol. Regul. Integr. Comp. Physiol.* 286:R678-R685, 2004.

Doñate et al., "Identification of biomarkers for the antiangiogenic and antitumour activity of the superoxide dismutase 1 (SOD1) inhibitor tetrathiomolybdate (ATN-224)," *British Journal of Cancer* 98:776-783, 2008.

Dröge, "Aging-related changes in the thiol/disulfide redox state: implications for the use of thiol antioxidants," *Experimental Gerontology* 37:1331-1343, 2002.

Dröge, "Oxidative stress and ageing: is ageing a cysteine deficiency syndrome?," *Phil. Trans. R. Soc. B*, 360:2355-2372, 2005.

Dröge et al., "Aberrant Insulin Receptor Signaling and Amino Acid Homeostasis as a Major Cause of Oxidative Stress in Aging," *Antioxidants & Redox Signaling* 10:661-678, 2008.

Dröge et al., "Abnormal amino-acid concentrations in the blood of patients with acquired immunodeficiency syndrome (AIDS) may contribute to the immunological defect," *Biol. Chem. Hoppe. Seyler.* 369:143-148, 1988 (Abstract only).

Dröge et al., "Functions of glutathione and glutathione disulfide in immunology and immunopathology," *FASEB J.* 8:1131-1138, 1994.

Dröge et al., "Role of Cysteine and Glutathione in HIV Infection and other Diseases Associated with Muscle Wasting and Immunological Dysfunction," *FASEB J.*, 11; 1077-1089, 1997.

Eck et al., "Low concentrations of acid-soluble thiol (cysteine) in the blood plasma of HIV-1-infected patients," *Biol Chem Hoppe Seyler*, 370:101-8, 1989 (Abstract only).

Eghbal, "Role of hydrogen sulfide in modulating the life and death of cells," Ottawa: National Library of Canada, 1999.

Ekmekcioglu et al., "Effect of sulfur baths on antioxidative defense systems, peroxide concentrations and lipid levels in patients with degenerative osteoarthritis," *Forsch Komplementarmed Klass Naturheilkd*. 9:216-220, 2002 (Abstract only).

Elrod et al., "Hydrogen sulfide attenuates myocardial ischemia-reperfusion injury by preservation of mitochondrial function," *PNAS* 104:15560-15565, 2007.

Elsey et al., "L-cysteine Stimulates Hydrogen Sulfide Synthesis in Myocardium Associated with Attenuation of Ischemia-Reperfusion Injury," *J Cardiovasc Pharmacol Ther*, 15; 53-9, 2010 (abstract only).

Era et al., "Age-related change in redox state of human serum albumin," *Biochim. Biophys. Acta*. 1247:12-16, 1995 (Abstract only).

Esechie et al., "Protective Effect of Hydrogen Sulfide in a Murine Model of Acute Lung Injury Induced by Combined Burn and Smoke Inhalation," *Clinical Science*, 115; 91-97, 2008.

Everett et al., "Perthiyl Radicals, Trisulfide Radical Ions, and Sulfate Formation. A Combined Photolysis and Radiolysis Study on Redox Processes with Organic Di- and Trisulfides," *J. Phys. Chem.* 96:306-314, 1992.

Fahey et al., "Sulforaphane inhibits extracellular, intracellular, and antibiotic-resistant strains of *Helicobacter pylori* and prevents benzo[a]pyrene-induced stomach tumors," *PNAS* 99:7610-7615, 2002.

Faller et al., "Inhaled hydrogen sulfide protects against ventilator-induced lung injury," *Anesthesiology* 113:104-115, 2010 (Abstract only).

Fidelus et al., "Glutathione and lymphocyte activation: a function of ageing and auto-immune disease," *Immunology* 61:503-508, 1987.

Filomeni et al., "Reactive Oxygen Species-dependent c-Jun NH2-terminal Kinase/c-Jun Signaling Cascade Mediates Neuroblastoma Cell Death Induced by Diallyl Disulfide," *Cancer Research*, 63; 5940-5949, 2003.

Fimognari et al., "The new isothiocyanate 4-(methylthio)butylisothiocyanate selectively affects cell-cycle progression and apoptosis induction of human leukemia cells," *Invest New Drugs* 22(2):119-129, 2004 (Abstract only).

Fiorucci, "Hydrogen sulfide: from physiology to pharmacology," *Inflamm Allergy Drug Targets* 10:77-84, 2011 (Abstract only).

Fiorucci et al., "Enhanced activity of a hydrogen sulphide-releasing derivative of mesalamine (ATB-429) in a mouse model of colitis," *British Journal of Pharmacology* 150:996-1002, 2007.

Fiorucci et al., "Hydrogen sulfide-based therapies: focus on H2S releasing NSAIDs," *Inflamm Allergy Drug Targets* 10:133-140, 2011 (Abstract only).

Fiorucci et al., "Inhibition of hydrogen sulfide generation contributes to gastric injury caused by anti-inflammatory nonsteroidal drugs," *Gastroenterology* 129:1210-1224, 2005 (Abstract only).

Fiorucci et al., "The Emerging Roles of Hydrogen Sulfide in the Gastrointestinal Tract and Liver," *Gastroenterology* 131:259-271, 2006.

Fisher et al., "Induction of Drug-Metabolizing Enzymes by Garlic and Allyl Sulfide Compounds via Activation of Constitutive Androstane Receptor and Nuclear Factor E2 Related Factor 2," *Drug Metabolism and Disposition* 35:995-1000, 2007.

Franco et al., "The central role of glutathione in the pathophysiology of human diseases," *Arch Physiol Biochem* 113:234-258, 2007 (Abstract only).

Fruehauf et al., "Reactive oxygen species: an Achilles' heel of melanoma?," *Expert Rev Anticancer Ther.*, 8; 1751-1757, 2008 (abstract only).

Fu et al., "Hydrogen sulfide protects rat lung from ischemia-reperfusion injury," *Life Sci* 82:1196-1202, 2008 (Abstract only).

Furne et al., "Oxidation of Hydrogen Sulfide and Methanethiol to Thiosulfate by Rat Tissues: a Specialized Function of the Colonic Mucosa," *Biochem Pharmacol*, 62:255-259, 2001 (abstract only).

Furne et al., "Whole tissue hydrogen sulfide concentrations are orders of magnitude lower than presently accepted values," *Am. J. Physiol. Regul. Integr. Comp. Physiol*. 295:R1479-R1485, 2008.

Gadalla et al., "Hydrogen Sulfide as a Gasotransmitter," *J Neurochem*. 113:14-26, 2010.

Gao et al., "The protective role of hydrogen sulfide in myocardial ischemia-reperfusion-induced injury in diabetic rats," *Int J. Cardiol* 152(2):177-183, 2011 (Abstract only).

Gatti et al., "Peroxynitrite-Mediated Oxidation of Albumin to the Protein-Thiyl Free Radical," *FEBS Letters* 348:287-290, 1994.

Giles et al., "Oxidation of Biological Thiols by Highly Reactive Disulfide-S-Oxides," *Gen. Physiol. Biophys*, 21:65-72, 2002.

Giles et al., "Reactive sulphur species: an in vitro investigation of the oxidation properties of disulphide S-oxides," *Biochem. J.* 364:579-585, 2002.

Giovagnini et al., "Chemical and Biological Profiles of Novel Copper(II) Complexes Containing S-Donor Ligands for the Treatment of Cancer," *Inorg. Chem.* 47:6336-6343, 2008.

Giustarini et al., "Age-related influence on thiol, disulfide, and protein-mixed disulfide levels in human plasma," *J. Gerontol. A. Biol. Sci. Med. Sci.* 61:1030-1038, 2006 (Abstract only).

Giustarini et al., "Modulation of Thiol Homeostasis Induced by H2S-Releasing Aspirin," *Free Radic Biol Med*, 48:1263-1272, 2010 (abstract only).

Givvimani et al., "Hydrogen sulfide mitigates transition from compensatory hypertrophy to heart failure," *J Appl Physiol.* 110:1093-1100, 2011.

Gliubich et al., "Active Site Structural Features for Chemically Modified Forms of Rhodanese," *The Journal of Biological Chemistry* 271:21054-21061, 1996.

Gobbi et al., "Hydrogen sulfide impairs keratinocyte cell growth and adhesion inhibiting mitogen-activated protein kinase signaling," *Laboratory Investigation* 89:994-1006, 2009.

Gokce et al., "Glutathione Depletion by Buthionine Sulfoximine Induces Oxidative Damage to DNA in Organs of Rabbits in Vivo," *Biochemistry* 48:4980-4987, 2009.

(56) References Cited

OTHER PUBLICATIONS

Gong et al., "A New Hope for Neurodegeneration: Possible Role of Hydrogen Sulfide," *Journal of Alzheimer's Disease* 24:1-10, 2011.
Goubern et al., "Sulfide, the first inorganic substrate for human cells," *The FASEB Journal* 21:1699-1706, 2007.
Grabowski et al., "Dimethyl Disulfide: Anion-Molecule Reactions in the Gas Phase at 300 K," *J. Am. Chem. Soc.* 111:1193-1203, 1989.
Grabski et al., "Hydrogen sulfide water balneum effect on erythrocyte superoxide dismutase activity in patients with rheumatoid arthritis—in vitro study," *Przegl Lek* 61:1405-1409, 2004 (Abstract only).
Granfeldt et al., "Protective Ischaemia in Patients: Preconditioning and Postconditioning," *Cardiovascular Research*, 83; 234-246, 2009.
Greco et al., "Efficient treatment of infertility due to sperm DNA damage by ICSI with testicular spermatozoa," *Human Reproduction* 20:226-230, 2005.
Greer, "On the Origin of Cytotoxicity of the Natural Product Varacin. A Novel Example of a Pentathiepin Reaction That Provides Evidence for a Triatomic Sulfur Intermediate," *J. Am. Chem. Soc.* 123:10379-10386, 2001.
Gu et al., "Characterization of trisulfide modification in antibodies," *Analytical Biochemistry* 400:89-98, 2010.
Gu et al., "Therapeutic applications of organosulfur compounds as novel hydrogen sulfide donors and/or mediators," *Expert Rev. Clin. Pharmacol.* 4:123-133, 2011.
Guayerbas et al., "Thiolic antioxidant supplementation of the diet reverses age-related behavioural dysfunction in prematurely ageing mice," *Pharmacol. Biochem. Behav.* 80:45-51, 2005 (Abstract only).
Guo et al., "Neuroprotective effects of diallyl trisulfide in SOD1-G93A transgenic mouse model of amyotrophic lateral sclerosis," *Brain Res.* 1374:110-115, 2011 (Abstract only).
Guo et al., "Protective Effect of Allitridi on Hippocampus of Rats with Cerebral Ischemia-Refusion and P53 Expression," *Chinese Journal of Pathophysiology* 25:264-267, 2009 (Abstract only).
Güven et al., "Age-related changes on glucose transport and utilization of human erythrocytes: effect of oxidative stress," *Gerontology* 45:79-82, 1999 (Abstract only).
Ha et al., "Effects of allitridi on cell cycle arrest of human gastric cancer cells," *World J. Gastroenterol.* 11:5433-5437, 2005 (Abstract only).
Halen et al., "Prodrug Designing of NSAIDs," *Mini-Reviews in Medicinal Chemistry*, 9:124-139, 2009.
Han et al., "Hydrogen Sulfide Ameliorates Tobacco Smoke-Induced Oxidative Stress and Emphysema in Mice," *Antioxidants & Redox Signaling* 15:2121-2134, 2011.
Hayakawa et al., "Alteration of redox state of human serum albumin in patients under anesthesia and invasive surgery," *J. Chromatogr. B. Biomed. Sci. Appl.* 698:27-33, 1997 (Abstract only).
Hayashi et al., "The importance of sample preservation temperature for analysis of the redox state of human serum albumin," *Clin Chim Acta.* 316(1-2):175-178, 2002 (Abstract only).
Henderson et al., "Therapeutic delivery of hydrogen sulfide for salvage of ischemic skeletal muscle after the onset of critical ischemia," *J. Vasc. Surg.* 53:785-791, 2011 (Abstract only).
Henderson et al., "Therapeutic metabolic inhibition: hydrogen sulfide significantly mitigates skeletal muscle ischemia reperfusion injury in vitro and in vivo," *Plast. Reconstr. Surg.* 126:1890-1898, 2010 (Abstract only).
Herman-Antosiewicz et al., "Activation of a novel ataxia-telangiectasia mutated and Rad3 related/checkpoint kinase 1-dependent prometaphase checkpoint in cancer cells by diallyl trisulfide, a promising cancer chemopreventive constituent of processed garlic," *Mol. Cancer Ther.* 6:1249-1261, 2007 (Abstract only).
Herman-Antosiewicz et al., "Checkpoint Kinase 1 Regulates Diallyl Trisulfide-induced Mitotic Arrest in Human Prostate Cancer Cells," *The Journal of Biological Chemistry* 280:28519-28528, 2005.
Herman-Antosiewicz et al., "Molecular targets of cancer chemoprevention by garlic-derived organosulfides," *Acta. Pharmacol. Sin.* 28:1355-1364, 2007.

Hitchler et al., "An epigenetic perspective on the free radical theory of development," *Free Radic. Biol. Med.* 43:1023-1036, 2007.
Hildebrandt et al., "Three enzymatic activities catalyze the oxidation of sulfide to thiosulfate in mammalian and invertebrate mitochondria," *FEBS Journal* 275:3352-3361, 2008.
Hosoki et al., "The possible role of hydrogen sulfide as an endogenous smooth muscle relaxant in synergy with nitric oxide," *Biochem Biophys Res Commun.* 237(3):572-531, 1997 (Abstract only).
Hosono et al., "Alkenyl group is responsible for the disruption of microtubule network formation in human colon cancer cell line HT-29 cells," *Carcinogenesis* 29:1400-1406, 2008.
Hosono et al., "Diallyl Trisulfide Suppresses the Proliferation and Induces Apoptosis of Human Colon Cancer Cells through Oxidative Modification of β-Tubulin," *The Journal of Biological Chemistry* 280:41487-41493, 2005.
Houk et al., "Measurement of Thiol-Disulfide Interchange Reactions and Thiol pKa Values," *Methods in Enzymology* 143:129-140, 1987.
Howard et al., "Garlic-Derived S-allylmercaptocysteine is a Novel In vivo Antimetastatic Agent for Androgen-Independent Prostate Cancer," *Clin. Cancer Res.* 13:1847-1856, 2007.
Hsu et al., "Five Cysteine-Containing Compounds Have Antioxidative Activity in Balb/cA Mice," *J. Nutr.* 134:149-152, 2004.
Hsu et al., "Protective Effect of S-Allyl Cysteine and S-Propyl Cysteine on Acetaminophen-Induced Hepatotoxicity in Mice," *Food Chem Toxicol*, 44; 393-397, 2006 (abstract only).
Hu, "Hydrogen Sulfide: A Novel Neuroprotective Agent to Treat Parkinson's Disease," Department of Pharmacology, National University of Singapore, 2010.
Hu et al., "Hydrogen sulfide attenuates lipopolysaccharide-induced inflammation by inhibition of p38 mitogen-activated protein kinase in microglia," *Journal of Neurochemistry* 100:1121-1128, 2007.
Hua et al., "Oxidation and generation of hydrogen peroxide by thiol compounds in commonly used cell culture media," *Biochem Biophys Res Commun*, 286:991-994, 2001 (abstract only).
Huang et al., "Effect of taurine on advanced glycation end products-induced hypertrophy in renal tubular epithelial cells," *Toxicol. Appl. Pharmacol.* 233:220-226, 2008 (Abstract only).
Huang et al., "Inhibition of ICAM-1 gene expression, monocyte adhesion and cancer cell invasion by targeting IKK complex: molecular and functional study of novel α-methylene-γ-butyrolactone derivatives," *Carcinogenesis* 25:1925-1934, 2004.
Huang et al., "The glutathione dependence of inorganic sulfate formation from L- or D-cysteine in isolated rat hepatocytes," *Chem Biol Interact.* 110(3):189-202, 1998 (Abstract only).
Hughes et al., "Making and working with hydrogen sulfide: The chemistry and generation of hydrogen sulfide in vitro and its measurement in vivo: A review," *Free Radical Biology & Medicine* 7:1346-1353, 2009.
Huovinen et al., "Inorganic sulphate, sulphite and sulphide as sulphur donors in the biosynthesis of sulphur amino acids in germ-free and conventional rats," *Biochimica et Biophysica Acta* 136:441-447, 1967.
Iciek et al., "Allyl disulfide as donor and cyanide as acceptor of sulfane sulfur in the mouse tissues," *Pharmacological Reports* 57:212-218, 2005.
Iciek et al., "Biosynthesis and biological properties of compounds containing highly reactive, reduced sulfane sulfur," *Pol. J. Pharmacol.* 53:215-225, 2001.
Iitsuka et al., "Relationship Between Lipophilicity and Inhibitory Activity Against Cancer Cell Growth of Nine Kinds of Alk(en)yl Trisulfides With Different Side Chains," *Oncology Research* 18:575-582, 2010.
Ikehata et al., "Protein Targets of Reactive Metabolites of Thiobenzamide in Rat Liver In Vivo," *Chem Res Toxicol.* 21:1432-1442, 2008.
Ikeno et al., "Delayed occurrence of fatal neoplastic diseases in ames dwarf mice: correlation to extended longevity," *J. Gerontol. A. Biol. Sci. Med. Sci.* 58:291-296, 2003 (Abstract only).
Insko et al., "Detection of exhaled hydrogen sulphide gas in rats exposed to intravenous sodium sulphide," *British Journal of Pharmacology* 157:944-951, 2009.

(56) References Cited

OTHER PUBLICATIONS

Irvine, "Glutathione as a treatment for male infertility," *Reviews of Reproduction* 1:6-12, 1996.
Isenberg et al., "Modulation of Angiogenesis by Dithiolethione-Modified NSAIDs and Valproic acid," *British Journal of Pharmacology*, 151:142-151, 2007.
Ishigami et al., "A Source of Hydrogen Sulfide and a Mechanism of Its Release in the Brain," *Antioxidants & Redox Signaling* 11:205-214, 2009.
Iwao et al, "The Structural and Pharmacokinetic Properties of Oxidized Human Serum Albumin, Advanced Oxidation Protein Products (AOPP)," *Drug Metab. Pharmacokinet.* 21(2):140-146, 2006.
Jacob et al., "Perspective on Recent Developments on Sulfur-Containing Agents and Hydrogen Sulfide Signaling," *Planta. Med.* 74:1580-1592, 2008.
Jaeschke et al., "Diurnal fluctuation and pharmacological alteration of mouse organ glutathione content," *Biochem. Pharmacol.* 34:1029-1033, 1985 (Abstract only).
Jain et al., "Glutathione deficiency leads to mitochondrial damage in brain," *Proc. Natl. Acad. Sci. USA* 88:1913-1917, 1991.
Jain et al., "Low Levels of Hydrogen Sulfide in the Blood of Diabetes Patients and Streptozotocin-Treated Rats Causes Vascular Inflammation?," *Antioxidants & Redox Signaling* 12:1333-1337, 2010.
Jespersen et al., "Characterisation of a trisulphide derivative of biosynthetic human growth hormone produced in *Escherichia coli*," *Eur. J. Biochem.* 219:365-373, 1994.
Jha et al., "Hydrogen sulfide attenuates hepatic ischemia-reperfusion injury: role of antioxidant and antiapoptotic signaling," *Am J Physiol Heart Circ Physiol* 295:H801-H806, 2008.
Ji et al., "Covalent Modification of Microsomal Lipids by Thiobenzamide Metabolites in Vivo," *Chem. Res. Toxicol.* 20:701-708, 2007.
Jiang et al., "Molecular Mechanism for H(2)S-Induced Activation of K(ATP) Channels," *Antioxid Redox Signal*, 12:1167-1178, 2010 (abstract only).
Jokic et al., "Oxidative Stress, Hemoglobin Content, Superoxide Dismutase and Catalase Activity Influenced by Sulphur Baths and Mud Packs in Patients with Osteoarthritis," *Vojnosanit Pregl* 67:573-578, 2010 (abstract only).
Jones, "Radical-free biology of oxidative stress," *Am. J. Physiol. Cell. Physiol.* 295:C849-C868, 2008.
Jones, "Redefining oxidative stress," *Antioxid Redox Signal.*, 8; 1865-1879, 2006 (abstract only).
Jones et al., "Oxygen free radicals and the penis," *Expert Opin Pharmacother*, 3:889-897, 2002 (abstract only).
Jones et al., "Redox State of Glutathione in Human Plasma," *Free Radic Biol Med.*, 28; 625-635, 2000 (abstract only).
Julius et al., "Glutathione and morbidity in a community-based sample of elderly," *J. Clin. Epidemiol.* 47:1021-1026, 1994 (Abstract only).
Jun et al., "N-acetylcysteine Stimulates Osteoblastic Differentiation of Mouse Calvarial Cells," *J Cell Biochem*, 103:1246-1255, 2008 (abstract only).
Jung et al., "The Nrf2 system as a potential target for the development of indirect antioxidants," *Molecules* 15:7266-7291, 2010 (Abstract only).
Jurkowska et al., "N-acetyl-L-cysteine as a Source of Sulfane Sulfur in Astrocytoma and Astrocyte Cultures: Correlations with Cell Proliferation," *Amino Acids*, 34:231-237, 2008 (abstract only).
Kabil et al., "Redox Biochemistry of Hydrogen Sulfide," *The Journal of Biological Chemistry* 285:21903-21907, 2010.
Kaium et al., "H2S Donor, S-Propargyl-Cysteine, Increases CSE in SGC-7901 and Cancer-Induced Mice: Evidence for a Novel Anti-Cancer Effect of Endogenous H2S?," *PLos One* 6:e20525, 2011.
Kaji et al., "Mechanism of Hydrogen Sulfide Formation from Thiosulfate," *J. Bacteriol.* 77:630-637, 1959.
Kaltenbach et al., "Comparison of five agents in protecting the cochlea against the ototoxic effects of cisplatin in the hamster," *Otolaryngol. Head Neck Surg.* 117:493-500, 1997 (Abstract only).

Kamoun, "Endogenous production of hydrogen sulfide in mammals," *Amino Acids.* 26:243-254, 2004 (Abstract only).
Kamyshny, Jr. et al., "Equilibrium Distribution of Polysulfide Ions in Aqueous Solutions at Different Temperatures by Rapid Single Phase Derivatization," *Environ. Sci. Technol.* 41:2395-2400, 2007.
Kamyshny, Jr. et al., "Formation of Carbonyl Sulfide by the Reaction of Carbon Monoxide and Inorganic Polysulfides," *Environ. Sci. Technol.* 37:1865-1872, 2003.
Kamyshny, Jr. et al., "Method for the Determination of Inorganic Polysulfide Distribution in Aquatic Systems," *Anal. Chem.* 78:2631-2639, 2006.
Kaneko et al., "Glucose-induced production of hydrogen sulfide may protect the pancreatic beta-cells from apoptotic cell death by high glucose," *FEBS Letters* 583:377-382, 2009.
Kaneto et al., "Beneficial Effects of Antioxidants in Diabetes: Possible Protection of Pancreatic β-Cells Against Glucose Toxicity," *Diabetes* 48:2398-2406, 1999.
Kaneto et al., "Involvement of oxidative stress in the pathogenesis of diabetes," *Antioxid Redox Signal* 9:355-366, 2007 (Abstract only).
Kawakami et al., "Dietary Isothiocyanates Modify Mitochondrial Functions through Their Electrophilic Reaction," *Biosci. Biotechnol. Biochem.* 69:2439-2444, 2005.
Kawakami et al., "Identification and characterization of oxidized human serum albumin: A slight structural change impairs its ligand-binding and antioxidant functions," *FEBS Journal* 273:3346-3357, 2006.
Kay et al., "Nrf2 inhibits LXRα-dependent hepatic lipogenesis by competing with FXR for acetylase binding," *Antioxid Redox Signal* 15:2135-2146, 2011 (Abstract only).
Kefer et al., "Role of Antioxidants in the Treatment of Male Infertility," *International Journal of Urology*, 16; 449-457, 2009.
Keire et al., "Kinetics and Equilibria of Thiol/Disulfide Interchange Reactions of Selected Biological Thiols and Related Molecules with Oxidized Glutathione," *J. Org. Chem.* 57:123-127, 1992.
Kennett et al., "Redox Reactions and Electron Transfer Across the Red Cell Membrane," *Life*, 55; 375-385, 2003.
Kessler, "Enzymatic activation of sulfur for incorporation into biomolecules in prokaryotes," *FEMS Microbiol. Rev.* 30:825-840, 2006.
Khanna et al., "Protective Effects of Anethole Dithiolethione Against Oxidative Stress-Induced Cytotoxicity in Human Jurkat T Cells," *Biochem Pharmacol*, 56; 61-69, 1998 (abstract only).
Khiar et al., "Enantiopure Sulforaphane Analogues with Various Substituents at the Sulfinyl Sulfur: Asymmetric Synthesis and Biological Activities," *J. Org. Chem.* 74:6002-6009, 2009.
Kida et al., "Inhaled Hydrogen Sulfide Prevents Neurodegeneration and Movement Disorder in a Mouse Model of Parkinson's Disease," *Antioxidants & Redox Signaling* 15:343-352, 2011.
Kil et al., "Glutathionylation regulates IkappaB," *Biochem Biophys Res Commun*, 373:169-173, 2008 (Abstract only).
Kim et al., "Mitochondria-Mediated Apoptosis by Diallyl Trisulfide in Human Prostate Cancer Cells is Associated with Generation of Reactive Oxygen Species and Regulated by Bax/Bak," *Mol. Cancer Ther.* 6:1599-1609, 2007.
Kimura, "Hydrogen sulfide: its production, release and functions," *Amino Acids* 41:113-121, 2011 (Abstract only).
Kimura et al., "Hydrogen Sulfide Increases Glutathione Production and Suppresses Oxidative Stress in Mitochondria," *Antioxidants & Redox Signaling* 12:1-13, 2010.
Kimura et al., "Hydrogen sulfide protects neurons from oxidative stress," *The FASEB Journal* 18:1165-1167, 2004.
Kinscherf et al., "Effect of glutathione depletion and oral N-acetylcysteine treatment on CD4+ and CD8+ cells," *FASEB J.* 8:448-451, 1994.
Kitteringham et al., "Proteomic Analysis of Nrf2 Deficient Transgenic Mice Reveals Cellular Defence and Lipid Metabolism as Primary Nrf2-Dependent Pathways in the Liver," *Journal of Proteomics*, 73; 1612-1631, 2010.
Klaassen et al., "Nrf2 the Rescue: Effects of the Antioxidative/Electrophilic Response on the Liver," *Toxicol Appl Pharmacol*, 244:57-65, 2010.
Klatt et al., "Redox regulation of c-Jun DNA binding by reversible S-glutathiolation," *The FASEB Journal*, 13; 1481-1490, 1999.

(56) References Cited

OTHER PUBLICATIONS

Kleinjan, "Biologically Produced Sulfur Particles and Polysulfide Ions: Effects on a Biotechnological Process for the Removal of Hydrogen Sulfide from Gas Streams," Wageningen Universiteit, 2005.
Kloesch et al., "Inhibitors of p38 and ERK1/2 MAPkinase and hydrogen sulphide block constitutive and IL-1β-induced IL-6 and IL-8 expression in the human chondrocyte cell line C-28/I2," *Rheumatol Int* 32:729-736, 2012 (Abstract only).
Kohama et al., "Studies on Thermophile Products. IV. Structural Elucidation of Cytotoxic Substance, BS-1, Derived from *Bacillus stearothermophilus*," *Chem. Pharm. Bull.*, 40; 2210-2211, 1992.
Koj et al., "[35S]Thiosulphate Oxidation by Rat Liver Mitochondria in the Presence of Glutathione," *Biochem. J.* 103:791-795, 1967.
Koppers et al., "The role of cysteine-rich secretory proteins in male fertility," *Asian Journal of Andrology* 13:111-117, 2011.
Kowald, "The Mitochondrial Theory of Aging," *Biol. Signals Recept.* 10:162-175, 2001.
Kraus et al., "Purification and Properties of Cystathionine β-Synthase from Human Liver: Evidence for Identical Subunits," *The Journal of Biological Chemistry*, 253; 6523-6528, 1978.
Kwak et al., "Modulation of Gene Expression by Cancer Chemopreventive Dithiolethiones through the Keap1-Nrf2 Pathway" *The Journal of Biological Chemistry* 278:8135-8145, 2003.
Laggner et al., "Hydrogen sulphide: a novel physiological inhibitor of LDL atherogenic modification by HOCl," *Free Radic Res* 41:741-747, 2007 (Abstract only).
Lamy et al., "MTBITC Mediates Cell Cycle Arrest and Apoptosis Induction in Human HepG2 Cells Despite its Rapid Degradation Kinetics in the In Vitro Model," *Environmental and Molecular Mutagenesis*, 50:190-200, 2009.
Lan et al., "Allitridi induces apoptosis by affecting Bcl-2 expression and caspase-3 activity in human gastric cancer cells," *Acta. Pharmacol. Sin.* 25:219-225, 2004.
Lands et al., "Effect of supplementation with a cysteine donor on muscular performance," *J. Appl. Physiol.* 87:1381-1385, 1999.
Lang et al., "Blood glutathione: a biochemical index of life span enhancement in the diet restricted Lobund-Wistar rat," *Prog. Clin. Biol. Res.* 287:241-246, 1989 (Abstract only).
Lang et al., "High blood glutathione levels accompany excellent physical and mental health in women ages 60 to 103 years," *J Lab Clin Med* 140:413-417, 2002 (Abstract only).
Lavu et al., "Hydrogen sulfide-mediated cardioprotection: mechanisms and therapeutic potential," *Clinical Science* 120:219-229, 2011.
Le Faou et al., "Thiosulfate, polythionates and elemental sulfur assimilation and reduction in the bacterial world," *FEMS Microbiol. Rev.* 6:351-381, 1990 (Abstract only).
Lean et al., "A crucial role for thiol antioxidants in estrogen-deficiency bone loss," *J. Clin. Invest.* 112:915-923, 2003.
Lee et al., "A crucial role for reactive oxygen species in RANKL-induced osteoclast differentiation," *Blood* 106:852-859, 2005.
Lee et al., "Astrocytes produce the antiinflammatory and neuroprotective agent hydrogen sulfide," *Neurobiol. Aging* 30:1523-1534, 2009 (Abstract only).
Lee et al., "Effects of Hydrogen Sulfide-releasing L-DOPA Derivatives on Glial Activation," *Journal of Biological Chemistry* 285:17318-17328, 2010.
Lee et al., "Effects of interventions on oxidative stress and inflammation of cardiovascular diseases," *World Journal of Cardiology* 3:18-24, 2011.
Lee et al., "Hydrogen sulfide-releasing NSAIDs attenuate neuroinflammation induced by microglial and astrocytic activation," *Glia* 58:103-113, 2010 (Abstract only).
Lee et al., "Role of Bim in diallyl trisulfide-induced cytotoxicity in human cancer cells," *J Cell Biochem.* 112:118-127, 2011.
Lee et al., "The Slow-Releasing Hydrogen Sulfide Donor, GYY4137, Exhibits Novel Anti-Cancer Effects In Vitro and In Vivo," *PLoS ONE* 6:e21077, 2011.
Lefer, "A new gaseous signaling molecule emerges: Cardioprotective role of hydrogen sulfide," *PNAS* 104:17907-17908, 2007.
Lefer, "Potential importance of alterations in hydrogen sulphide (H2S) bioavailability in diabetes," *British Journal of Pharmacology* 155:617-619, 2008.
Lefer et al., "Peroxynitrite Inhibits Leukocyte-Endothelial Cell Interactions and Protects Against Ischemia-Reperfusion Injury in Rats," *J. Clin. Invest.* 99:684-691, 1997.
Leibetseder et al., "Improving homocysteine levels through balneotherapy: effects of sulphur baths," *Clin Chim Acta* 343:105-111, 2004 (Abstract only).
Leiser et al., "Nrf2 Signaling, a Mechanism for Cellular Stress Resistance in Long-Lived Mice," *Molecular and Cellular Biology* 30:871-884, 2010.
Leslie et al., "Sulphur and skin: from Satan to Saddam!," *J Cosmet Dermatol* 3:94-98, 2004 (Abstract only).
Levitt et al., "Detoxification of hydrogen sulfide and methanethiol in the cecal mucosa," *J. Clin. Invest.* 104:1107-1114, 1999.
Levitt et al., "Free and Acid-Labile Hydrogen Sulfide Concentrations in Mouse Tissues: Anomalously High Free Hydrogen Sulfide in Aortic Tissue," *Antioxidants & Redox Signaling* 15:373-378, 2011.
Li et al., "An intervention study to prevent gastric cancer by microselenium and large dose of allitridium," *Chinese Medical Journal* 117:1155-1160, 2004.
Li et al., "An oil-free microemulsion for intravenous delivery of diallyl trisulfide: formulation and evaluation," *Int. J. Pharm.* 407:158-166, 2011 (Abstract only).
Li et al., "Anti-inflammatory and gastrointestinal effects of a novel diclofenac derivative," *Free Radic. Biol. Med.* 42:706-719, 2007 (Abstract only).
Li et al., "Antitumor activity of Z-ajoene, a natural compound purified from garlic: antimitotic and microtubule-interaction properties," *Carcinogenesis* 23:573-579, 2002.
Li et al., "Calcium sulfide (CaS), a donor of hydrogen sulfide (H(2)S): a new antihypertensive drug?," *Med. Hypotheses.* 73:445-447, 2009 (Abstract only).
Li et al., "Characterization of a Novel, Water-Soluble Hydrogen Sulfide-Releasing Molecule (GYY4137): New Insights Into the Biology of Hydrogen Sulfide," *Circulation* 117:2351-2360, 2008.
Li et al., "GYY4137, a novel hydrogen sulfide-releasing molecule, protects against endotoxic shock in the rat," *Free Radic Biol Med* 47:103-113, 2009 (Abstract only).
Li et al., "Hydrogen Sulfide and Cell Signaling," *Annu. Rev. Pharmacol. Toxicol.* 51:169-187, 2011.
Li et al., "Interaction between Hydrogen Sulfide and Nitric Oxide on Cardiac Protection in Rats with Metabolic Syndrome," *Acta Academiae Medicinae Sinicae* 33:25-32, 2011 (Abstract only).
Li et al., "Putative biological roles of hydrogen sulfide in health and disease: a breath of not so fresh air?," *Trends in Pharmacological Sciences* 29:84-90, 2007.
Liby et al., "The Synthetic Triterpenoids, CDDO and CDDO-Imidazolide, Are Potent Inducers of Heme Oxygenase-1 and Nrf2/ARE Signaling," *Cancer Res.* 65:4789-4798, 2005.
Limón-Pacheco et al., "Glutathione depletion activates mitogen-activated protein kinase (MAPK) pathways that display organ-specific responses and brain protection in mice," *Free Radic Biol Med* 43:1335-1347, 2007 (Abstract only).
Lin et al., "Antiglycative and anti-VEGF effects of s-ethyl cysteine and s-propyl cysteine in kidney of diabetic mice," *Mol. Nutr. Food Res.* 52:1358-1364, 2008 (Abstract only).
Lin et al., "Sulfur revisited," *J Am Acad Dermatol* 18:553-558, 1988.
Liu et al., "Advanced glycation end products accelerate ischemia/reperfusion injury through receptor of advanced end product/nitrative thioredoxin inactivation in cardiac microvascular endothelial cells," *Antioxid. Redox. Signal.* 15:1769-1778, 2011 (Abstract only).
Liu et al., "Glutathione metabolism during aging and in Alzheimer disease," *Ann N Y Acad Sci* 1019:346-349, 2004 (Abstract only).
Liu et al., "The antibacterial mode of action of allitridi for its potential use as a therapeutic agent against *Helicobacter pylori* infection," *FEMS Microbiol Lett* 303:183-189, 2009 (Abstract only).
Loffredo et al., "Oxidative-Stress-Mediated Arterial Dysfunction in Patients with Peripheral Arterial Disease," *European Heart Journal* 28:608-612, 2007.

(56) References Cited

OTHER PUBLICATIONS

Lopes et al., "Reactive Oxygen Species: potential Cause for DNA Fragmentation in Human Spermatozoa," *Human Reproduction*, 13; 869-900, 1998.

Lowicka et al., "Hydrogen sulfide (H2S)—the third gas of interest for pharmacologists," *Pharmacological Reports* 59:4-24, 2007.

Lu et al., "Inflammation, a Key Event in Cancer Development," *Mol Cancer Res* 4:221-233, 2006.

Luther et al., "Thermodynamics and kinetics of sulfide oxidation by oxygen: a look at inorganically controlled reactions and biologically mediated processes in the environment," *Front. Microbiol.* 2:1-9, 2011.

Lynn et al., "Hydrogen sulfide in the pathogenesis of atherosclerosis and its therapeutic potential," *Expert Rev. Clin. Pharmacol.* 4:97-108, 2011.

Maher et al., "The rise of antioxidant signaling—the evolution and hormetic actions of Nrf2," *Toxicol Appl Pharmacol.* 244(1):4-15, 2010 (Abstract only).

Makker et al., "Oxidative stress & male infertility," *Indian J Med Res*, 129:357-367, 2009.

Mancini et al., "Clinical, functional and quality of life changes after balneokinesis with sulphurous water in patients with varicose veins," *Vasa.* 32:26-30, 2003 (Abstract only).

Mantovani et al., "Cancer-Related Anorexia/Cachexia Syndrome and Oxidative Stress: An Innovative Approach beyond Current Treatment," *Cancer Epidemiol. Biomarkers Prev.* 13:1651-1659, 2004.

Mari et al., "Mitochondrial Glutathione, a Key Survival Antioxidant," *Antioxidants & Redox Signaling* 11:2685-2700, 2009.

Markovic et al., "Beneficial effects of cellular stress response in traditional spa treatment of rheumatoid arthritis," *Clin. Lab.* 55:235-241, 2009 (Abstract only).

Marsden, "Low-Molecular-Weight S-Nitrosothiols and Blood Vessel Injury," *The Journal of Clinical Investigation*, 117:2377-2380, 2007.

Martelli et al., "Hydrogen sulphide: novel opportunity for drug discovery," *Med Res Rev* Epub, 2010 (Abstract only).

Mathai et al., "No facilitator required for membrane transport of hydrogen sulfide," *PNAS* 106:16633-16638, 2009.

Matteucci et al., "Thiol Signalling Network with an Eye to Diabetes," *Molecules* 15:8890-8903, 2010.

Maxuitenko et al., "Identification of dithiolethiones with better chemopreventive properties than oltipraz," *Carcinogenesis* 19:1609-1615, 1998.

Medeiros et al., "Hydrogen Sulfide Prevents Ethanol-Induced Gastric Damage in Mice: Role of ATP-Sensitive Potassium Channels and Capsaicin-Sensitive Primary Afferent Neurons," *JPET* 330:764-770, 2009.

Meister et al., "Enzymatic Desulfuration of β-Mercaptopyruvate to Pyruvate," *J. Biol. Chem.* 206:561-575, 1954.

Meng et al., "Heat shock protein 90 mediates cytoprotection by $H_2S$ against chemical hypoxia-induced injury in PC12 cells," *Clin Exp Pharmacol Physiol* 38:42-49, 2011 (Abstract only).

Mera et al., "The structure and function of oxidized albumin in hemodialysis patients: Its role in elevated oxidative stress via neutrophil burst," *Biochem. Biophys. Res. Commun.* 334:1322-1328, 2005 (Abstract only).

Mercado et al., "Decreased histone deacetylase 2 impairs Nrf2 activation by oxidative stress," *Biochemical and Biophysical Research Communications* 406:292-298, 2011.

Mi et al., "Covalent Binding to Tubulin by Isothiocyanates: A Mechanism of Cell Growth Arrest and Apoptosis," *The Journal of Biological Chemistry* 283:22136-22146, 2008.

Mi et al., "The Role of Protein Binding in Induction of Apoptosis by Phenethyl Isothiocyanate and Sulforaphane in Human Non-Small Lung Cancer Cells," *Cancer Research* 67:6409-6416, 2007.

Mikami et al., "Thioredoxin and dihydrolipoic acid are required for 3-mercaptopyruvate sulfurtransferase to produce hydrogen sulfide," *Biochem. J.* 439:479-485, 2011.

Miller et al., "Hydrogen sulfide increases thermotolerance and lifespan in *Caenorhabditis elegans*," *PNAS* 104:20618-10622, 2007.

Minamishima et al., "Hydrogen Sulfide Improves Survival After Cardiac Arrest and Cardiopulmonary Resuscitation via a Nitric Oxide Synthase 3 -Dependent Mechanism in Mice," *Circulation* 120:888-896, 2009.

Mirandola et al., "Hydrogen sulfide inhibits IL-8 expression in human keratinocytes via MAP kinase signaling," *Laboratory Investigation* 91:1188-1194, 2011 (Abstract only).

Mishina et al., "Does cellular hydrogen peroxide diffuse or act locally?," *Antioxid. Redox Signal.* 14:1-7, 2011 (Abstract only).

Mishra et al., "H2S ameliorates oxidative and proteolytic stresses and protects the heart against adverse remodeling in chronic heart failure," *Am J Physiol Heart Circ Physiol* 298:H451-H456, 2010.

Miyoshi et al., "Benzyl isothiocyanate inhibits excessive superoxide generation in inflammatory leukocytes: implication for prevention against inflammation-related carcinogenesis," *Carcinogenesis* 25:567-575, 2004.

Miyoshi et al., "Selective cytotoxicity of benzyl isothiocyanate in the proliferating fibroblastoid cells," *Int J Cancer.*, 120; 484-492, 2007 (Abstract only).

Mohamed et al., "The role of oxidative stress and NF-kappaB activation in late diabetic complications," *Biofactors* 10:157-167, 1999 (Abstract only).

Mohora et al., "Redox-Sensitive Signaling Factors and Antioxidants," *Farmacia*, 57; 399-411, 2009.

Morrison et al., "Surviving blood loss using hydrogen sulfide," *J Trauma* 65:183-188, 2008 (Abstract only).

Morsy et al., "Curative effects of hydrogen sulfide against acetaminophen-induced hepatotoxicity in mice," *Life Sci.* 87:692-698, 2010 (Abstract only).

Mosharov et al., "The Quantitatively Important Relationship between Homocysteine Metabolism and Glutathione Synthesis by the Transsulfuration Pathway and Its Regulation by Redox Changes," *Biochemistry* 39:13005-13011, 2000.

Mueller, "Trafficking in persulfides: delivering sulfur in biosynthetic pathways," *Nat. Chem. Biol.* 2:185-194, 2006 (Abstract only).

Münchberg et al., "Polysulfides as Biologically Active Ingredients of Garlic," *Org Biomol Chem* 5:1505-1518, 2007 (abstract only).

Munday, "Toxicity of thiols and disulphides: involvement of free-radical species," *Free Radic. Biol. Med.* 7:659-673, 1989 (Abstract only).

Munday et al., "Comparative effects of mono-, di-, tri-, and tetrasulfides derived from plants of the Allium family: redox cycling in vitro and hemolytic activity and Phase 2 enzyme induction in vivo," *Free Radic. Biol. Med.* 34:1200-1211, 2003 (Abstract only).

Munday et al., "Synthesis, Biological Evaluation, and Structure-Activity Relationships of Dithiolethiones as Inducers of Cytoprotective Phase 2 Enzymes," *J. Med. Chem.* 53:4761-4767, 2010.

Mustafa et al., "H2S Signals Through Protein S-Sulfhydration," *Sci. Signal.* 2:ra72, 2009.

Mustafa et al., "Signaling by Gasotransmitters," *Sci. Signal.* 2:1-17, 2009.

Muzaffar et al., "Exogenous Hydrogen Sulfide Inhibits Superoxide Formation, NOX-1 Expression and Rac1 Activity in Human Vascular Smooth Muscle Cells," *J Vasc Res.* 45:521-528, 2008.

Nagy et al., "Rapid Reaction of Hydrogen Sulfide with the Neutrophil Oxidant Hypochlorous Acid to Generate Polysulfides," *Chem. Res. Toxicol.* 23:1541-1543, 2010.

Nakamura et al., "Electrophiles in Foods: The Current Status of Isothiocyanates and Their Chemical Biology," *Biosci. Biotechnol. Biochem.* 74:242-255, 2010.

Nakamura et al., "Involvement of the Mitochondrial Death Pathway in Chemopreventive Benzyl Isothiocyanate-induced Apoptosis," *The Journal of Biological Chemistry* 277:8492-8499, 2002.

Nakamura et al., "Purification and Properties of Thiosulfate Dehydrogenase from Acidithiobacillus Thiooxidans JCM7814," *Biosci. Biotechnol. Biochem.*, 65; 102-108, 2001.

Nakamura et al., "Redox Regulation of Glutathione S-Transferase Induction by Benzyl Isothiocyanate: Correlation of Enzyme Induction with the Formation of Reactive Oxygen Intermediates," *Cancer Res*, 60; 219-225, 2000.

Navarra et al., "Gaseous neuromodulators in the control of neuroendocrine stress axis," *Ann. N.Y. Acad. Sci.* 917:638-646, 2000 (Abstract only).

(56) References Cited

OTHER PUBLICATIONS

Neimark et al., "Efficacy of natural therapeutic factors of Belokurikha health resort in rehabilitation of patients with chronic prostatitis," *Urologiia* 5:53-56, 2005 (Abstract only).
Nelson et al., "Protection of Retinal Pigment Epithelial Cells from Oxidative Damage by Oltipraz, a Cancer Chemopreventive Agent," *Investigative Ophthalmology & Visual Science*, 43:3550-3554, 2002.
Neuwelt et al., "First Evidence of Otoprotection Against Carboplatin-Induced Hearing Loss with a Two-Compartment System in Patients with Central Nervous System Malignancy Using Sodium Thiosulfate," *The Journal of Pharmacology and Experimental Therapeutics* 286:77-84, 1998.
Nielsen et al., "Trisulfides in proteins," *Antioxid. Redox. Signal.* 15:67-75, 2011 (Abstract only).
Nimni et al., "Are we getting enough sulfur in our diet?," *Nutrition & Metabolism* 4:1-12, 2007.
Odetti et al., "Comparative Trial of N-Acetyl-Cysteine, Taurine, and Oxerutin on Skin and Kidney Damage in Long-Term Experimental Diabetes," *Diabetes* 52:499-505, 2003.
Oh et al., "Hydrogen sulfide inhibits nitric oxide production and nuclear factor-kappaB via heme oxygenase-1 expression in RAW264.7 macrophages stimulated with lipopolysaccharide," *Free Radic Biol Med* 41:106-119, 2006 (Abstract only).
Ohge et al., "The effect of antibiotics and bismuth on fecal hydrogen sulfide and sulfate-reducing bacteria in the rat," *FEMS Microbiology Letters* 228:137-142, 2003.
Okada et al., "Antioxidant activity of the new thiosulfinate derivative, S-benzyl phenylmethanethiosulfinate, from *Petiveria alliacea* L.," *Org. Biomol. Chem.* 6:1097-1102, 2008 (Abstract only).
Okado-Matsumoto et al., "Modification of Cysteine 111 in Human Cu,Zn-superoxide Dismutase," *Free Radic Biol Med*, 41:1837-1846, 2006 (abstract only).
Olson, "Is hydrogen sulfide a circulating "gasotransmitter" in vertebrate blood?," *Biochim. Biophys. Acta.* 1787:856-863, 2009 (Abstract only).
Olson, "The therapeutic potential of hydrogen sulfide: separating hype from hope," *Am. J. Physiol. Regul. Integr. Comp. Physiol.* 301:R297-R312, 2011.
Olson et al., "Hydrogen sulfide and oxygen sensing in the cardiovascular system," *Antioxid Redox Signal* 12:1219-1234, 2010 (Abstract only).
Ortega et al., "Hypotaurine and sulfhydryl-containing antioxidants reduce H2S toxicity in erythrocytes from a marine invertebrate," *The Journal of Experimental Biology* 211:3816-3825, 2008.
Osborne et al., "ACS67, a Hydrogen Sulfide-Releasing Derivative of Latanoprost Acid, Attenuates Retinal Ischemia and Oxidative Stress to RGC-5 Cells in Culture," *IOVS* 51:284-294, 2010.
Otani, "Oxidative stress as pathogenesis of cardiovascular risk associated with metabolic syndrome," *Antioxid Redox Signal*, 15:1911-1926, 2011 (abstract only).
Ou et al., "Cardiac Contractile Dysfunction and Apoptosis in Streptozotocin-Induced Diabetic Rats Are Ameliorated by Garlic Oil Supplementation," *J. Agric. Food Chem.* 58:10347-10355, 2010.
Ou et al., "Protective Action on Human LDL Against Oxidation and Glycation by Four Organosulfur Compounds Derived from Garlic," *Lipids*, 38:219-224, 2003 (abstract only).
Pae et al., "Subtle interplay of endogenous bioactive gases (NO, CO and H(2)S) in inflammation," *Arch Pharm Res*, 32:1155-1162, 2009 (Abstract only).
Palmer et al., "S-Nitrosothiols signal hypoxia-mimetic vascular pathology," *The Journal of Clinical Investigation* 117:2592-2601, 2007.
Pan et al., "Hydrogen Sulfide Attenuated Tumor Necrosis Factor-α-Induced Inflammatory Signaling and Dysfunction in Vascular Endothelial Cells," *PLoS ONE* 6:e19766, 2011.
Pecháček et al., "Decomposition Products of Allyl Isothiocyanate in Aqueous Solutions," *J. Agric. Food Chem.* 45:4584-4588, 1997.
Peck et al., "The Oxidation of Thiosulfate and Phosphorylation in Extracts of Thiobacillus thioparus," *The Journal of Biological Chemistry* 237:190-197, 1962.

Pedraza-Chaverrl et al., "S-allylmercaptocysteine scavenges hydroxyl radical and singlet oxygen in vitro and attenuates gentamicin-induced oxidative and nitrosative stress and renal damage in vivo," *BMC Clinical Pharmacology*, 4; 1-13, 2004.
Peng et al., "H2S mediates O2 sensing in the carotid body," *PNAS* 107:10719-10724, 2010.
Perna et al., "Hydrogen sulfide, the third gaseous signaling molecule with cardiovascular properties, is decreased in hemodialysis patients," *J Ren Nutr* 20:s11-s14, 2010 (Abstract only).
Pinto et al., "Redox-Sensitive Proteins Are Potential Targets of Garlic-Derived Mercaptocysteine Derivatives," *J. Nutr.*, 136; 835S-841S, 2006.
Plamer et al., "S-Nitrosothiols signal hypoxia-mimetic vascular pathology," *The Journal of Clinical Investigation*, 117; 2592-2601, 2007.
Portt et al., "Anti-apoptosis and cell survival: a review," *Biochim. Biophys. Acta.* 1813:238-259, 2011 (Abstract only).
Powolny et al., "Multitargeted prevention and therapy of cancer by diallyl trisulfide and related *Allium* vegetable-derived organosulfur compounds," *Cancer Lett.* 269:305-314, 2008.
Powolny et al., "The garlic constituent daillyl trisulfide increases the lifespan of *C. elegans* via *skn-1* activation," *Exp Gerontol.* 46(6):441-452, 2011.
Predmore et al., "Development of hydrogen sulfide-based therapeutics for cardiovascular disease," *J. Cardiovasc. Transl. Res.* 3:487-498, 2010 (Abstract only).
Predmore et al., "Hydrogen sulfide-mediated myocardial pre- and post-conditioning," *Expert Rev Clin Pharmacol.* 4:83-96, 2011.
Predmore et al., "The hydrogen sulfide signaling system: changes during aging and the benefits of caloric restriction," *Age* 32:467-481, 2010.
Predmore et al., "The Stable Hydrogen Sulfide Donor, Diallyl Trisulfide, Protects Against Acute Myocardial Infarction in Mice," *J. Am. Coll. Cardiol.* 55:A116.E1089, 2010 (Abstract only).
Pristatsky et al., "Evidence for Trisulfide Bonds in a Recombinant Variant of a Human IgG2 Monoclonal Antibody," *Anal. Chem.* 81:6148-6155, 2009.
Pryor et al., "Free radical biology and medicine: its a gas, man!," *Am. J. Physiol. Regul. Integr. Comp. Physiol.* 291:R491-R511, 2006.
Pryor et al., "Oxidation of Thiols by Nitric Oxide and Nitrogen Dioxide: Synthetic Utility and Toxicological Implications," *J. Org. Chem.* 47:156-159, 1982.
Puthalakath et al., "ER stress triggers apoptosis by activating BH3-only protein Bim," *Cell* 129:1337-1349, 2007 (Abstract only).
Qiao et al., "Thiol Oxidative Stress Induced by Metabolic Disorders Amplifies Macrophage Chemotactic Responses and Accelerates Atherogenesis and Kidney Injury in LDL Receptor-Deficient Mice," *Arterioscler. Thromb. Vasc. Biol.* 29:1779-1786, 2009.
Rábai et al., "A Model for the pH-Regulated Oscillatory Reaction between Hydrogen Peroxide and Sulfide Ion," *J. Phys. Chem.* 96:5414-5419, 1992.
Rahangdale et al., "Therapeutic interventions and oxidative stress in diabetes," *Front Biosci.* 14:192-209, 2009 (Abstract only).
Rao et al., "Reaction of Cystine with Sodium Sulfide in Sodium Hydroxide Solution," *J. Org. Chem.* 24:749-753, 1959.
Rasheed et al., "Reactive Oxygen Species Damaged Human Serum Albumin in Patients with Hepatocellular Carcinoma," *J Exp Clin Cancer Res.*, 26; 395-404, 2007 (Abstract only).
Rebrin et al., "Comparison of thiol redox state of mitochondria and homogenates of various tissues between two strains of mice with different longevities," *Exp. Gerontol.* 39:1513-1519, 2004.
Rebrin et al., "Pro-Oxidant Shift in Glutathione Redox State During Aging," *Adv Drug Deliv Rev.* 60:1545-1552, 2008.
Rees et al., "Sulfur Amino Acid Metabolism in Pregnancy: The Impact of Methionine in the Maternal Diet," *J. Nutr.* 136:1701S-1705S, 2006.
Reisman et al., "CDDO-Im Protects from Acetaminophen Hepatotoxicity Through Induction of Nrf2-Dependent Genes," *Toxicol. Appl. Pharmacol.* 236:109-114, 2009.
Rizvi et al., "Erythrocyte plasma membrane redox system in human aging," *Rejuvenation Res.* 9:470-474, 2006 (Abstract only).
Rizvi et al., "L-cysteine Influx in Erythrocytes as a Function of Human Age," *Rejuvenation Res*, 11; 661-5, 2008 (abstract only).

(56) References Cited

OTHER PUBLICATIONS

Rizvi et al., "Markers of Oxidative Stress in Erythrocytes During Aging in Humans," *Ann N Y Acad Sci*, 1100; 373-82, 2007(abstract only).
Rogers et al., "Calcific uremic arteriolopathy: advances in pathogenesis and treatment," *Semin. Dial.* 20:150-157, 2007 (Abstract only).
Rosenthal et al., "A Study of the Mechanism and Kinetics of the Thioacetamide Hydrolysis Reaction," *J. Am. Chem. Soc.* 79:2684-2690, 1957.
Rossoni et al., "Activity of a new hydrogen sulfide-releasing aspirin (ACS14) on pathological cardiovascular alterations induced by glutathione depletion in rats," *Eur. J. Pharmacol.* 648:139-145, 2010 (Abstract only).
Rossoni et al., "The hydrogen sulphide-releasing derivative of diclofenac protects against ischaemia-reperfusion injury in the isolated rabbit heart," *British Journal of Pharmacology* 153:100-109, 2008.
Ryter et al., "Heme Oxygenase-1/Carbon Monoxide: From Basic Science to Therapeutic Applications," *Physiol Rev* 86:583-650, 2006.
Sabelli et al., "Rhodanese-Thioredoxin System and Allyl Sulfur Compounds Implications in apoptosis induction," *The FEBS Journal*, 275; 3884-3899, 2008.
Saez et al., "The production of free radicals during the autoxidation of cysteine and their effect on isolated rat hepatocytes," *Biochim Biophys Acta.* 719(1):24-31, 1982 (Abstract only).
Sahu et al., "Benzyl isothiocyanate-mediated generation of reactive oxygen species causes cell cycle arrest and induces apoptosis via activation of MAPK in human pancreatic cancer cells," *Carcinogenesis* 30:1744-1753, 2009.
Salami et al., "Sulphurous water inhalations in the prophylaxis of recurrent upper respiratory tract infections," *Int J Pediatr Otorhinolaryngol* 72:1717-1722, 2008 (Abstract only).
Sanders et al., "Potential role of the antioxidant N-acetylcysteine in slowing bone resorption in early post-menopausal women: a pilot study," *Transl. Res.* 150:215, 2007.
Saravanan et al., "Antidiabetic effect of S-allylcysteine: Effect on plasma and tissue glycoproteins in experimental diabetes," *Phytomedicine* 17:1086-1089, 2010 (Abstract only).
Schafer et al., "Redox Environment of the Cell as Viewed Through the Redox State of the Glutathione Disulfide/Glutathione Couple," *Free Radic Biol Med.*, 30; 1191-1212, 2001 (abstract only).
Schicho et al., "Hydrogen sulfide is a novel prosecretory neuromodulator in the Guinea-pig and human colon," *Gastroenterology* 131:1542-1552, 2006 (Abstract only).
Schneider et al., "Metabolic Interrelations of Sulfur in Proteins, Thiosulfate, and Cystine," *The Journal of Biological Chemistry* 244:5735-5744, 1969.
Schreier et al., "Hydrogen sulfide scavenges the cytotoxic lipid oxidation product 4-HNE," *Neurotox Res* 17:249-256, 2010 (Abstract only).
Schulz, "Clinical pharmacokinetics of nitroprusside, cyanide, thiosulphate and thiocyanate," *Clin. Pharmacokinet.* 9:239-251, 1984 (Abstract only).
Searcy et al., "Interaction of Cu,Zn superoxide dismutase with hydrogen sulfide," *Arch Biochem Biophys* 318:251-263, 1995 (Abstract only).
Searcy et al., "Sulfur Reduction by Human Erythrocytes," *The Journal of Experimental Zoology* 282:310-322, 1998.
Seki et al., "Anticancer effects of diallyl trisulfide derived from garlic," *Asia Pac J Clin Nutr.* 17:249-252, 2008.
Sen et al., "Cardioprotective role of sodium thiosulfate on chronic heart failure by modulating endogenous H2S generation," *Pharmacology* 82:201-213, 2008 (Abstract only).
Sen et al., "Hydrogen sulfide ameliorates hyperhomocysteinemia-associated chronic renal failure," *Am J Physiol Renal Physiol.* 297:F410-F419, 2009.
Sen et al., "Inhibition of NF-kappa B activation in human T-cell lines by anetholdithiolthione," *Biochem Biophys Res Commun* 218:148-153, 1996 (Abstract only).
Sen et al., "Protein modifications involved in neurotransmitter and gasotransmitter signaling," *Trends Neurosci.* 33:493-502, 2010.
Senatore et al., "Nucleophilic Substitution at Sulfur. Effect of Nucleophile and Leaving Group Basicity as Probe of Bond Formation and Breaking," *Journal of the American Chemical Society* 95:2918-2922, 1973.
Seligman et al., "Nonprotein Thiols and Disulfides in Rat Epididymal Spermatozoa and Epididymal Fluid: Role of γ-Glutamyl-Transpeptidase in Sperm Maturation," *Journal of Andrology*, 26:629-637, 2005.
Shankar et al., "Diallyl trisulfide increases the effectiveness of TRAIL and inhibits prostate cancer growth in an orthotopic model: molecular mechanisms," *Mol. Cancer Ther.* 7:2328-2338, 2008 (Abstract only).
Sherman et al., "Intermittent Balneotherapy at the Dead Sea Area for Patients with Knee Osteoarthritis," *IMAJ* 12:88-93, 2009.
Shi et al., "Anti-apoptotic action of hydrogen sulfide is associated with early JNK inhibition," *Cell Biology International* 33:1095-1101, 2009 (Abstract only).
Shi et al., "Chronic sodium hydrosulfide treatment decreases medial thickening of intramyocardial coronary arterioles, interstitial fibrosis, and ROS production in spontaneously hypertensive rats," *Am. J. Physiol. Heart Circ. Physiol.* 293:H2903-H2100, 2007.
Shibuya et al., "3-Mercaptopyruvate sulfurtransferase produces hydrogen sulfide and bound sulfane sulfur in the brain," *Antioxid. Redox. Signal.* 11:703-714, 2009 (Abstract only).
Shibuya et al., "Vascular endothelium expresses 3-mercaptopyruvate sulfurtransferase and produces hydrogen sulfide," *J. Biochem.* 146:623-626, 2009 (Abstract only).
Shin et al., "NRF2 Modulates Aryl Hydrocarbon Receptor Signaling: Influence on Adipogenesis," *Molecular and Cellular Biology* 27:7188-7197, 2007.
Shin et al., "Role of Nrf2 in prevention of high-fat diet-induced obesity by synthetic triterpenoid CDDO-Imidazolide," *Eur J Pharmacol.*, 620; 138-144, 2009.
Showell et al., "Antioxidants for male subfertility," *Cochrane Database Syst. Rev.* 1:CD007411, 2011 (Abstract only).
Shukla et al., "Effect of hydrogen sulphide-donating sildenafil (ACS6) on erectile function and oxidative stress in rabbit isolated corpus cavernosum and in hypertensive rats," *BJU Int.* 103:1522-1529, 2009.
Sidhu et al., "L-cysteine and Sodium Hydrosulphide Inhibit Spontaneous Contractility in Isolated Pregnant Rat Uterine Strips in Vitro." *Pharmacol Toxicol.* 88(4); 198-203, 2001(abstract only).
Sies, "Glutathione and its role in cellular functions," *Free Radic. Biol. Med.* 27:916-921, 1999 (Abstract only).
Simon et al., "Hemodynamic and metabolic effects of hydrogen sulfide during porcine ischemia/reperfusion injury," *Shock* 30:359-364, 2008 (Abstract only).
Simon et al., "Sperm DNA damage measured by the alkaline Comet assay as an independent predictor of male infertility and in vitro fertilization success," *Fertility and Sterility*, 95; 652-657, 2011.
Singh et al., "Garlic Constituent Diallyl Trisulfide Prevents Development of Poorly-Differentiated Prostate Cancer and Pulmonary Metastasis Multiplicity in TRAMP Mice," *Cancer Res.* 68:9503-9511, 2008.
Singh et al., "Sulforaphane-induced Cell Death in Human Prostate Cancer Cells is Initiated by Reactive Oxygen Species," *The Journal of Biological Chemistry* 280:19911-19924, 2005.
Sodha et al., "Hydrogen Sulfide Therapy Attenuates the Inflammatory Response in a Porcine Model of Myocardial Ischemia—Reperfusion Injury," *J Thorac Cardiovasc Surg.* 138:977-984, 2009.
Sontakke et al., "A duality in the roles of reactive oxygen species with respect to bone metabolism," *Clin. Chim. Acta.* 318:145-148, 2002 (Abstract only).
Sörbo, "Mechanism of Oxidation of Inorganic Thiosulfate and Thiosulfate Esters in Mammals," *Acta. Chem. Scand.* 18:821-823, 1964.
Sowers et al., "Calcific uremic arteriolopathy: Pathophysiology, reactive oxygen species and therapeutic approaches," *Oxidative Medicine and Cellular Longevity* 3:109-121, 2010.

(56) References Cited

OTHER PUBLICATIONS

Sowmya et al., "Hydrogen sulfide: regulatory role on blood pressure in hyperhomocysteinemia," *Vascul Pharmacol* 53:138-143, 2010 (Abstract only).

Sparatore et al., "Pharmacological Profile of a Novel H(2)S-Releasing Aspirin," *Free Radic Biol Med* 46:586-592, 2009 (abstract only).

Sparatore et al., "Therapeutic potential of new hydrogen sulfide-releasing hybrids," *Expert Rev. Clin. Pharmacol.* 4:109-121, 2011.

Spiller et al., "Hydrogen Sulfide Improves Neutrophil Migration and Survival in Sepsis via $K^+_{ATP}$ Channel Activation," *Am J Respir Crit Car Med* 182:360-368, 2010.

Srilatha et al., "Hydrogen sulphide: a novel endogenous gasotransmitter facilitates erectile function," *J Sex Med* 4:1304-1311, 2007 (Abstract only).

Srilatha et al., "Initial characterization of hydrogen sulfide effects in female sexual function," *J Sex Med* 6:1875-1884, 2009 (Abstract only).

Srilatha et al., "Possible Role for the Novel Gasotransmitter Hydrogen Sulphide in Erectile Dysfunction—a Pilot Study," *Eur J Pharmacol* 535:280-282, 2006 (abstract only).

Srivastava et al., "Cell cycle arrest, apoptosis induction and inhibition of nuclear factor kappa B activation in anti-proliferative activity of benzyl isothiocyanate against human pancreatic cancer cells," *Carcinogenesis* 25:1701-1709, 2004.

Stasko et al., "Electron transfer: a primary step in the reactions of sodium hydrosulphide, an H2S/HS(−) donor," *Free Radic. Res.* 43:581-593, 2009 (Abstract only).

Steudel, "Mechanism for the Formation of Elemental Sulfur from Aqueous Sulfide in Chemical and Microbiological Desulfurization Processes," *Ind. Eng. Chem. Res.* 35:1417-1423, 1996.

Steudel, "The Chemistry of Organic Polysulfanes R-Sn-R (n>2)," *Chem. Rev.* 102:3905-3945, 2002.

Stipanuk, "Sulfur amino acid metabolism: pathways for production and removal of homocysteine and cysteine," *Annu Rev Nutr* 24:539-577, 2004 (Abstract only).

Stipanuk et al., "Characterization of the enzymic capacity for cysteine desulphhydration in liver and kidney of the rat," *Biochem. J.* 206:267-277, 1982.

Stoyanovsky et al., "Assessments of Thiyl Radicals in Biosystems: Difficulties and New Applications," *Anal. Chem.* 83:6432-6438, 2011.

Suzuki et al., "Increased oxidized form of human serum albumin in patients with diabetes mellitus," *Diabetes Res Clin Pract* 18:153-158, 1992 (Abstract only).

Sykiotis et al., "The role of the antioxidant and longevity-promoting Nrf2 pathway in metabolic regulation," *Curr. Opin. Clin. Nutr. Metab. Care.* 14:41-48, 2011.

Tan et al., "Diabetic Downregulation of Nrf2 Activity via ERK Contributes to Oxidative Stress-Induced Insulin Resistance in Cardiac Cells In Vitro and In Vivo," *Diabetes* 60:625-633, 2011.

Tan et al., "Hydrogen sulfide: a novel signaling molecule in the central nervous system," *Neurochem Int* 56:3-10, 2010 (Abstract only).

Tanaka et al., "NF-E2-Related Factor 2 Inhibits Lipid Accumulation and Oxidative Stress in Mice Fed a High-Fat Diet," *The Journal of Pharmacology and Experimental Therapeutics* 325:655-664, 2008.

Tanaka et al., "Prevention of Glucose Toxicity in HIT-T15 Cells and Zucker Diabetic Fatty Rats by Antioxidants," *Proc. Natl. Acad. Sci. USA*, 96:10857-10862, 1999.

Tang et al., "Interaction of hydrogen sulfide with ion channels," *Clin Exp Pharmacol Physiol* 37:753-763, 2010 (Abstract only).

Taniguchi et al., "Hydrogen sulphide protects mouse pancreatic β-cells from cell death induced by oxidative stress, but not by endoplasmic reticulum stress," *British Journal of Pharmacology* 162:1171-1178, 2011.

Taniguchi et al., "Significance of Hydrogen Sulfide Production in the Pancreatic β-Cell," *J Pharmacol. Sci.* 116:1-5, 2011.

Tatjana et al., "Redox regulation of mitochondrial sulfide oxidation in the lugworm, *Arenicola marina*," *The Journal of Experimental Biology*, 211; 2617-2623, 2008.

Tay et al., "Hydrogen sulfide protects neurons against hypoxic injury via stimulation of ATP-sensitive potassium channel/protein kinase C/extracellular signal-regulated kinase/heat shock protein 90 pathway," *Neuroscience* 167:277-286, 2010 (Abstract only).

Terawaki et al., "The Redox State of Albumin and Serious Cardiovascular Incidence in Hemodialysis Patients," *Therapeutic Apheresis and Dialysis* 14(5):465-471, 2010.

Tiong et al., "Protective Effect of Hydrogen Sulphide Against 6-OHDA-Induced Cell Injury in SH-SY5Y Cells Involves PKC/PI3K/Akt Pathway," *British Journal of Pharmacology*, 161; 467-480, 2010.

Tiranti et al., "Loss of ETHE1, a Mitochondrial Dioxygenase, Causes Fatal Sulfide Toxicity in Ethylmalonic Encephalopathy," *Nat Med*, 15; 200-5, 2009 (abstract only).

Tirouvanziam et al., "High-dose oral N-acetylcysteine, a glutathione prodrug, modulates inflammation in cystic fibrosis," *PNAS* 103:4628-4633, 2006.

Tomida et al., "Observation for the Redox State of Human Synovial Fluid Albumin from Patients with Temporomandibular Joint Disorders," *Acta Scholae Medicinalis Universitatis in Gifu*, 51:21-28, 2003.

Toohey, "Persulfide Sulfur is a Growth Factor for Cells Defective in Sulfur Metabolism," *Biochem Cell Biol* 64:758-765, 1986 (abstract only).

Toohey, "Sulphane sulphur in biological systems: a possible regulatory role," *Biochem. J.* 264:625-632, 1989.

Toombs et al., "Detection of exhaled hydrogen sulphide gas in healthy human volunteers during intravenous administration of sodium sulphide," *British Journal of Clinical Pharmacology* 69:626-636, 2010.

Townsend et al., "The importance of glutathione in human disease," *Biomed Pharmacother.* 57(3-4):145-155, 2003 (Abstract only).

Trachootham et al., "Redox Regulation of Cell Survival," *Antioxidants & Redox Signaling*, 10; 1343-1374, 2008.

Trachootham et al., "Selective killing of oncogenically transformed cells through a ROS-mediated mechanism β-phenylethyl isothiocyanate," *Cancer Cell*, 10;241-252, 2006.

Trapp et al., "Redox-Related Antimelanoma Activity of ATN-224," *Melanoma Res.*, 19; 350-360, 2009 (abstract only).

Trelle et al., "Cardiovascular safety of non-steroidal anti-inflammatory drugs: network meta-analysis," *BMJ* 342:c7086, 2011.

Tsai et al., "*s*-Ethyl Cysteine and *s*-Propyl Cysteine Alleviate β-Amyloid Induced Cytotoxicity in Nerve Growth Factor Differentiated PC12 Cells," *J. Agric. Food Chem.* 58:7104-7108, 2010.

Tsang et al., "Myocardial postconditioning: reperfusion injury revisited," *Am. J. Physiol. Heart Circ. Physiol.* 289:H2-H7, 2005.

Twigg et al., "Analysis of the impact of intracellular reactive oxygen species generation on the structural and functional integrity of human spermatozoa: lipid peroxidation, DNA fragmentation and effectiveness of antioxidants," *Human Reproduction* 13:1429-1436, 1998.

Tyagi et al., "H2S Protects Against Methionine-Induced Oxidative Stress in Brain Endothelial Cells," *Antioxidants & Redox Signaling* 11:25-33, 2009.

Tyagi et al., "Hydrogen sulfide mitigates matrix metalloproteinase-9 activity and neurovascular permeability in hyperhomocysteinemic mice," *Neurochem Int* 56:301-307, 2010.

Ubuka, "Assay methods and biological roles of labile sulfur in animal tissues," *J. Chromatogr. B. Analyt. Technol. Biomed. Life Sci.* 781:227-249, 2002 (Abstract only).

Ueno et al., "Dietary Glutathione Protects Rats from Diabetic Nephropathy and Neuropathy," *Journal of Nutrition* 132:897-900, 2002.

Umemura et al., "Hydrogen sulfide enhances reducing activity in neurons: neurotrophic role of H2S in the brain?," *Antioxid Redox Signal* 9(11):2035-2041, 2007 (Abstract only).

Urig et al., "On the potential of thioredoxin reductase inhibitors for cancer therapy," *Semin Cancer Biol.* 16(6):452-465, 2006 (Abstract only).

Uthus et al., "Methionine flux to transsulfuration is enhanced in the long living Ames dwarf mouse," *Mech Ageing Dev.* 127(5):444-450, 2006.

Vaidya et al., "Garlic: Source of the Ultimate Antioxidants-Sulfenic Acids," *Angew. Chem.* 121:163-166, 2009.

(56) References Cited

OTHER PUBLICATIONS

Vannini et al., "The synthetic oleanane triterpenoid, CDDO-methyl ester, is a potent antiangiogenic agent," *Molecular Cancer Therapeutics* 6:3139-3146, 2007.
Verhagen et al., "Balneotherapy for osteoarthritis," *Cochrane Database Syst Rev.* (4):CD006864, 2007 (Abstract only).
Villarejo et al., "Mechanism of Rhodanese Catalysis of Thiosulfate-Lipoate Oxidation-Reduction," *The Journal of Biological Chemistry* 238:4016-4020, 1963.
Vinten-Johansen et al., "The multidimensional physiological responses to postconditioning," *Antioxid Redox Signal* 14(5):791-810, 2010 (Abstract only).
Viscomi et al., "Combined treatment with oral metronidazole and N-acetylcysteine is effective in ethylmalonic encephalopathy," *Nat Med.* 16(8):869-871, 2010 (Abstract only).
Wagner et al., "Bench-to-bedside review: Hydrogen sulfide—the third gaseous transmitter: applications for critical care," *Critical Care* 13:213, 2009.
Wakabayashi et al., "Protection against electrophile and oxidant stress by induction of the phase 2 response: fate of cysteines of the Keap1 sensor modified by inducers," *Proc. Natl. Acad. Sci. U.S.A.* 101:2040-2045, 2004.
Wakabayashi et al., "When NRF2 Talks, Who's Listening?," *Antioxidants & Redox Signaling* 13:1649-1663, 2010.
Wallace, "Hydrogen sulfide-releasing anti-inflammatory drugs," *Trends Pharmacol. Sci.* 28:501-505, 2007.
Wallace, "Physiological and pathophysiological roles of hydrogen sulfide in the gastrointestinal tract," *Antioxid Redox Signal* 12(9):1125-1133, 2010 (Abstract only).
Wallace, "Prostaglandins, NSAIDs, and Gastric Mucosal Protection: Why Doesn't the Stomach Digest Itself?," *Physiol Rev* 88:1547-1565, 2008.
Wallace et al., "Endogenous and exogenous hydrogen sulfide promotes resolution of colitis in rats," *Gastroenterology* 137(2):569-578, 2009 (Abstract only).
Wallace et al., "Hydrogen sulfide enhances ulcer healing in rats," *The FASEB Journal* 21:4070-4076, 2007.
Wallace et al., "Markedly reduced toxicity of a hydrogen sulphide-releasing derivative of naproxen (ATB-346)," *British Journal of Pharmacology* 159:1236-1246, 2010.
Wang et al., "Allyl Sulfides Inhibit Cell Growth of Skin Cancer Cells through Induction of DNA Damage Mediated G2/M Arrest and Apoptosis," *J. Agric. Food Chem.* 58:7096-7103, 2010.
Wang et al., "Essential Roles of the PI3 Kinase/Akt Pathway in Regulating Nrf2-Dependent Antioxidant Functions in the RPE," *Invest Ophthalmol Vis Sci* 49(4):1671-1678, 2008.
Wang et al., "Hydrogen sulfide and asthma," *Exp Physiol* 96:847-852, 2011.
Wang et al., "Hydrogen sulfide attenuates cardiac dysfunction in a rat model of heart failure: a mechanism through cardiac mitochondrial protection," *Biosci. Rep.* 31: 87-98, 2011.
Wang et al., "Mechanisms of angiogenesis: role of hydrogen sulphide," *Clin Exp Pharmacol Physiol* 37(7):764-771, 2010 (Abstract only).
Wang et al., "Pyruvate Released by Astrocytes Protects Neurons from Copper-Catalyzed Cysteine Neurotoxicity," *The Journal of Neuroscience*, 21; 3322-3331, 2001.
Wang et al., "S-propargyl-cysteine protects both adult rat hearts and neonatal cardiomyocytes from ischemia/hypoxia injury: the contribution of the hydrogen sulfide-mediated pathway," *J Cardiovasc Pharmacol.* 54(2):139-146, 2009 (Abstract only).
Wang et al., "Susceptibility of *Helicobacter pylori* with diversified genotypes to allitridi," *World Chin J Digestol* 12(10): 2325-2328, 2004 (Abstract only).
Warenycia et al., "Dithiothreitol liberates non-acid labile sulfide from brain tissue of H2S-poisoned animals," *Arch Toxicol* 64(8):650-655, 1990 (Abstract only).
Watanabe et al., "Nutritional therapy of chronic hepatitis by whey protein (non-heated)," *J Med* 31(5-6):283-302, 2000 (Abstract only).
Weissmann, "It's Complicated: Inflammation from Metchnikoff to Meryl Streep," *The FASEB Journal* 11:4129-4132, 2010.
Whiteman et al., "Adiposity is a major determinant of plasma levels of the novel vasodilator hydrogen sulphide," *Diabetologia* 53(8):1722-1726, 2010 (Abstract only).
Whiteman et al., "Hydrogen sulphide: a novel inhibitor of hypochlorous acid-mediated oxidative damage in the brain?," *Biochem Biophys Res Commun.* 326(4):794-798, 2005 (Abstract only).
Whiteman et al., "The Effect of Hydrogen Sulfide Donors on Lipopolysaccharide-Induced Formation of Inflammatory Mediators in Macrophages," *Antioxidants & Redox Signaling* 12:1147-1154, 2010.
Whiteman et al., "The novel neuromodulator hydrogen sulfide: an endogenous peroxynitrite 'scavenger'?," *Journal of Neurochemistry* 90:765-768, 2004.
Whitfield et al., "Reappraisal of H2S/sulfide concentration in vertebrate blood and its potential significance in ischemic preconditioning and vascular signaling," *Am J Physiol Regul Integr Comp Physiol* 294:R1930-R1937, 2008.
Williams et al., "Implications of dibenzyl trisulphide for disease treatment based on its mode of action," *West Indian Med J* 58(5):407-409, 2009 (Abstract only).
Winterbourn, "Superoxide as an intracellular radical sink," *Free Radic Biol Med* 14:85-90, 1993 (Abstract only).
Wondrak, "Redox-Directed Cancer Therapeutics: Molecular Mechanisms and Opportunities," *Antioxidants & Redox Signaling* 11:3013-3069, 2009.
Wu et al., "Apoptosis induction in human lung adenocarcinoma cells by oil-soluble allyl sulfides: triggers, pathways, and modulators," *Environ Mol Mutagen.* 50(3):266-275, 2009 (Abstract only).
Wu et al., "Benzyl isothiocyanate (BITC) and phenethyl isothiocyanate (PEITC) mediated generation of reactive oxygen species causes cell cycle arrest and induces apoptosis via activation of caspase-3, mitochondria dysfunction and nitric oxide (NO) in human osteogenic sarcoma U-2 OS cells," *J Orthop Res.* 29(8):1199-1209, 2011 (Abstract only).
Wu et al., "Diallyl trisulfide (DATS) inhibits mouse colon tumor in mouse CT-26 cells allograft model in vivo," *Phytomedicine* 18(8-9):672-676, 2011 (Abstract only).
Wu et al., "Diallyl Trisulfide Modulates Cell Viability and the Antioxidation and Detoxification Systems of Rat Primary Hepatocytes," *The Journal of Nutrition* 134:724-728, 2004.
Wu et al., "Glutathione Metabolism and Its Implications for Health," *Journal of Nutrition* 134:489-492, 2004.
Wu et al., "In Vitro Glutathione Supplementation Enhances Interleukin-2 Production and Mitogenic Response of Peripheral Blood Mononuclear Cells from Young and Old Subjects," *The Journal of Nutrition* 124:655-663, 1994.
Wu et al., "Mechanism of Reduction of Bis(2-hydroxyethyl) Trisulfide by $e_{aq}^-$ and $\cdot CO_2^-$. Spectrum and Scavenging of RSS$\cdot$ Radicals," *J. Phys. Chem.* 86:4417-4422, 1982.
Wu et al., "Targeting ROS: Selective Killing of Cancer Cells by a Cruciferous Vegetable Derived Pro-Oxidant Compound," *Cancer Biology & Therapy* 6:646-647, 2007.
Xia et al., "Production and Actions of Hydrogen Sulfide, a Novel Gaseous Bioactive Substance, in the Kidneys," *The Journal of Pharmocology and Experimental Therapeutics* 329:1056-1062, 2009.
Xiao et al., "Akt Inactivation in DATS-Induced Apoptosis," *Carcinogenesis Advance Access*, Revised Manuscript # Carcin-2005-00511:1-32, 2005.
Xiao et al, "Diallyl trisulfide-induced apoptosis in human prostate cancer cells involves c-Jun N-terminal kinase and extracellular-signal regulated kinase-mediated phosphorylation of Bcl-2," *Oncogene* 22(33):5594-5606, 2004 (Abstract only).
Xiao et al., "Diallyl trisulfide-induced G2-Mphase cell cycle arrest in human prostate cancer cells is caused by reactive oxygen species-dependent destruction and hyperphosphorylation of Cdc25C," *Oncogene* 24:6256-6268, 2005.
Xiao et al., "Diallyl Trisulfide Suppresses Growth of PC-3 Human Prostate Cancer Xenograft In vivo in Association with Bax and Bak Induction," *Clin Cancer Res.* 12:6836-6843, 2006.

(56) References Cited

OTHER PUBLICATIONS

Xiao et al., "Effects of a series of organosulfur compounds on mitotic arrest and induction of apoptosis in colon cancer cells," *Mol Cancer Ther* 4:1388-1398, 2005.

Xiao et al., "Induction of Apoptosis by the Garlic-Derived Compound S-Allylmercaptocysteine (SAMC) Is Associated with Microtubule Depolymerization and c-Jun $NH_2$-Terminal Kinase 1 Activation," *Cancer Research* 63:6825-6837, 2003.

Xiong et al., "S-Glutathionylation: From Molecular Mechanisms to Health Outcomes," *Antioxidants & Redox Signaling* 15:233-270, 2011.

Xu et al., "Hydrogen sulfide protects MC3T3-E1 osteoblastic cells against H2O2-induced oxidative damage-implications for the treatment of osteoporosis," *Free Radical Biol Med* 50(10):1314-1323, 2011 (Abstract only).

Ye et al., "Total intracellular accumulation levels of dietary isothiocyanates determine their activity in elevation of cellular glutathione and induction of Phase 2 detoxification enzymes," *Carcinogenesis* 22:1987-1992, 2001.

Yildiz et al., "L-Cysteine influx and efflux: a possible role for red blood cells in regulation of redox status of the plasma," *Free Radic Res.* 40(5):507-512, 2006 (Abstract only).

Yin et al., "Nonenzymatic Antioxidant Activity of Four Organosulfur Compounds Derived from Garlic," *J. Agric. Food Chem.* 50:6143-6147, 2002.

Yonezawa et al., "A protective role of hydrogen sulfide against oxidative stress in rat gastric mucosal epithelium," *Toxicology* 241(1-2):11-18, 2007 (Abstract only).

Yong et al., "Endogenous hydrogen sulphide mediates the cardioprotection induced by ischemic postconditioning," *Am J Physiol Circ Physiol* 295:H1330-H1340, 2008.

Yong et al., "Sulfide oxidation coupled to ATP synthesis in chicken liver mitochondria," *Comp Biochem Physiol B Biochem Mol Biol.* 129(1):129-137, 2001 (Abstract only).

You et al., "Characterization of a Covalent Polysulfane Bridge in Copper-Zinc Superoxide Dismutase," *Biochemistry* 49:1191-1198, 2010.

Yu et al., "Hydrogen sulfide as an effective and specific novel therapy for acute carbon monoxide poisoning," *Biochem Biophys Res Commun* 404(1)6-9, 2010 (Abstract only).

Yuan et al., "Rescue of mesangial cells from high glucose-induced over-proliferation and extracellular matrix secretion by hydrogen sulfide," *Nephrol Dial Transplant* 26:2119-2126, 2011.

Yusof et al., "Hydrogen sulfide triggers late-phase preconditioning in postischemic small intestine by an NO- and p38 MAPK-dependent mechanism," *Am J Physiol Heart Circ Physiol* 296:H868-H876, 2009.

Zanatta et al., "Synthesis and Preliminary Pharmacological Evaluation of Aryl Dithiolethiones with Cyclooxygenase-2 Selective Inhibitory Activity and Hydrogen-Sulfide-Releasing Properties," *Australian Journal of Chemistry* 63(6):946-957, 2010.

Zeng et al., "Diallyl trisulfide (DATS) effectively attenuated oxidative stress-mediated liver injury and hepatic mitochondrial dysfunction in acute ethanol-exposed mice," *Toxicology* 252(1-3):86-91, 2008 (Abstract only).

Zhang, "The Nrf2-Keap1-ARE signaling pathway: The regulation and dual function of Nrf2 in cancer," *Antioxid Redox Signal* 13(11):1623-1626, 2010 (Abstract only).

Zhang et al., "Allitridum mimics effect of ischemic preconditioning by activation of protein kinase C," *Acta Pharmacol Sin* 22(2):132-136, 2001.

Zhang et al., "Benzyl Isothiocyanate-Induced DNA Damage Causes $G_2/M$ Cell Cycle Arrest and Apoptosis in Human Pancreatic Cancer Cells," *The Journal of Nutrition* 136:2728-2734, 2006.

Zhang et al., "Hydrogen sulfide attenuates neuronal injury induced by vascular dementia via inhibiting apoptosis in rats," *Neurochem Res* 34(11):1984-1992, 2009 (Abstract only).

Zhang et al., "Hydrogen sulfide reduces mRNA and protein levels of β-site amyloid precursor protein cleaving enzyme 1 in PC12 cells," *Neurochem Int* 58(2):169-175, 2010 (Abstract only).

Zhao et al., "Hydrogen sulfide inhibits macrophage-derived foam cell formation," *Experimental Biology and Medicine* 236:169-176, 2011.

Zhao et al., "Sulforaphane protects liver injury induced by intestinal ischemia reperfusion through Nrf2-ARE pathway," *World Journal of Gastroenterology* 16(24):3002-3010, 2010.

Zheng et al., "Study on the long-time effect on allitridum and selenium in prevention of digestive system cancers," *Zhonghua Liu Xing Bing Xue Za Zhi* 26(2):110-112, 2005 (Abstract only).

Zhu et al., "Hydrogen Sulfide in the Endocrine and Reproductive Systems," *Expert Rev. Clin. Pharmacol.* 4:75-82, 2011.

Zhukovskii, "Balneotherapy at the early posthospital stage in the rehabilitative treatment of patients who have had an acute myocardial infarct," *Vopr Kurortol Fizioter Lech Fiz Kult* 6:4-7, 1989 (Abstract only).

Zini et al., "Antioxidants and sperm DNA damage: a clinical perspective," *J Assist Reprod Genet* 26:427-432, 2009.

Zoccali et al., "Blood pressure control: hydrogen sulfide, a new gasotransmitter, takes stage," *Nephrol. Dial. Transplant.* 24:1394-1396, 2009.

Zoghbi et al., "The genus *Mansoa* (Bignoniaceae): a source of organosulfur compounds," *Brazilian Journal of Pharmacognosy* 19(3):795-804, 2009.

Zöphel et al., "Investigations on microbial sulfur respiration," *Arch Micriobiol* 150:72-77, 1988.

Zunnonov, "Clinical efficiency and tolerance of hydrogen sulfide balneotherapy in hypertensive patients living in arid zone," *Ter Arkh.* 75(8):32-35, 2003 (Abstract only).

Zunnunov, "Efficacy and safety of hydrogen sulfide balneotherapy in ischemic heart disease the arid zone," *Ter Arkh* 76(8):15-18, 2004 (Abstract only).

Zunnunov, "Potentiation of anti-ischemic and anti-anginal action of nitrates by hydrogen sulfide balneotherapy in patients with angina of effort," *Vopr Kurortol Fizioter Lech Fiz Kult* 1:11-14, 2010 (Abstract only).

FIG. 13A
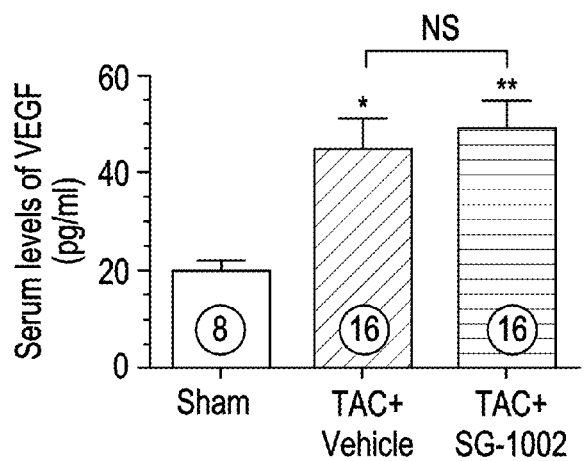
FIG. 13B
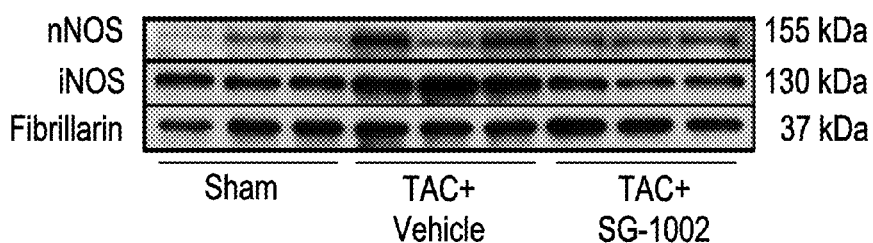
FIG. 13C  FIG. 13D
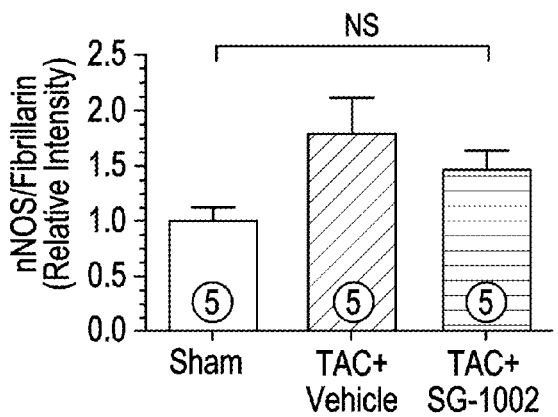 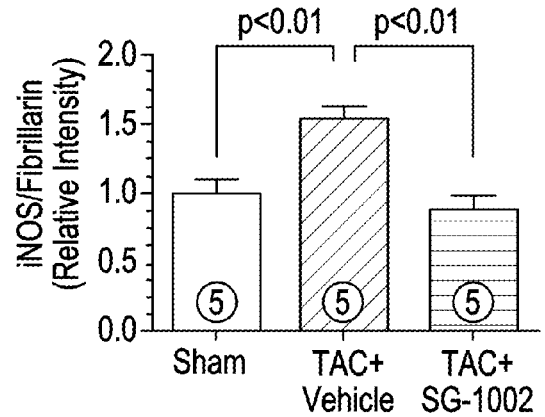

HYDROGEN SULFIDE IN HEART FAILURE

PREPARATION AND COMPOSITIONS OF HIGHLY BIOAVAILABLE ZEROVALENT SULFUR AND USES THEREOF

CROSS-REFERENCE TO RELATED APPLICATIONS

This application claims benefit of U.S. Provisional Application No. 61/534,585, filed Sep. 13, 2011, which is hereby incorporated by reference.

BACKGROUND OF THE INVENTION

In general, the invention features zerovalent-sulfur-rich compositions and methods of preparation, formulation, and prevention and treatment of pathological conditions associated with oxidative stress.

Despite the abundance of medications to lower blood pressure, reduce cholesterol, and treat cardiovascular conditions, cardiovascular disease remains the number one killer in the United States. The incidence of cardiovascular problems is likely to continue its steady rise as the "Baby Boomer" generation ages and as obesity and diabetes rates continue to rise. Therefore, development of better therapies is of utmost importance.

Hydrogen sulfide ($H_2S$) is a recognized endogenous signaling molecule that has been shown to modulate immune and mitochondrial function, act both directly and indirectly as an antioxidant, and increase blood flow by a variety of mechanisms. In addition, hydrogen sulfide is a potent anti-inflammatory agent and modulator of cell death. This plethora of properties makes hydrogen sulfide an ideal candidate for the treatment of cardiovascular disease, cancers, inflammatory disease, diabetes, dyslipidemia, neurodegenerative disease, AIDS, and other pathological conditions associated with oxidative stress, an imbalance in redox homeostasis, and/or immune dysfunction.

Whereas the main physiological roles of $H_2S$ are in signaling and cytoprotection in normal (i.e., non-transformed) cells and tissues, it is now clear that in transformed (i.e., malignant) cells, $H_2S$ displays prooxidant and proapoptotic effects. These effects constitute the basis for developing a novel therapeutic and/or prophylactic approach to treat conditions associated with uncontrolled cell growth such as cancer and other hyperproliferative diseases.

Hydrogen sulfide is produced endogenously from cysteine by the enzymes cystathionine beta-synthase, cystathionine gamma-lyase, and 3-mercaptopyruvate sulfurtransferase. Hydrogen sulfide prodrugs can provide an exogenous source for hydrogen sulfide in the body, however, currently used hydrogen sulfide prodrugs contain no more than 57% bioactive sulfur (sulfur capable of being converted into hydrogen sulfide in vivo). On the other hand, it has become increasingly clear that sodium hydrogen sulfide (NaHS, also known as sodium hydrosulfide), which contains 57% bioactive sulfur, releases hydrogen sulfide in a sudden and uncontrolled manner when injected into the body of a mammal, whereas it is highly unlikely that cells or tissues are ever exposed to $H_2S$ generated in such manner. Therefore, there is a need to identify hydrogen sulfide prodrugs that are safe and effective, are active when orally administered, release $H_2S$ in a controlled and sustained manner, and have high bioavailability for treatment of cardiovascular disease, cancer, inflammatory disease, diabetes, dyslipidemia, neurodegenerative disease, AIDS, and other pathological conditions associated with oxidative stress, an imbalance in redox homeostasis, and/or immune dysfunction.

SUMMARY OF THE INVENTION

The invention features a composition including 90-99.9% (w/w) elemental alpha sulfur and 0.01-10% (w/w) highly polar components. In certain embodiments, the composition can optionally include one or more pharmaceutically acceptable excipients. In other embodiments, the composition can include about 99% (w/w) zerovalent sulfur and about 1% (w/w) highly polar components, wherein the highly polar components are selected from sodium sulfate, sodium polythionates, and sodium thiosulfate.

The invention also features a composition including an elemental alpha sulfur and one or more highly polar components in a ratio from about 10 to about 150 parts elemental alpha sulfur to 1 part highly polar components (w/w) for enteral, topical, or parenteral administration. In certain embodiments, the ratio of elemental alpha sulfur to highly polar components is 15:1, 20:1, 30:1, 35:1, 40:1, 45:1, 50:1, 55:1, 60:1, 70:1, 80:1, 90:1, 100:1, 110:1, 120:1, 130:1, 140:1, or 145:1.

In some embodiments, a composition of the invention is formulated for enteral administration and the elemental alpha sulfur and the highly polar components are present together in an amount of 400 mg. In one aspect of the embodiment, the composition is a capsule.

In other embodiments, a composition of the invention is formulated for topical administration, and the composition includes 1-20% zerovalent sulfur content. In one aspect of the embodiment, the composition is a cream. In one aspect, the cream includes (i) 5-20% zerovalent sulfur content and (ii) polyethylene glycol or petroleum jelly. In another aspect, the cream includes 5-15% zerovalent sulfur content. In certain embodiments, the cream includes 2%, 3%, 4%, 5%, 6%, 7%, 8%, 9%, 10%, 11%, 12%, 13%, 14%, 15%, 16%, 17%, 18%, or 19% zerovalent sulfur content.

For any of the above compositions, the highly polar components can be selected from the group consisting of sodium polythionate, potassium polythionate, ammonium polythionate, calcium polythionate, sodium thiosulfate, potassium thiosulfate, ammonium thiosulfate, calcium thiosulfate, sodium sulfate, potassium sulfate, ammonium sulfate, sodium bisulfite, potassium bisulfite, ammonium bisulfite, calcium bisulfite, sodium chloride, potassium chloride, ammonium chloride, calcium chloride, sodium acetate, sodium palmitate, potassium palmitate, and ammonium laurate.

In certain embodiments, the compositions of the invention further include a third agent. In some embodiments, the third agent is a cardiovascular disease drug, an anti-inflammatory drug, an anti-neurodegenerative drug, or an anticancer/antiproliferative drug. In other embodiments, the third agent is a dietary supplement. In certain aspects of the invention the elemental alpha sulfur, the highly polar components, and the third agent are present in an effective amount to treat a condition associated with oxidative stress. In other aspects, the elemental alpha sulfur, the highly polar components, and the third agent are present in an effective amount to promote or maintain general health.

The invention also features a method for preparing a composition including 90-99.9% (w/w) elemental alpha sulfur and 0.01-10% (w/w) highly polar components, the method includes: (a) providing a first inorganic compound including sulfur in the $^-2$ (minus two) oxidation state, (b) reacting the first inorganic compound with a second compound including sulfur in the $^{+}4$ (plus four) oxidation state and optionally an acid, wherein the reacting produces a composition including 90-99.9% (w/w) elemental alpha sulfur and 0.01-10% (w/w) highly polar components.

In one embodiment, the first inorganic compound is sodium hydrogen sulfide or sodium sulfide. In a second embodiment, the second inorganic compound is sodium metabisulfite, sodium bisulfite, or sodium sulfite. In a third embodiment, the acid is concentrated sulfuric acid.

The invention also features a method of treating a condition associated with oxidative stress in a subject in need thereof by administering an effective amount of a composition including 90-99.9% (w/w) elemental alpha sulfur and 0.01-10% (w/w) highly polar components, and optionally including one or more pharmaceutically acceptable excipients. In certain aspects, the composition can also include about 99% (w/w) zerovalent sulfur and about 1% (w/w) highly polar components, wherein the highly polar components are selected from sodium sulfate, sodium polythionates, and sodium thiosulfate.

In another aspect, the invention also features a method of treating a condition associated with oxidative stress in a subject in need thereof by administering an effective amount of a composition including an elemental alpha sulfur and one or more highly polar components in a ratio from about 10 to about 150 parts elemental alpha sulfur to 1 part highly polar components (w/w) for enteral, topical, or parenteral administration.

In some embodiments, the condition associated with oxidative stress is selected from the group consisting of: schizophrenia, bipolar disorder, fragile X syndrome, sickle cell disease, chronic fatigue syndrome, osteoarthritis cataract, macular degeneration, toxic hepatitis, viral hepatitis, cirrhosis, chronic hepatitis, oxidative stress from dialysis, renal toxicity, kidney failure, ulcerative colitis, bacterial infection, viral infections, such as HIV and AIDS, herpes, ear infection, upper respiratory tract diseases, hypertension, balding and hair loss, male infertility, over-training syndrome related to athletic performance, athlete's foot, psoriases, eczema, scleroderma, atopic dermatitis, polymyositis, rosacea, dermatitis herpetiformis, other neurodegenerative diseases, other inflammatory disease, and a cancer.

In other embodiments, the condition associated with oxidative stress is a cardiovascular disease. In certain aspects of the embodiment, the cardiovascular disease is selected from the group consisting of: arteriosclerosis, coronary heart disease, ischemia, endothelium dysfunction, in particular those dysfunctions affecting blood vessel elasticity, restenosis, thrombosis, angina, high blood pressure, cardiomyopathy, hypertensive heart disease, heart failure, cor pulmonale, cardiac dysrhythmias, endocarditis, inflammatory cardiomegaly, myocarditis, myocardial infarction, valvular heart disease, stroke and cerebrovascular disease, aortic valve stenosis, congestive heart failure, and peripheral arterial disease.

The invention also features a method of increasing hydrogen sulfide levels in a subject having a sulfur nutritional deficiency by administering an effective amount of a composition including 90-99.9% (w/w) elemental alpha sulfur and 0.01-10% (w/w) highly polar components, and optionally including one or more pharmaceutically acceptable excipients.

In one aspect, the invention also features a method for assessing the treatment of a cardiovascular disease by administering a composition including 90-99.9% (w/w) elemental alpha sulfur and 0.01-10% (w/w) highly polar components, and optionally including one or more pharmaceutically acceptable excipients. The method includes the steps of: determining the level of hydrogen sulfide in a sample from the subject, adjusting the dose of the composition in an amount sufficient to treat the cardiovascular disease, wherein an increase in the level of hydrogen sulfide or an improvement in a cardiovascular parameter results in the treatment of the cardiovascular disease. In certain aspects, the cardiovascular parameter is selected from the group consisting of end-diastolic volume (EDV), end-systolic volume (ESV), stroke volume, ejection fraction, heart rate, and cardiac output.

DEFINITIONS

By "elemental alpha sulfur" is meant orthorhombic elemental sulfur having the formula $S_8$. Elemental alpha sulfur exists as $S_8$ (cyclooctasulfur molecules), but can also include $S_7$ (cycloheptasulfur molecules) and $S_6$ (cyclohexasulfur molecules).

By "elemental beta sulfur" is meant monoclinic elemental sulfur having the formula $S_8$ and consisting mainly of cyclooctasulfur molecules.

By "highly polar component" is meant a compound whose molecules contain at least one ionic bond or one highly polar covalent bond. Highly polar components include, e.g., sodium polythionates, potassium polythionates, ammonium polythionates, calcium polythionates, sodium thiosulfate, potassium thiosulfate, ammonium thiosulfate, calcium thiosulfate, sodium sulfate, potassium sulfate, ammonium sulfate, sodium bisulfite, potassium bisulfite, ammonium bisulfite, calcium bisulfite, sodium chloride, potassium chloride, ammonium chloride, calcium chloride, sodium acetate, sodium palmitate, potassium palmitate, and/or ammonium laurate. Highly polar components also include molecules containing highly polar O—H covalent bonds, e.g., water, alcohols, polyols, polythionic acids, carboxylic acids, and/or sorbitan monostearate. Highly polar components further include compounds whose molecules contain highly polar N—H covalent bonds, for example, primary amines, amino acids, primary amides, peptides and proteins.

By "polythionate" is meant an anion or group of the formula $^{-O}_3S$—$S_n SO_3^-$ (e.g., where n is an integer from 1 to 60, preferably from 1-20, and more preferably 1, 2, 3, 4, 5, or 6).

By "zerovalent sulfur" is meant a sulfur atom with an oxidation state of zero, as calculated according to an agreed-upon set of rules well known to a person skilled in the art (e.g., each cyclooctasulfur molecule ($S_8$) contains eight zerovalent sulfur atoms, each thiosulfate ion ($S_2O_3^{-2}$) contains one zerovalent sulfur atom, and each polythionate ion contains "n" zerovalent sulfur atoms. Zerovalent sulfur can be found in sulfane sulfur compounds.

By "zerovalent sulfur content" is meant the amount of zerovalent sulfur present in a composition containing elemental alpha sulfur and highly polar components, such as, sodium polythionates, potassium polythionates, ammonium polythionates, calcium polythionates, sodium thiosulfate, potassium thiosulfate, ammonium thiosulfate, calcium thiosulfate, sodium sulfate, potassium sulfate, and ammonium sulfate.

By "sulfane sulfur" is meant a labile, highly reactive sulfur atom at a reduced oxidation state with a valence of 0 or −1, covalently bound to another sulfur atom. Sulfane sulfur compounds can include, e.g., persulfides, polysulfides, polythionates, polysulfanes, thiotaurine, thiosulfate, and/or elemental sulfur. Sulfane sulfur compounds can be formed in the anaerobic cysteine sulfur metabolism with the participation of enzymes such as cystathionase, 3-mercaptopyruvate sulfurtransferase, and/or rhodanese. The last step in enzymatic H$_2$S-generating pathways generally involves sulfane sulfur-containing species. Compounds containing sulfane sulfur can participate in cell regulation processes through activation or inactivation of enzymes such as, e.g., oxidoreductase containing an iron or molybdenum atom, e.g., xanthine oxidase, aldehyde oxidase, and malate dehydrogenase).

By "enteral" is meant administration that involves any part of the gastrointestinal tract. Enteral administration can include: by mouth in the form of tablets, capsules, or drops, by gastric feeding tube, duodenal feeding tube, or rectally.

By "topical" is meant administration that is local or systemic, particularly epicutaneous, inhalational, eye drops, and/or ear drops.

By "parenteral" is meant administering the composition of the invention by means other than oral intake, particularly by injection of a form of liquid into the body. Parenteral administration can include: intravenous, intra-arterial, intraosseous infusion, intra-muscular, intracerebral, intracerebroventricular, and subcutaneous administration.

By "cardiovascular disease drug" is meant a class of agents or substances that are used to treat diseases that affect the cardiovascular system, particularly cardiac disease, vascular disease of the brain and kidney, and peripheral arterial disease.

By "anti-inflammatory drug" is meant an agent or substance that act by reducing inflammation.

By "anticancer/anti-proliferative drug" is meant an agent, substance, and/or mixture of substances that reduces, prevents, and/or interferes with the uncontrolled growth of cells, its initiation, promotion, progression, and/or spread to other organs.

By "anti-neurodegenerative drug" is meant an agent, substance, and/or mixture of substances that restores and/or improves neuron function by acting directly on neurons or indirectly on pathways associated with neuronal function (e.g., axonal transport pathways, protein misfolding pathways, protein degradation pathways, and programmed cell death pathways).

By "dietary supplement" is meant an agent, substance, and/or mixture of substances that is a food supplement or nutritional supplement intended to supplement the diet and provide nutrients, such as vitamins, minerals, fiber, fatty acids, or amino acids that may be missing or may not be consumed in sufficient quantities in a person's diet.

By "promote or maintain general health" is meant to aid in accomplishing a state of human health that is characterized by homeostatic balance with the stable condition of properties such as temperature, pH, electrolytes, and/or metabolites.

By "inorganic" is meant a compound that is not an organic compound.

By "oxidation state" is meant a measure of the degree of oxidation of an atom in a molecule of a substance defined as the charge an atom might be imagined to have when electrons are counted according to an agreed-upon set of rules well known to a person skilled in the art.

By "acid" is meant an Arrhenius acid, a Bronsted-Lowry acid, and/or a Lewis acid. An Arrhenius acid is a substance that increases the concentration of the hydronium ion when dissolved in water. A Bronsted-Lowry acid is a species that donates a proton to a Bronsted-Lowry base. A Lewis acid is a species that accepts a pair of electrons from another species.

By "conditions associated with oxidative stress" is meant a condition characterized by or originated from imbalance between the systemic manifestation of reactive oxygen species and a biological system's ability to readily detoxify the reactive intermediates and/or to repair the resulting damage.

By "hydrogen sulfide" is meant a compound having the formula H$_2$S that is produced in small amounts by many cells of the mammalian body and has a number of biological signaling functions (e.g., a relaxant of smooth muscle, a vasodilator, increases response of NMDA receptor, facilitates long term potentiation, and involvement in memory formation).

By "increasing hydrogen sulfide levels" is meant increasing in the level of hydrogen sulfide produced in the mammalian body (e.g., from cysteine by the enzymes cystathionine beta-synthase and cystathionine gamma-lyase) by at least about 5%, 10%, 20%, 30%, 40%, 50%, 60%, 70%, 80%, 90%, or 100% as compared to a control reference sample. Levels of hydrogen sulfide can be determined using any useful methods known in the art.

By "sulfur nutritional deficiency" is meant a condition characterized by an imbalance in enzyme activity, hormone levels, and immune system function due to a lack of sufficient amounts of sulfur in a regular diet. Symptoms of sulfur nutritional deficiency include, for example, impaired hepatic and renal function, fragile nails, shedding of hair, itchy skin or scalp, eczema, acne, diaper rash, migraine headaches, flatulence, indigestion, vomiting, diarrhea, hemorrhoids, impotence, painful and irregular menstruation, frequent episodes of infections of bacterial or viral origin, sore throat, toothache, nosebleeds, measles, joint pain, hay fever, fever, bed wetting, and/or breastfeeding problems.

By "improvement in cardiovascular parameter" is meant a change in a cardiovascular parameter (e.g., end-diastolic volume (EDV), end-systolic volume (ESV), stroke volume, ejection fraction, heart rate, and cardiac output) to normal ranges (e.g., an end-diastolic volume (EDV) from about 65-240 mL, an end-systolic volume (ESV) from about 16-143 mL, a stroke volume from about 55-100 mL, an ejection fraction from about 55-70%, a heart rate from about 60-100 bpm, and/or cardiac output of about 4.0-8.0 L/min).

By "treating" is meant subjecting a patient to a management regimen for the purpose of combating a disease or disorder and obtaining beneficial or desired results, such as clinical results. Beneficial or desired results can include, but are not limited to, improvement in quality of life, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable.

By "subject" is meant a mammal (e.g., a human or a non-human).

By "effective amount" of an agent is meant the amount of the agent sufficient to effect beneficial or desired result (e.g., treatment of cardiovascular diseases, cancers (e.g., malignant cell hyperproliferation), inflammatory diseases, diabetes, dyslipidemia, neurodegenerative diseases, AIDS, and other pathological conditions associated with oxidative stress, an imbalance in redox homeostasis, and/or immune dysfunction), and, as such, an amount of the composition sufficient to achieve an increase in in vivo hydrogen sulfide and/or sulfane sulfur levels, as compared to the level of hydrogen sulfide and/or sulfane sulfur without administration of the composition.

By "composition" is meant a system comprising a substance described herein, optionally formulated with an acceptable excipient, and manufactured or sold with the approval of a governmental regulatory agency as part of a therapeutic regimen for the treatment of disease in a mammal or to promote and maintain general health. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution or colloidal dispersion free of particulate emboli and in a solvent system suitable for intravenous use); or in any other formulation described herein.

By "acceptable excipient" is meant any ingredient other than the substance described herein (for example, a vehicle capable of suspending or dissolving the active substance and/or substances, e.g., petroleum jelly and polyethylene glycol) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, colloid stabilizers, sweeteners, and water. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, ethylcellulose, gelatin, hydroxypropyl cellulose, hydroxypropyl methylcellulose, lactose, magnesium stearate, maltitol, mannitol, methylcellulose, methyl paraben, microcrystalline cellulose, polyethylene glycol, polyvinyl pyrrolidone, povidone, pregelatinized starch, propyl paraben, shellac, silicon dioxide, sodium carboxymethyl cellulose, sodium starch glycolate, sorbitol, starch (corn), stearic acid, sucrose, talc, titanium dioxide, and xylitol. Excipients may also include diluents (e.g., saline and aqueous buffer solutions), aqueous carriers, and nonaqueous carriers, for example, water, ethanol, polyols (such as glycerol, propylene glycol, polyethylene glycol, and the like), and suitable mixtures thereof, vegetable oils, such as olive oil, and injectable organic esters, such as ethyl oleate.

As used herein, the term "about" means±10% of the recited value.

Provided in Table 1 is a list of abbreviations and meanings of terminology described herein.

TABLE 1

| Abbreviation | Meaning |
| --- | --- |
| 3-MST | 3-mercaptopyruvate sulfutransferase |
| ACS6 | $H_2S$-donating derivative of sildenafil |
| ADEM | acute disseminated encephalomyelitis |
| Akt | Protein Kinase B |
| Ak-P$^{Ser473}$ | phosphorylated Akt at serine residue 473 |
| Akt-P$^{Thr308}$ | phosphorylated Akt at threonine residue 308 |
| ALS | amyotrophic lateral sclerosis |
| BHT | butylated hydroxytoluene |
| CBS | cystathionine beta synthase |
| CO | carbon monoxide |
| CRISPs | cysteine-rich-secretory proteins |
| CS-CSE Tg | cardiac specific CSE transgenic mice |
| CSE | cystathionine gamma lyase |
| CSE KO | CSE deficient |
| DADS | diallyl disulfide |
| DATS | diallyl trisulfide |
| DBTS | dibenzyl trisulfide |
| ED | erectile dysfunction |
| EDV | end-diastolic volume |
| eNOS | endothelial nitric oxide synthase |
| eNOS-P$^{Ser1177}$ | eNOS at serine residue 1177 |
| ESV | end-systolic volume |
| FEG | phenylalanine-glutamine-glycine |
| feG | D-isomeric form |
| GSH | glutathione |

TABLE 1-continued

| Abbreviation | Meaning |
| --- | --- |
| $H_2S$ | hydrogen sulfide |
| HO-1 | heme oxygenase 1 |
| IJM | circulating sulfane sulfur levels |
| ImSAIDs | immune selective anti-inflammatory derivatives |
| I/R | ischemia/reperfusion |
| IVSd | intraventricular septal end-diastolic dimension |
| j.JM 02/sec/mg | mitochondrial respiratory function |
| LV | left ventricular |
| LVEDD | left ventricular end-diastolic diameter |
| LVEF | left ventricular ejection fraction |
| LVESD | left ventricular end-systolic diameter |
| MFR | mobile forms recovered |
| NaHS | sodium hydrogen sulfide |
| NO | nitric oxide |
| $NO_2^-$ | nitrite |
| $NO_3^-$ | nitrate |
| NOX | NADPH oxidase |
| Nox4 | NADPH oxidase 4 |
| NSAIDs | non-steroidal anti-inflammatory drugs |
| PDE5 | phosphodiesterase type 5 |
| RCR | respiratory control ratio |
| RCR | respiratory control ratio |
| ROS | reactive oxygen species |
| $S_2O_3^{-2}$ | thiosulfate ion |
| $S_8$ | cyclooctasulfur molecule |
| SG-1002 | highly bioavailable zerovalent-sulfur rich composition |
| TAC | transverse aortic constriction |
| TBZ | 4-hydroxythiobenzamide |
| VEGF | vascular endothelial growth factor |
| WT | wild-type |

BRIEF DESCRIPTION OF THE FIGURES

FIGS. 1A-1D show representative gas chromatograph peaks and summary data of circulating free hydrogen sulfide ($H_2S$) and sulfane sulfur levels in normal controls and heart failure patients. FIGS. 1E-1F show circulating levels of free $H_2S$ and sulfane sulfur after 6 weeks of pressure overload-induced heart failure (TAC) in groups of mice maintained on a standard chow (TAC+Vehicle) or maintained on a chow containing the $H_2S$ donor SG-1002 (TAC+SG-1002, 20 mg/kg/day). FIGS. 1G-1H show myocardial levels of free $H_2S$ and sulfane sulfur in the experimental groups. Results are expressed as mean±SEM. Numbers in bars represent the sample size. $p<0.01$ and *$p<0.001$ vs. Sham.

FIG. 2A is representative heart pictures of wild-type (WT+TAC) mice, CSE deficient (CSE KO+TAC) mice, and CSE KO mice treated with SG-1002 (CSE KO+TAC+SG-1002) at 12 weeks of TAC. FIG. 2B shows the ratio of heart weight/tibia length ratio and lung weight/tibia length at 12 weeks following TAC. FIG. 2C shows intraventricular septal end-diastolic dimension (IVSd in mm). FIG. 2D shows LV end-diastolic diameter (LVEDD in mm), FIG. 2E shows LV end-systolic diameter (LVESD in mm), and FIG. 2F shows LV ejection fraction (%) following TAC. Wall thickness increased similarly in all groups at 1 week up to 12 weeks following TAC. CSE KO mice exhibited dilatation and dysfunction starting at 6 weeks of TAC. WT and CSE KO mice treated with SG-1002 exhibited no significant change in LV dimensions and exhibited preserved cardiac function. Results are expressed as mean±SEM. †$p<0.05$, ‡$p<0.01$ and #$p<0.001$ vs. WT. *$p<0.05$ and ***$p<0.001$ vs. Baseline.

FIG. 3A is representative photomicrographs of wild-type (WT+TAC) and cardiac specific CSE transgenic mice (CS-CSE Tg+TAC) at 12 weeks of TAC. FIG. 3B shows myocardial weights (mg/cm) and lung weights (mg/cm) expressed as ratio of tibia length at 12 weeks of TAC. FIG. 3C shows IVSd (mm), FIG. 3D shows LVEDD (mm), FIG. 3E shows LVESD (mm), and FIG. 3F shows LV ejection fraction (%) following TAC. Wall thickness increased similarly in WT and CSE Tg mice from 1 week to 12 weeks of TAC. CSE Tg mice experienced significantly less dilatation and cardiac dysfunction compared to WT mice. Results are expressed as mean±SEM. $p<0.01$ and *$p<0.001$ vs. Baseline.

FIG. 4A is representative heart pictures of Sham, Vehicle (TAC+Vehicle), and SG-1002 (TAC+SG-1002) treated mice at 12 weeks of TAC. FIG. 4B shows the ratio of heart weight/tibia lengths. FIG. 4C shows the ratio of lung weight/tibia lengths. FIG. 4D shows circulating BNP levels (ng/mL) at 6 and 12 weeks of TAC. FIG. 4E shows IVSd (mm), FIG. 4F shows LVEDD (mm), FIG. 4G shows LVESD (mm), and FIG. 4H shows ejection fraction (%) following TAC. Wall thickness increased similarly in both groups following TAC. However, SG-1002 diet prevented cardiac dilatation and dysfunction starting at 6 weeks of TAC. Results are expressed as mean±SEM. *$p<0.05$, $p<0.01$, and *$p<0.001$ vs. Baseline.

FIG. 5A is representative photomicrographs of Masson's Trichrome and Picrosirius Red stained heart sections depicting intermuscular and perivascular fibrosis in hearts from Sham, TAC+Vehicle, and TAC+SG-1002 treated mice at 6 weeks of TAC. FIG. 5B is a summary of fibrosis area as % of the LV as calculated from Masson's Trichrome sections. FIG. 5C is a summary of fibrosis area as % of the LV calculated from the Picrosirius Red sections. Results are expressed as mean±SEM. $p<0.01$, and *$p<0.001$ vs. Sham.

FIG. 6A is representative immunoblots of total Akt, Akt-$P^{Ser473}$, and Akt-$P^{Thr308}$. FIG. 6B is densitometric analysis of the expression of total Akt. FIG. 6C is densitometric analysis of Akt-$P^{Ser473}$ and Akt-$P^{Thr308}$ in hearts from Sham, TAC+Vehicle, and TAC+SG-1002 at 6 weeks of TAC. FIG. 6D is representative immunoblots and densitometric analysis of cardiac VEGF expression at 6 weeks of TAC. FIGS. 6E-6F are representative immunoblots and densitometric analysis of the expression of total eNOS and eNOS-$P^{Ser1177}$ in hearts from Sham, TAC+Vehicle, and TAC+SG-1002 at 6 weeks of TAC. FIGS. 6G-6H show nitrite and nitrate levels in the hearts of the experimental groups at 6 weeks of TAC. Results are expressed as mean±SEM.

FIG. 7A shows mitochondrial respiratory function (j.JM 02/sec/mg) in State 3 and State 4 in hearts from Sham, TAC+Vehicle, and TAC+SG-1002 at 6 weeks of TAC. FIG. 7B shows the respiratory control ratio (RCR) from the hearts of the experimental groups at 6 weeks of TAC. FIGS. 7C-7D show plasma and heart 8-isoprostane levels at 6 weeks of TAC. FIG. 7E is representative immunoblots and densitometric analysis of NADPH oxidase 4 (Nox4) in hearts of the experimental groups at 6 weeks of TAC. FIG. 7F is representative immunoblots and densitometric analysis of heme oxygenase 1 (HO-1) in hearts of the experimental groups at 6 weeks of TAC Results are expressed as mean±SEM. *$p<0.05$ and ***$p<0.001$ vs. Sham.

FIG. 8A is representative immunoblots of cystathionine gamma lyase (CSE), cystathionine beta synthase (CBS), and 3-mercaptopyruvate sulfutransferase (3-MST) in the hearts of Sham, TAC+Vehicle, and TAC+SG-1002 treated mice at 6 weeks of TAC. FIGS. 8B-8D show densitometric analysis of CSE, CBS, and 3-MST in Sham, TAC+Vehicle, and TAC+SG-1002 groups at 6 weeks following TAC. Results are expressed as mean±SEM. Numbers in bars represent the sample size.

FIG. 9A shows circulating free hydrogen sulfide ($H_2S$) and FIG. 9B shows circulating sulfane sulfur levels (IJM) in wild-type (WT) control, CSE deficient (CSE KO) and CSE KO mice fed a diet containing the $H_2S$ donor SG-1002, FIG. 9C shows free $H_{2S}$ and FIG. 9D shows sulfane sulfur levels (nmol/mg wet weight) in the hearts of WT, CSE KO and CSE KO+SG-1002 mice. Results are expressed as mean±SEM. *$p<0.05$, **$p<0.01$ vs. WT.

FIG. 10A shows Kaplan-Meier survival curves for TAC+WT mice, TAC+CSE KO mice and CSE KO mice fed a SG-1002 diet (TAC+CSE KO+SG-1002) during the 12 week TAC protocol. FIG. 10B shows Kaplan-Meier survival curves for TAC+WT and cardiac-specific CSE transgenic mice (TAC+CS-CSE Tg) following 12 weeks of TAC. FIG. 10C shows Kaplan-Meier survival curves for mice fed a control diet (TAC+Vehicle) and mice fed a SG-1002 diet (TAC+SG-1002) following 12 weeks of TAC.

FIG. 12A shows the intraventricular septum end-diastolic dimension (IVSd, m), FIG. 12B shows the LV end-diastolic diameter (LVEDD, m), FIG. 12C shows the LV end-systolic diameter (LVESD, m), and FIG. 12D shows the LV ejection fraction (%) from treated with SG-1002 for 6 weeks following TAC (SG-1002), mice treated with SG-1002 for 1 week following TAC and then SG-1002 was withdrawn for 5 weeks and mice treated with SG-1002 for 3 weeks following TAC and SG-1002 was withdrawn for 3 weeks. Results are expressed as mean±SEM. *$p<0.05$, ***$p<0.001$ vs. Baseline.

FIGS. 13A-13D. FIG. 13A shows serum levels (pg/mL) of VEGF-A in TAC+Vehicle, and TAC+SG-1002 treated mice at 6 weeks following TAC. FIG. 13B is representative immunoblots for myocardial nNOS and iNOS from the hearts of Sham, TAC+Vehicle, and TAC+SG-1002 treated mice at 6 weeks of TAC. FIG. 13C shows a densitometric analysis of nNOS protein relative to fibrillarin in Sham, TAC+Vehicle, and TAC+SG-1002 hearts. FIG. 13D shows a bar graph of densitometric analysis of myocardial iNOS protein relative to fibrillarin in Sham, TAC+Vehicle, and TAC+SG-1002 mice following 6 weeks of TAC. Results are expressed as mean±SEM. *$p<0.05$, **$p<0.01$ vs. Sham.

DETAILED DESCRIPTION

Figure 1A:
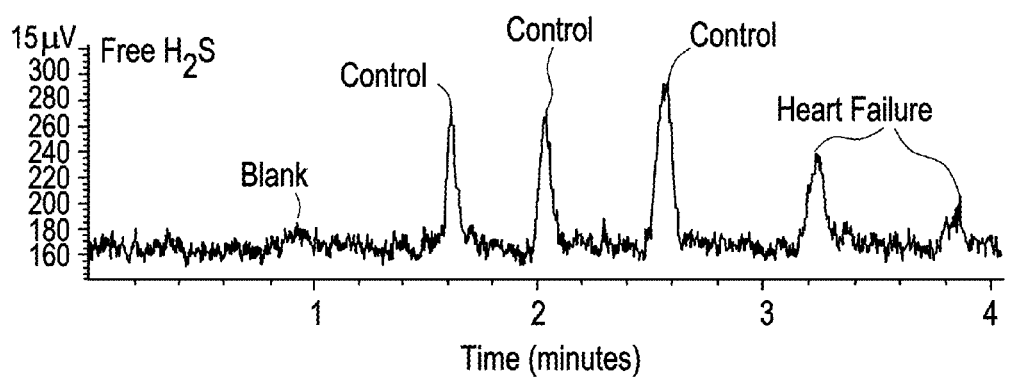
FIGS. 1A-1H are data showing that heart failure reduces sulfide levels in humans and mice.

We have discovered an extraordinarily safe and effective hydrogen sulfide prodrug of high bioavailability. The highly bioavailable zerovalent-sulfur-rich compositions of the invention contain at least 96% bioactive zerovalent sulfur that readily undergoes bioconversion into hydrogen sulfide.

Other currently used hydrogen sulfide precursors contain no more than 57% bioactive sulfur. Table 2 shows the percentage bioactive sulfur contained in several prior art hydrogen sulfide prodrugs and Table 3 shows the effects of hydrogen sulfide in various cancer pathways. We describe herein the preparation and characterization of the highly bioavailable zerovalent sulfur-rich composition and methods of administering the composition to treat and/or prevent cardiovascular disease, cancers, inflammatory disease, diabetes, dyslipidemia, neurodegenerative disease, AIDS, and other pathological conditions associated with oxidative stress, an imbalance in redox homeostasis, and/or immune dysfunction.

TABLE 2

| Hydrogen Sulfide Prodrug | % Bioactive sulfur (w/w) |
|---|---|
| NaHS (anhydrous) | 57 |
| Diallyl trisulfide (DATS) | 53.9 |
| Diallyl disulfide (DADS) | 45.1 |
| $Na_2S$ (anhydrous) | 41 |
| 4-hydroxythiobenzamide (TBZ) | 20.9 |
| Sulforaphane (an isothiocyanate, from broccoli) | 18 |
| Anethole trithione (a dithiolethione) | 13.3 |
| Dibenzyl trisulfide (DBTS) | 11.5 |
| ATB 346 (a naproxen-TBZ conjugate) | 8.8 |
| GYY 4137 (a morpholinium arylmorpholinophosphinodithionate) | 8.5 |
| ACS 83 (a levodopa-dithiolethione conjugate) | 7.1 |
| ACS 15* (also known as ATB 337) (a diclofenac-dithiolethione conjugate) | 6.3 |
| ATB 343 (an idomethacin-dithiolethione conjugate) | 5.6 |
| ACS 67 (a latanoprost-dithiolethione conjugate | 5.3 |
| ACS 6 (a sildenafil-dithiolethione conjugate) | 3.5 |

TABLE 3

| | Effect | Mediator (s) | Affected stage(s)* 1 | 2 | 3 | 4 |
|---|---|---|---|---|---|---|
| 1 | Increased immunocompetence | GSH(↑), Taurine (↑) | | | | |
| 2 | Abolishment of chronic inflammation/resolution of acute inflammation | GSH(↑), CAMs in Leukocytes(↓), NF-kB (↓) | | | | |
| 3 | Inhibiton of procarcinogen activation by oxidases (Cyp-450, etc) | None (?) | | | | |
| 4 | Carcinogen detoxification | Nrf2(↑), GSH(↑), $SO_4^{-2}$(↑) | | | | |
| 5 | Epigenetic silencing of protooncogenes | SAM (↑) | | | | |
| 6 | Epigenetic reactivation of tumor suppressor genes | HDAC (↓) | | | | |
| 7 | DNA protection/repair | GSH (↑), Trx(↑) | | | | |
| 8 | Inhibition of Nf-kB and TNF-alpha nuclear translocation | GSH(↑) | | | | |
| 9 | Cell cycle arrest | Checkpoint kinase I | | | | |
| 10 | Prooxidant/proapoptotic "redlining" | Sulfane sulfur (↑) ROS (↑) | | | | |
| 11 | Antiangiogenesis (at "high levels" of $H_2S$) | ? | | | | |
| 12 | Antimetastatic effect | E-Cadherin (↑) | | | | |
| 13 | Antisteolytic effect | Nf-kB (↓) | | | | |

*1 = Initiation, 2 = Promotion, 3 = Progression, 4 = Metastasis

Sulfur-Rich Compositions

Preparations of Highly Bioavailable Zerovalent Sulfur-Rich Compositions

In one embodiment, the highly bioavailable zerovalent-sulfur-rich compositions are obtained by Procedure I outlined below to prepare a 2.7 kg lot of a composition comprising highly bioavailable zerovalent sulfur. The starting materials are listed in Table 4 and suitable equipment is listed in Table 5.

TABLE 4

| Material | % Purity (w/w) | Weight (kg) | Volume (L) |
|---|---|---|---|
| Anhydrous sodium metabisulfite ($Na_2S_2O_5$) | 99.4 | 4.890 | |
| Sodium hydrogen sulfide, HYDRATED* (Sodium sulfhydrate, HYDRATED) | 70 | 7.090 | |
| Concentrated sulfuric acid | 98 | 6.408 | 3.483 |
| Distilled water | 100 | 67.25 | 67.25 |
| High-purity ice | 100 | 30.0 | |
| Anhydrous ethyl alcohol (FREE FROM DENATURING ADDITIVES) | ≥99.5 | 5.68 | 7.2 |

*contains approximately 30% water and 70% NaHS

TABLE 5

| Equipment | Preferred specifications |
|---|---|
| 200 L main reaction vessel | plastic or glass-lined |
| 80 L auxiliary reaction vessel | plastic or glass-lined |
| 40 L vessel | plastic or stainless steel |
| 19 L vessel | plastic or stainless steel |
| 10 L vessel | Plastic or stainless steel |
| Large trays | Stainless steel or glass |
| High-torque motor-stirrer assembly (220 v, 3 HP) with a frequency converter-speed control (ABB, model ACS 150) | Should be capable of continuously varying speed between 0 and 1725 rpm. The speed scale shown in the display should go from 0 to 50. The dimensions of the 304 stainless steel propeller-type stirrer shaft should be 80 cm long and 1 inch in diameter. |
| Low-torque stirrer | — |
| pH meter or pH measuring sticks | — |
| Thermometer (−5-110° C.) | — |
| Measuring cylinders | — |
| Scales | — |
| 4 L-Kitasato flask | — |
| Buchner funnel | 185 mm internal diameter |
| Two additional funnels | Graduated |
| At least 2 full-face safety masks fitted with cartridges designed to absorb acid fumes | — |
| Vacuum pump or water ejection vacuum system | — |

Procedure I

Add portionwise and under brisk stifling, 4.890 kg of $Na_2S_2O_5$ to 20 L of distilled water contained in the 200 L-main reaction vessel fitted with the high-torque stirrer (7-8 shown in display). The addition is desirably made over 3-5 minutes and an effort should be made to keep the powder from forming lumps. Dissolve 7.090 kg of $NaHS \cdot xH_2O$ in 15 L of distilled water contained in the 80 L auxiliary reaction vessel fitted with the low-torque stirrer. Filter the NaHS solution through 3 pieces of Whatman #1 filter paper under reduced pressure using a Kitasato-Buchner assembly. Collect the filtrates in a 19 L vessel. It should be noted that only a very small amount of impurities is usually retained on the filter papers.

Next, rinse the 80 L auxiliary reaction vessel and transfer the filtered NaHS solution from the 19 L vessel to the 80 L auxiliary reaction vessel. Add 30 L of distilled water to the 80 L auxiliary reaction vessel that contains the filtered NaHS solution. Pour 1.458 kg of concentrated sulfuric acid (98%) into a stirred mixture of 2.25 kg ice and 2.25 kg distilled water contained in a 10 L vessel. The next two steps should take place simultaneously and should last 40 minutes. Pour, at once, 600 ml of $Na_2S_2O_5$ solution into the auxiliary reaction vessel, which contains the stirred NaHS solution, and start adding (from an addition funnel) the dilute sulfuric acid solution (5.958 kg) into the same vessel with good stirring. Stirring should create a vortex that goes all the way down to the propeller. Wearing a full-face mask (fitted with an acid-absorbing cartridge), add 2.5 kg of ice to the main reaction vessel containing the $Na_2S_2O_5$ solution. Start pouring concentrated sulfuric acid (4.95 kg) in small portions and under brisk stirring. Alternate acid additions with ice additions so as to prevent the solution from heating up. Measure the temperature of the solutions in both reaction vessels. The temperature of the solution in the 200 L main reaction vessel ($Na_2S_2O_5$ plus $H_2SO_4$) should be about 0° C. and the solution in the 80 L auxiliary reaction vessel (NaHS plus a bit of $Na_2S_2O_5$ plus $H_2SO_4$) should be between 30-35° C. Charge 5 kg ice into the 200 L reaction vessel ($Na_2S_2O_5$ plus $H_2SO_4$) and then run into it the solution contained in the 80 L auxiliary reaction vessel (NaHS plus a bit of $Na_2S_2O_5$ plus $H_2SO_4$) under brisk stifling (24.5-25 on speed scale shown in display). This operation should take about 10 minutes and stifling should create a vortex that goes all the way down to the propeller. Upon mixing the 2 solutions, the reaction mixture should go from colorless to canary yellow, fluidity increases, there is some frothing, and a yellowish precipitate separates. Measure the final temperature of the reaction mixture as well as its pH. The temperature should be between 25-30° C. and the pH should be close to 3. Continue stirring briskly for 90 minutes. Stirring should create a vortex that goes all the way down to the propeller.

Allow the reaction mixture to stand undisturbed during 24 hours at room temperature. At the end of this stage the yellowish precipitate should lie at the bottom of the vessel in the form of a relatively compact mass. Without perturbing the precipitate, transfer as much as possible of the liquid phase to a different vessel by decantation or siphoning. Transfer the material remaining in the reaction vessel (about 20 L) to a 40 L plastic or glass container and stir during 1 hour to obtain a homogeneous slurry. Filter the slurry through a #1 Whatman filter paper using a Buchner-Kitasato assembly. Wash the filter cake with 1 L of distilled water or until the filtrate shows no acidity. Washing should be done before the filter cake develops cracks in order to prevent channeling. Immediately after washing keep applying vacuum during 10 more minutes. Over-drying will lead to a highly compact filter cake and will bring about great difficulties in subsequent steps. Use of a rubber or plastic filter dam (or similar device) is recommended. Transfer the relatively dry filter cake to a 10 L plastic container and add 7 L of pure anhydrous ethanol. Stir until all the solid is suspended and keep stifling 1 hour. If the suspension is too thick add more anhydrous ethanol. Filter the suspension through a #1 Whatman filter paper, wash the filter cake with 200 ml of anhydrous ethanol, place the rubber dam on top and keep applying vacuum for no longer than 10 minutes. Over-drying will lead to a highly compact filter cake and will bring about great difficulties in subsequent steps. Transfer the filter cake to large glass or stainless steel trays for room-temperature air drying. Allow to dry for about 4 days or until constant weight and absence of ethanol odor. The dry product is a material that consists of easily friable lumps and an impalpable powder. Disaggregate the lumps and sift to make sure that the material goes through a 325 standard sieve.

Procedure I yields a product (SG-1002) containing about 99% zerovalent sulfur and about 1% highly polar components (e.g., sodium sulfate and traces of sodium polythionates and sodium thio sulfate).

In some embodiments, variations of Procedure I may be used to obtain similar materials. Such procedures include but are not limited to the following:

Procedure II

Use sodium sulfide instead of sodium hydrogen sulfide and adjust the amounts of reactants according to rules well known to those skilled in the art, such as increasing the amount of acid, following the process detailed in Procedure I.

Procedure III

Use sodium sulfite instead of sodium metabisulfite and adjust the amount of reactants according to rules well known to those skilled in the art, following the process detailed in Procedure I.

Procedure IV

Use sodium sulfide instead of sodium hydrogen sulfide and sodium sulfite instead of sodium metabisulfite and adjust the amount of reactants according to rules well known to those skilled in the art, following the process detailed in Procedure I.

Procedure V

Use concentrated hydrochloric acid instead of concentrated sulfuric acid with mole-per-mole replacement and following the process detailed in Procedure I.

Procedure VI

Use concentrated hydrochloric acid instead of concentrated sulfuric acid with mole-per-mole replacement and following the process detailed in Procedure II.

Procedure VII

Use concentrated hydrochloric acid instead of concentrated sulfuric acid with mole-per-mole replacement and following the process detailed in Procedure III.

Procedure VIII

Use concentrated hydrochloric acid instead of concentrated sulfuric acid with mole-per-mole replacement and following the process detailed in Procedure IV.

Procedure IX

Use potassium salts instead of sodium salts and adjust the amount of reagents according to rules well known to those skilled in the art, and following the process detailed in Procedure I.

In some embodiments, the reactants used in the procedure can include any compound comprising sulfur in the minus two oxidation state and another compound comprising sulfur in the plus four oxidation state, and optionally an acid and/or catalyst(s).

In other embodiments, vacuum-aided filtration may be replaced by pressure-aided filtration and/or centrifugation. In other embodiments, closed reactors may be used, a heat-exchange cooling system may be substituted for ice addition, spray drying may substitute air drying, and one and/or more steps (e.g., washing with alcohol) may be omitted. It should be understood that embodiments involving a larger or smaller scale of operation are also within the scope of the present invention.

Characterization of Highly Bioavailable Zerovalent-Sulfur-Rich Compositions

The standard yield of dry, sifted product is 2.7 kg of an impalpable, odorless, fluffy, light yellow, microcrystalline powder with the following properties:

Melting range: the mean melting temperature is between about 117° C. and about 121° C.±2-3° C. (e.g., melting occurs between 118-120° C., 116-119° C., or between 119-120° C.).

Zerovalent sulfur content (w/w): 90-99.9% (e.g., 91%, 92%, 93.5%, 94%, 96%, 96.5%, 97.1%, 97.5%, 98%, 98.6%, 98.9%, or 99.5%)

Elemental alpha sulfur content (w/w): 90-99.9% (e.g., 91%, 92%, 93.5%, 94%, 96%, 97.1%, 97.5%, 98%, 98.6%, 98.9%, or 99.5%)

Highly polar components (w/w): 0.01-10% (e.g., 0.02%, 0.1%, 0.25%, 0.5%, 0.8%, 1%, 1.5%, 2%, 3%, 4%, 5%, 5.5%, 6%, 7%, 8%, 9%, 9.5%, or 9.9%)

Solubility in water at 25° C.: 0%

Solubility in carbon disulfide: 87-97%

Apparent density (tapped): ~0.6 g/ml

Median particle size distribution: between about 26 and about 33 micrometers (e.g., 26.5, 27, 27.3, 28, 28.5, 29, 29.5, 30, 31.3, 32, 32.5, or 32.9)

Sodium content: ~0.03%

Oxygen content (by difference): ~0.12%

The composition obtained by adhering to Procedure I consists of microcrystals rich in zerovalent sulfur; its solubility in carbon disulfide is lower than that of alpha-sulfur (rhombic sulfur) and contains measurable amounts of sodium and oxygen. X-ray diffraction patterns of the composition are consistent with that of alpha sulfur.

The methods used to obtain the data described herein include the following. The solubility of the composition in carbon disulfide was obtained by adding 6 mL of carbon disulfide to 0.500 g of the final product and determining the weight of the residue. Zerovalent sulfur content was measured by sulfitolysis not correcting for the fact that sulfitolysis converts all sulfur atoms in $S_8$ into thiosulfate but only (n−1) sulfur atoms in $Na^{+-}O_3S—S_nSO_3^-Na^+$. Sodium content was determined by Galbraith Laboratories, USA (GLI procedure ME-70). Particle size distribution was measured using a Partica LA-950 laser diffraction particle size analyzer from Horiba Instruments.

Without being limited by any hypothesis, it is likely that the high bioavailability of the above material is associated with the hydrophilic nature of the crystal surfaces, which in turn may be related to the presence of highly polar groups such as $^-SO_3Na$ and/or $=SO_3Na_2$. These groups might be those present in polythionate molecules ($Na^{+-}O_3S—S_n—SO_3^-Na^+$, e.g., where n=1, 2, or 3), thiosulfates, or sulfates. Highly polar groups such as $^-SO_3Na$ may be associated with molecules of water of hydration and may, under some circumstances, undergo cationic exchange, yielding, e.g., $^-SO_3H$ groups. Further, the hydrophilicity of the surface of this unique microcrystalline material is in stark contrast with the hydrophobic nature of the surface of crystals of pure alpha- or beta-elemental sulfur. Pure alpha- or beta-elemental sulfur in contrast, is completely soluble in carbon disulfide. Also without being limited by any hypothesis or theory, it is likely that the low bioavailability of ordinary alpha sulfur is directly related to the hydrophobic nature of its surface.

In some embodiments, the composition can be micro- or nanosized, comprising particles rich in alpha sulfur but always modified so as to possess hydrophilic surfaces. Similar compositions also within the scope of the present invention can be obtained by any chemical, electrochemical, mechanochemical, sonochemical, photochemical, microwave-assisted, biochemical and/or biotechnological processes known in the art. Compositions comprising elemental beta sulfur and surface modifying polar groups further constitute embodiments of the present invention. As established, elemental alpha sulfur is converted into beta sulfur when heated and vice versa.

Determination of Zerovalent Sulfur Content in the Highly Bioavailable Zerovalent Sulfur-Rich Compositions In one aspect, the zerovalent sulfur content of the composition of the invention can be determined using the method described herein to measure the percentage (w/w) of zerovalent sulfur in alpha sulfur, sodium thiosulfate, and sodium polythionates. The sulfitolysis method for determining zerovalent sulfur content described herein does not correct for the fact that sulfitolysis of polythionate molecules stops at the trithionate as shown in equation (ii), therefore, one of the zerovalent sulfur atoms present in each polythionate molecule escapes sulfitolysis and is not converted into thiosulfate (equation (ii)). However, since the sodium content of the composition disclosed herein is small, the error introduced in the calculation of % zerovalent sulfur is correspondingly small. A detailed analysis of sulfitolysis is described in Koh et al., *Anal. Sci.* 6:3-14, 1990.

The sulfitolysis reactions equation (i) and (ii) proceed as in the volumetric method for quantitative determination of elemental sulfur in aromatic hydrocarbons reported by Morris et al., *Anal. Chem.* 20:1037-1039, 1948. The sulfitolysis method described herein is improved compared to the method of Morris et al. in several ways, including the use of n-hexadecyl pyridinium chloride as a sulfitolysis catalyst.

$$S_8 + 8SO_3^{2-} \rightarrow 8S_2O_3^{2-} \quad \text{Equation (i)}$$

$$^-O_3S-S_nSO_3^- + (n-1)SO_3^{2-} \rightarrow (n-1)S_2O_3^{2-} + {}^-O_3S-S-SO_3^- \quad \text{Equation (ii)}$$

The reagent solutions and methods of preparation of the solutions are shown in Table 6.

TABLE 6

| Reagent Solution | Preparation of Solution |
|---|---|
| Sodium sulfite (15% w/w) aqueous solution | Weigh 150 grams of anhydrous chemically pure sodium sulfite and dissolved in 850 mL distilled water. |
| Formaldehyde aqueous solution (37%) | — |
| 6N HCl | Measure 250 mL of concentrated hydrochloric acid (approximately 12N) and dilute to 500 mL with distilled water. |
| KI (10% w/w in water) | Weigh 50 grams chemically pure KI and dissolve in 450 mL distilled water. |
| 0.200N KIO$_3$ | Weigh 7.134 grams of high purity anhydrous KIO$_3$ dissolve in 100 mL distilled water and dilute to 1 L with distilled water. |
| Hexadecylpyridinium chloride monohydrate (1% w/w) solution in water | Weigh 1 gram solid monohydrate and dissolve in 99 mL distilled water. |
| Soluble starch (5 g/L, aqueous solution) | Weigh 1 gram soluble starch, add 10 mg red mercuric iodide, add cold water to form a paste, then add 200 mL boiling water and boil for 1 or 2 minutes while stirring. Allow the solution to cool to room temperature. |

To determine the zerovalent sulfur content, weigh 0.160 g±10 mg of the composition into a 250 mL Erlenmeyer flask. Add to the flask 100 mL of 15% Na$_2$SO$_3$ solution. Place the flask in a water bath and apply heat until the water boils. Then add 0.5 mL of 1% hexadecylpiridinium chloride monohydrate solution and continue heating until the solid disappears completely. Allow the contents in the flask to cool down to room temperature and place a magnetic stifling bar inside. While stirring, add 15 mL formaldehyde solution, 25 mL 6N solution, 10 mL of 10% KI solution, and 1 mL of 0.5% soluble starch indicating solution. The resulting solution should be colorless. Titrate the contents in the flask with 0.2N KIO$_3$ solution using a 25 mL burette. As the titration starts, the contents of the flask become amber-colored, but the color disappears quickly. As the equivalence point is approached be very careful not to overstep. The final point is reached when a drop of titrating solution produces no color change.

$$\text{Titration reaction } IO_3^- + 5I^- + 6H^+ + 6S_2O_3^{2-} \rightarrow 6I^- + 3S_4O_6^{2-} + 3H_2O \quad \text{Equation (iii)}$$

$$\% \text{ zerovalent sulfur}^* = (V_{KIO_3}(\text{mL}) \times N_{KIO_3} \times 32.07 \times 100)/(1000 \times \text{sample weight(g)}) \quad \text{Formula (iv)}$$

* susceptible of undergoing sulfitolysis

Conditions and Disorders

The highly bioavailable zerovalent-sulfur-rich compositions described herein can be used to treat a cardiovascular disease, hyperproliferative diseases (e.g., cancer), an inflammatory disease, diabetes, dyslipidemia, a neurodegenerative disease, AIDS, and other pathological conditions associated with oxidative stress, an imbalance in redox homeostasis, and/or immune dysfunction.

In one aspect, compositions of the invention are administered to a subject already suffering from a cardiovascular disease, an inflammatory disease, a neurodegenerative disease, AIDS, and a pathological condition associated with oxidative stress and/or an imbalance in redox homeostasis, or cancer. In another aspect, compositions of the invention may also be administered to a subject at risk for developing a cardiovascular disease, hyperproliferative diseases (e.g., cancer), an inflammatory disease, diabetes, dyslipidemia, a neurodegenerative disease, AIDS, and other pathological condition associated with oxidative stress, an imbalance in redox homeostasis, and/or immune dysfunction.

Cardiovascular Diseases

The compositions of the invention are also useful in treating cardiovascular diseases. As used herein cardiovascular diseases included, but are not limited to, arteriosclerosis, coronary heart disease, ischemia, endothelium dysfunction, in particular those dysfunctions affecting blood vessel elasticity, restenosis, thrombosis, angina, high blood pressure, cardiomyopathy, hypertensive heart disease, heart failure, cor pulmonale, cardiac dysrhythmias, endocarditis, inflammatory cardiomegaly, myocarditis, myocardial infarction, valvular heart disease, stroke and cerebrovascular disease, aortic valve stenosis, congestive heart failure, and peripheral arterial disease. In one aspect, the invention includes methods of administering the highly bioavailable zerovalent-sulfur-rich compositions for chronic treatment. In another aspect, the invention also includes methods of administering the highly bioavailable zerovalent-sulfur-rich compositions for acute treatment.

In preferred embodiments, the highly bioavailable zerovalent-sulfur-rich compositions of the invention will restore and/or improve cardiovascular parameters to normal ranges in a subject diagnosed with or at risk of a cardiovascular disease. Normal ranges of cardiovascular parameters include but are not limited to, an end-diastolic volume (EDV) from about 65-240 mL, an end-systolic volume (ESV) from about 16-143 mL, a stroke volume from about 55-100 mL, an ejection fraction from about 55-70%, a heart rate from about 60-100 bpm, and/or cardiac output of about 4.0-8.0 L/min.

Inflammatory Diseases

Highly bioavailable zerovalent-sulfur-rich compositions of the invention may also be used to treat inflammatory diseases. Examples of inflammatory diseases include, but are not limited to acne vulgaris, asthma, autoimmune diseases (e.g., acute disseminated encephalomyelitis (ADEM), Addison's disease, agammaglbulinemia, alopecia greata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune-hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo concentric sclerosis, Behcet's disease, Berger's disease, Bickerstaff's encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic vasculitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, giant cell arteritis, glomerulonephritis, Goodpasture's syndrome, Grave's disease, Guillain-Barre syndrome, Hashimoto's encephalopathy, Hashimoto's thyroiditis, Henoch-Schonlein purpura, herpes gestationis, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, myasthenia gravis, myositis, narcolepsy, neuromyelitis optica, neuromyotonia, ocular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria, Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriatic arthritis, pyoderma gangrenosum, pure red cell aplasia, Rasmussen's encephalitis, raynaud phenomenon, relapsing polychondritis, Reiter's syndrome, restless leg syndrome, retroperitoneal fibrosis, rheumatic fever, Schnitzler syndrome, scleritis, scleroderma, serum sickness, Sjogren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, undifferentiated spondyloarthropathy, vitiligo, and Wegener's granulomatosis), celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, and osteoarthritis.

Neurodegenerative Diseases

Highly bioavailable zerovalent-sulfur-rich compositions of the invention may also be used to treat neurodegenerative diseases. Neurodegenerative diseases are any diseases that are characterized by the progressive loss of structure or function of neurons, including death of neurons. Neurodegenerative diseases may be caused by genetic mutations (e.g., CAG nucleotide triplet mutation), protein misfolding (e.g., aggregation of alpha-synuclein, hyperphosphorylated tau protein, and aggregation of beta amyloid), misregulation in protein degradation pathways (e.g., ubiquitin-proteasome pathway and autophagy-lysosome pathways), membrane damage, mitochondrial dysfunction, defects in axonal transport, and misregulation of programmed cell death pathways (e.g., apoptosis, autophagic, and cytoplasmic). Examples of neurodegenerative diseases include, but are not limited to Alzheimer's disease, Parkinson's disease, Huntington's disease, amyotrophic lateral sclerosis (ALS), Creutzfeldt-Jakob disease, primary progressive aphasia, progressive supranuclear palsy, spinocerebellar ataxia type 3, frontotemporal dementia, dementia with Lewy bodies, corticobasal degeneration, prion disorders, multiple system atrophy, hereditary spastic paraparesis, Friedreich's ataxia, and amyloidoses.

Other Pathological Conditions Associated with Oxidative Stress and/or an Imbalance in Redox Homeostasis Highly bioavailable zerovalent-sulfur-rich compositions of the invention may be useful in treating other conditions associated with oxidative stress including but not limited to autism, schizophrenia, bipolar disorder, fragile X syndrome, sickle cell disease, chronic fatigue syndrome, osteoarthritis cataract, macular degeneration, toxic hepatitis, viral hepatitis, cirrhosis, chronic hepatitis, oxidative stress from dialysis, renal toxicity, kidney failure, ulcerative colitis, bacterial infection, viral infections, such as HIV and AIDS, herpes, ear infection, upper respiratory tract diseases, hypertension, balding and hair loss, over-training syndrome related to athletic performance, eczema, scleroderma, atopic dermatitis, polymyositis, and dermatitis herpetiformis.

In preferred embodiments, the compositions of the invention can be formulated for topical administration and/or enteral administration to treat conditions such as psoriasis, athlete's foot, and/or rosacea. In some embodiments, the highly bioavailable zerovalent-sulfur-rich compositions of the invention may be useful in healing wounds by influencing the stages of wound healing including but not limited to hemostasis, inflammatory, proliferative, and remodeling. In another embodiment, the highly bioavailable zerovalent-sulfur-rich compositions of the invention also enhance athletic performance by increasing one or more of the factors of: endurance, energy, strength, visual acuity, and/or coordination.

In another preferred embodiment, the compositions of the invention can be formulated for enteral administration to treat male infertility. Oxidative stress plays a major role in the etiology of sperm dysfunction via induction of peroxidative damage to the plasma membrane. Furthermore, oxidative stress affects the integrity of the sperm nuclear and mitochondrial genomes, leading to DNA strand breaks, aberrant recombination, and/or defective packing, as well as chromatin cross-linking. The observation of correlations between reactive oxygen species (ROS) generation by washed human sperm suspensions and their fertilizing capacity is consistent with the clinical significance of oxidative damage to human spermatozoa; this significance is bolstered by the demonstration of loss of functional competence and high rates of DNA damage of human spermatozoa directly or indirectly exposed to hydrogen peroxide. When the source of ROS is intracellular, many of the classical antioxidants that are effective against extracellular oxidative stress (e.g., NAC and hypotaurine) prove useless.

The high susceptibility toward irreversible oxidative damage of mammalian sperm cells may be attributed to: (i) the particularly high content of polyunsaturated fatty acids, plasmalogens, and sphingomyelins of their membranes, (ii) the lack of adequate repair mechanisms for oxidative damage, derived from a dearth of cytosolic antioxidant enzymes associated with the loss of most of their cytoplasm upon spermiation, (iii) the fact that mature post-epididymal sperm cells possess highly condensed nuclear chromatin (due to the replacement of histones by protamine, with increased disulfide bond formation); this compactness contributes to silencing the paternal chromosomes, which are unable to engage in transcriptional activation by ROS, (iv) the fact that sperm cells are particularly rich in highly active mitochondria, because they need a constant supply of energy to support their motility. Spermatozoa were the first cells found to generate significant levels of ROS and these characteristics increase the probability of mitochondrial membrane damage by leaked ROS, (v) the fact that native cysteine-rich-secretory proteins (CRISPs) contain unusually high numbers of thiolic (unoxidized) cysteine residues, which renders them especially sensitive to inactivation by oxidants.

$H_2S$ may be used by cells to synthesize L-cysteine, which can then serve as a building block in protein synthesis, as described in Predmore et al., *Antioxid Redox Signal.* 17:119-140, 2012. Sulfur-deficient diets, however, are common and may lead to cysteine deficiency-especially in males and consequently to deficits in the biosynthesis of important cysteine-rich proteins such as CRISPs. The CRISPs are found only in vertebrates, within the male reproductive tract. CRISPs have been implicated in many aspects of spermatogenesis, as well as in the actual process of fertilization as reported in Koppers et al., *Asian J. Androl.* 13:111-117, 2011, and down-regulation of CRISP-2 mRNA by a factor of 4.3 in asthenospermic patients was recently reported in Jing et al., *Natl. J. Androl.* 17:203-207, 2011.

Srilatha et al., *J. Sex. Med.,* 4:1304-1311, 2007, have described some pioneering studies that provide evidence for the endogenous formation of hydrogen sulfide and its pro-erectile relaxant effect on the corpus cavernosum of mammals, as well as on the effects of hydrogen sulfide in female sexual function. The first set of results was corroborated by an international team that included Louis J. Ignarro who won the Nobel Prize in 1998 for his work on demonstrating the signaling properties of nitric oxide. There is also evidence that oxidative stress is implicated in erectile dysfunction in diabetic rodents as described in Bivalacqua et al., *J. Sex. Med.* 2:187-197, 2005 and interventions based on administration of tetrahydrobiopterin and up-regulation of antioxidant enzymes may be useful as described in Deng et al., *Methods Mol. Biol.* 610:213-227, 2010 and Minhas et al., *Expert Opin Pharmacother.* 3:889-897, 2002. Moreover, recent work discusses the effects of endogenous and exogenous $H_2S$ on the physiological control of penile tone and the possibility of developing new therapies for erectile dysfunction (ED) that target this pathway.

Sparatore et al., *Expert Rev. Clin. Pharmacol.* 4:109-121, 2011 developed an $H_2S$-donating derivative of sildenafil (ACS6) with possible clinical indications in ED, benign prostatic hypertrophy and low urinary tract symptoms. The $H_2S$ released by ACS6 inhibits both phosphodiesterase type 5 (PDE5) and NADPH oxidase (NOX) expression activity, hence this mechanism may constitute the basis of a new and effective approach to the treatment of patients suffering from ED, benign prostatic hypertrophy and lower urinary tract symptoms. In fact, studies performed by Shukla et al., *BJU Int.* 103:1522-1529, 2009 showed that ACS6 and sildenafil citrate relaxed cavernosal smooth muscle equipotently and ACS6 inhibited superoxide formation and expression of $p47^{phox}$ (a subunit of NOX) more than sildenafil citrate. It was concluded that ACS6 not only promotes erection, but also affords effective protection from oxidative stress through up-regulation of glutathione (GSH) synthesis.

Furthermore, in an investigation of the effect of NaHS on pregnant rat uterine contractility in vitro, Sidhu et al., *Pharmacol Toxicol.* 88:198-203, 2001 found that this "hydrogen donor" produced significant dose-dependent decreases in uterine spontaneous contractility.

Showell et al., *Cochrane Database Syst Rev.* 1:CD007411, 2011 assessed the effects of oral antioxidants on men with documented sperm DNA damage and/or with impaired semen parameters on the basis of clinical trials wherein the participants were randomly assigned to antioxidant versus placebo, an alternative antioxidant, or no treatment. The outcomes considered were: 1) life birth rate per couple randomized, 2) pregnancy rate per couple, 3) miscarriage rate per couple, or spontaneous abortion, 4) stillbirth rate per couple, 5) level of sperm DNA damage after treatment, 6) sperm concentration, 7) sperm motility, and 7) adverse effects. The 44 trials analyzed in this review involved 2876 couples, carried out over an average duration of treatment of 4.1 months, and included the following antioxidants: vitamin B, vitamin C, vitamin E, selenium, magnesium, zinc, zinc plus vitamin E, zinc plus vitamin E plus vitamin C, combined antioxidants plus minerals (e.g., vitamin C, vitamin E, zinc, selenium, folic acid, lycopene, and garlic oil), L-acetylcarnitine, L-carnitine, L-acetyl carnitine plus L-carnitine, pentoxifylline, ethyl cysteine, N-acetylcysteine, and docosahexenoic acid. The study concluded that antioxidant supplementation in sub-fertile males may improve the outcomes of live birth and pregnancy rate for sub-fertile couples undergoing treatment (ART cycles). Further head-to-head comparisons are necessary to identify the superiority of one antioxidant over another. These results indicate that there is currently only limited scientifically acceptable evidence that antioxidant supplementation improves outcomes for sub-fertile couples or the available forms of treatment have mostly produced only marginally satisfactory responses, even in the best of proper trials and that many drugs are being used without any rationale. According to Cavallini et al, *Asian J. Androl.* 8:143-157, 2006, no drug can be defined as unquestionably effective for the treatment of male idiopathic oligoasthenoteratozoospermia.

The highly bioavailable zerovalent-sulfur-rich composition of the invention was used in a clinical trial conducted by Mexican researchers (see Example 8) and the results were highly encouraging for several reasons including: a treatment duration of only 2.5 months versus an average of 4.1 months for all trials described in Showell et al., *Cochrane Database Syst Rev.* 1:CD007411, 2011, and a single-component formulation instead of an un-optimized miscellaneous mixture of 7-10 or more presumably active ingredients.

Oxidative stress is associated with an increase in the production of oxidizing species (e.g., superoxide, peroxides, free radicals) and/or a significant decrease in effectiveness and/or levels of antioxidant defenses, such as glutathione. The highly bioavailable zerovalent-sulfur-rich compositions of the invention when administered will desirably act to restore the cysteine and glutathione levels thus restoring the redox homeostasis in the body.

Diabetes

Compositions of the invention may also be useful for treating diabetes and its complications. Diabetes can be any metabolic disease in which a person has high blood sugar, either because the body does not produce enough insulin, or because cells do not respond to the insulin that is produced. Non-limiting examples of diabetes includes, type 1 diabetes mellitus, type 2 diabetes mellitus, gestational diabetes, congenital diabetes, cystic fibrosis-related diabetes, steroid diabetes, latent autoimmune diabetes of adults, and monogenic diabetes. Complications associated with diabetes include but are not limited to hypoglycemia, diabetic ketoacidosis, nonketotic hyperosmolar coma, cardiovascular disease, chronic renal failure, diabetic nephropathy, diabetic neuropathy, diabetes-related foot problems (e.g., diabetic foot ulcers), and diabetic retinopathy.

Cancers

Other conditions that may be treated using highly bioavailable zerovalent-sulfur-rich compositions of the invention include cancers. Cancers are generally characterized by unregulated cell growth, formation of malignant tumors, and invasion to nearby parts of the body. Cancers may also spread to more distant parts of the body through the lymphatic system or bloodstream. Cancers may be a result of gene damage due to tobacco use, certain infections, radiation, lack of physical activity, obesity, and/or environmental pollutants. Cancers may also be a result of existing genetic faults within cells to cause diseases due to genetic heredity. Screenings may be used to detect cancers before any noticeable symptoms appear and treatment may be given to those who are at higher risks of developing cancers (e.g., people with a family history of cancers). Examples of screening techniques for cancer include but are not limited to physical examination, blood or urine tests, medical imaging, and/or genetic testing. Non-limiting examples of cancers include: bladder cancer, breast cancer, colon and rectal cancer, endometrial cancer, kidney or renal cell cancer, leukemia, lung cancer, melanoma, Non-Hodgkin lymphoma, pancreatic cancer, prostate cancer, ovarian cancer, stomach cancer, wasting disease, and thyroid cancer.

Transplants

The zerovalent-sulfur-rich composition of the invention are expected to be effective in treating ischemia-reperfusion injury from reconstructive and transplantation procedures. Water dispersions of fine particles of the zerovalent-sulfur-rich composition can be used to treat flaps of tissue from plastic or reconstructive surgery and solid organs from transplants in order to prevent/minimize ischemia-reperfusion injury and to protect the mitochondria during the operative procedures. Exemplary tissues and organs to be treated using the composition of the invention have active metabolism and increased mitochondrial function and are susceptible to reperfusion injury after brief periods of ischemia and include but are not limited to; skeletal muscle, the heart, the liver, large intestine, small intestine, the brain, the skin, the limbs (e.g., arms, legs, feet, hands).

Pharmaceutical Compositions and Treatment Methods

The present invention also relates to pharmaceutical compositions that contain the highly bioavailable zerovalent sulfur-rich compositions or a combination of one of the highly bioavailable zerovalent sulfur-rich compositions described herein and a second therapeutic agent (e.g., an antiplatelet drug, a β blocker, an angiotensin-converting-enzyme (ACE) inhibitor or angiotensin-receptor blocker (ARB), a statin, fibrates, biguanides, blood pressure lowering agents, cytokines, cholesterol lowering agents, erectile dysfunction drugs, anti-inflammatory drugs, anti-thrombosis drugs, anticancer drugs, anti-diabetic drugs, and/or dietary supplements).

A composition of the present invention can be administered by a variety of methods known in the art. As will be appreciated by the skilled artisan, the route and/or mode of administration will vary depending upon the desired results. The pharmaceutical compositions can be formulated for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mentioned agents dissolved, colloidally dispersed, or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like.

The therapeutic composition may be in the form of a solution, colloidal dispersion, a suspension, an emulsion, an infusion device, or a delivery device for implantation or it may be presented as a dry powder to be used as such or to be reconstituted with water or another suitable vehicle before use. The composition can be in the form of a tablet, capsule (e.g., hard gelatin capsule and soft gelatin capsule), liquid, or sustained release tablet for oral administration; or a liquid for intravenous, intrathecal, subcutaneous or parenteral administration; or a cream or ointment for topical administration, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the substances. Nanoparticulate formulations (e.g., biodegradable nanoparticles, solid lipid nanoparticles, liposomes) may be used to control the biodistribution of the substances. Other potentially useful delivery systems include ethylene-vinyl acetate copolymer particles, osmotic pumps, intrathecal pumps, implantable infusion systems, and liposomes. The concentration of the substance in the formulation varies depending upon a number of factors, including the dosage of the drug to be administered, and the route of administration.

To administer a composition of the invention by certain routes of administration, it may be necessary to coat the composition with, or co-administer the composition with a material to prevent its inactivation. For example, the composition may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7:27-41, 1984). Pharmaceutically acceptable carriers include sterile aqueous solutions or dispersions and sterile powders for the extemporaneous preparation of sterile injectable colloidal solutions or dispersion. The use of such media and agents for pharmaceutically active substances is known in the art and is included in the invention except where any conventional media or agent is incompatible with the active substance. Supplementary active substances can also be incorporated into the compositions.

Therapeutic compositions typically must be sterile and stable under the conditions of manufacture and storage. The composition can be formulated as a suspension, microemulsion, liposome, or other ordered structure suitable to high drug concentration. The carrier can be a solvent or dispersion medium containing, for example, water, ethanol, petroleum jelly (e.g., Vaseline®), polyol (e.g., glycerol, propylene glycol, and liquid polyethylene glycol, and the like), and suitable mixtures thereof, formulated at different percentages (e.g., 5, 10, 15, 20, 25, 30, 35, 40, 45, or 50% by weight in a dispersion medium described herein). The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Colloidal dispersions may be stabilized through addition of agents well known in the art.

The compositions of the invention may be sterilized by conventional sterilization techniques, or may be sterile filtered. The resulting aqueous dispersions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid or semisolid form may be packaged in multiple single dose units, each containing a fixed amount of the composition, such as in a sealed package of tablets or capsules. The composition in solid form can also be packaged in a container for a flexible quantity, such as in a squeezable tube designed for a topically applicable cream or ointment.

Preferred formulations of the invention include but are not limited to: preparation of hard gelatin capsules containing 100-400 mg of a highly bioavailable zerovalent-sulfur-rich composition of the invention, preparation of a suspension of about 5-20% (5.5%, 6%, 6.5%, 7%, 8%, 10%, 15%, 17%, or 19%) of highly bioavailable zerovalent-sulfur-rich composition of the invention and petroleum jelly (e.g., Vaseline®) or polyethylene glycol, or a colloidal dispersion of about 5-20% (5.5%, 6%, 6.5%, 7%, 8%, 10%, 15%, 17%, or 19%) of highly bioavailable zerovalent-sulfur-rich composition of the invention in water or oil.

Sterile injectable colloidal suspensions can be prepared by incorporating the active compound in the required amount in an appropriate solvent with one or a combination of ingredients enumerated above, as required, optionally followed by sterilization microfiltration. Generally, dispersions are prepared by incorporating the active compound into a sterile vehicle that contains a basic dispersion medium and the required other ingredients from those enumerated above. Dosage regimens are adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic or prophylactic situation. For example, the compositions of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic or prophylactic effect, optionally in association with the required pharmaceutical carrier. The specifications for the dosage unit forms of the invention are dictated by and directly dependent on (a) the unique characteristics of the active substance and the particular therapeutic or prophylactic effect to be achieved, and (b) the limitations inherent in the art of compounding such an active substance for the treatment of sensitivity in individuals.

When the substances of the present invention are administered as pharmaceuticals, to humans and animals, they can be given alone or as a pharmaceutical composition containing, for example, 1 to 100% (more preferably, 10 to 100%, such as 90 to 100%) of active ingredient, optionally in combination with one more pharmaceutically acceptable carriers or excipients.

The compositions containing an effective amount can be administered for prophylactic or therapeutic treatments. In prophylactic applications, compositions can be administered to a patient with a clinically determined predisposition or increased susceptibility to development of cardiovascular diseases, hyperproliferative diseases (e.g., cancer), inflammatory diseases, diabetes, dyslipidemia, neurodegenerative diseases, AIDS, and other pathological conditions associated with oxidative stress, an imbalance in redox homeostasis, and/or immune dysfunction. Compositions of the invention can be administered to the patient (e.g., a human) in an amount sufficient to delay, reduce, or preferably prevent the onset of the clinical disease. In therapeutic applications, compositions are administered to a patient (e.g., a human) already suffering from a cardiovascular disease, hyperproliferative diseases (e.g., cancer), an inflammatory disease, diabetes, dyslipidemia, a neurodegenerative disease, AIDS, and other pathological conditions associated with oxidative stress, an imbalance in redox homeostasis, and/or immune dysfunction, in an amount sufficient to cure or at least partially arrest the symptoms of the condition and its complications. An amount adequate to accomplish this purpose is defined as a "therapeutically effective dose," an amount of a compound sufficient to substantially improve some symptom associated with a disease or a medical condition. For example, in the treatment of a cardiovascular disease, hyperproliferative diseases (e.g., cancer), an inflammatory disease, diabetes, dyslipidemia, a neurodegenerative disease, AIDS, and other pathological conditions associated with oxidative stress, an imbalance in redox homeostasis, and/or immune dysfunction, an agent or substance which decreases, prevents, delays, suppresses, or arrests any symptom of the disease or condition would be therapeutically effective. A therapeutically effective amount of an agent or substance is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

The compositions and formulations of the present invention may be used in combination with either conventional methods of treatment or therapy or may be used separately from conventional methods of treatment or therapy. When the substances and formulations of this invention are administered in combination therapies with other agents, they may be administered sequentially or concurrently to an individual. Alternatively, pharmaceutical compositions according to the present invention include a combination of a substance or formulation of the present invention optionally in association with a pharmaceutically acceptable excipient, as described herein, and another therapeutic or prophylactic agent known in the art.

The formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc.

Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Dosage

The pharmaceutical compositions of the present invention are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the substances of the invention employed in the pharmaceutical composition at levels lower than that required in order to achieve the desired therapeutic effect and gradually increase the dosage until the desired effect is achieved. In general, a suitable daily dose of a composition of the invention will be that amount of the substance which is the lowest dose effective to produce a therapeutic effect. Such an effective dose will generally depend upon the factors described above. Preferably, the effective daily dose of a therapeutic composition may be administered as two, three, four, five, six or more sub-doses administered separately at appropriate intervals throughout the day, optionally, in unit dosage forms.

Preferred therapeutic dosage levels are between about 800 mg to about 1600 mg (e.g., 800, 850, 900, 1000, 1050, 1100, 1200, 1300, 1400, 1450, 1500, 1550, and 1600 mg) of active zerovalent-sulfur-rich composition per day administered orally to adults of average weight afflicted with most of the symptoms, syndromes and pathological conditions described herein, Preferred prophylactic dosage levels are between about 100 mg to about 1200 mg (e.g., 110, 140, 200, 250, 300, 350, 400, 460, 700, 750, 800, 900, 1000, 1100, and 1150 mg). In cancer, AIDS, and some chronic or refractory pathologies, the preferred oral dosage levels are 2400 mg per day or higher (e.g., 2450, 2500, 3000, 3500, 4000, 8000 mg, 1 g) for an adult of average weight. For children afflicted with cancer, the dose may be titrated (e.g., the dose may be escalated gradually until signs of gastrointestinal toxicity appear, such as diarrhea or nausea). In preferred embodiments, the highly bioavailable zerovalent-sulfur-rich compositions of the invention are extremely safe for oral administration and most patients can tolerate higher dosages as treatment progresses.

In other embodiments, the highly bioavailable zerovalent-sulfur-rich compositions of the invention are safe for topical administration. Acceptable dosage forms for topical administration can be formulated as creams, lotions, pastes, gels, and/or ointments containing the highly bioavailable zerovalent-sulfur-rich compositions.

Final dosage forms suitable for administration to human subjects may comprise one of the highly bioavailable zerovalent-sulfur-rich compositions as pharmacologically-active agent or further comprise other active agents such as alpha-lipoic acid, carnitine, carnitine tartrate, carnitine fumarate, coenzyme Q10, selenium, alpha-ketoglutaric acid, potassium alpha-ketoglutarate, diethyl alpha-ketoglutarate, oxaloacetic acid, sodium oxaloacetate, diethyl oxaloacetate, 2-oxo-3-(ethoxycarbonyl)-pentanodioc acid diethyl ester, L-cystine, paracetamol, a sulfa drug, an NSAID, a corticosteroid, taurine, a vitamin, a prebiotic, another anticancer drug, including but not limited to another mitocan (e.g., a drug targeting the mitochondrial electron transport chain), alkylating agents (e.g. procarbazine, dacarbazine, altretamine, cisplatin), methotrexate, purine antagonists (e.g., mercaptopurine, thioguanine, cladribine, pentostatin), pyrimidine antagonists (e.g., fluorouracil, cytarabine, azacitidine), plant alkaloids (e.g., vinblastine, etoposide, topotecan), hormonal agents (e.g., tamoxifen, flutamide), antibiotics (e.g., doxorubicin, daunorubicin, mitomycin, bleomycin), and mitocans (e.g., sodium dichloroacetate and 3-bromopyruvic acid).

Medical Food

The present invention also relates to highly bioavailable zerovalent-sulfur-rich compositions as medical food for daily intake and for maintaining and promoting general health. Evidence indicates that daily ingestion by an adult of average weight of about 800 mg of the highly bioavailable zerovalent sulfur-rich composition described herein during extended periods is safe and beneficial to health because it brings about a marked reduction in the frequency and severity of digestive and respiratory infections (e.g., of viral and bacterial origin) and allergic episodes. Daily intake of the composition of the invention is also associated with a greatly reduced probability of being afflicted by cancer, AIDS, a neurodegenerative condition, stroke, diabetes and its complications, cardiovascular disease, and confers protection from cardiovascular, cerebrovascular, gastric, and hepatic damage caused by xenobiotics including, drugs such as paracetamol, corticosteroids, NSAIDs and antiretrovirals, toxins and poisons (e.g., cyanide, thallium, methanol). Daily intake of the composition of the invention can also result in faster growth of hair and nails, firmer skin, a prebiotic-like effect, and a sense of general wellness.

In one aspect, highly bioavailable zerovalent-sulfur-rich compositions of the invention are used as a paravitamin to provide a supplemental source of cysteine and its derivatives. Cysteine and its derivatives (e.g., glutathione, taurine, taurine conjugates with bile acids, hydrogen sulfide, and sulfate ions) play a role similar to that of vitamins. Like antioxidative vitamins, cysteine and its derivatives play a role in the oxidant/antioxidant balance and indirectly in the regulation of metabolic processes. Cysteine supplementation on top of the normal diet can have various beneficial effects, for example, cysteine supplementation can lead to an increase in muscle function, immune function, plasma albumin concentration and a decrease in TNF-α concentration. Supplementation can also restore the body's reservoirs of cysteine and glutathione levels which are driving forces behind multiple ageing-related processes.

In another aspect, the paravitamins are medical foods providing a minimum amount of calories and maximum amount of a bioavailable form of sulfur intended for humans not receiving enough sulfur in their diets. Studies from a preliminary clinical trial showed that in 120 men and women participants given the highly bioavailable zerovalent-sulfur-rich composition as a paravitamin, most participants noticed faster growth of hair and nails. Furthermore, evidence obtained from in vivo experiments showed that in mammals, hydrogen sulfide, sulfane sulfur, and glutathione levels are increased in blood and tissues upon administration of the highly-bioavailable sulfur-rich compositions as paravitamins.

In preferred embodiments, the highly bioavailable zerovalent-sulfur-rich composition is rapidly and efficiently converted into hydrogen sulfide in the body, which in turn is largely transformed into L-cysteine. L-cysteine may be used as a building block in the synthesis of peptides enzymes, and other proteins and small sulfur-containing biomolecules (e.g., keratin which constitutes 14% of hair and nails, e.g., glutathione, a tripeptide needed for regulating and potentiating immune function and for cellular protection from oxidants, electrophiles, e.g., taurine, which is essential for cardiovascular function, development, and function of skeletal muscle, the retina, the central nervous system, it is a major constituent of bile; has many fundamental biological roles such as conjugation of bile acids, antioxidant, osmoregulation, membrane stabilization, and modulation of calcium signaling, e.g., sulfate, which is necessary for the synthesis of cartilage and for detoxification of many drugs including but not limited to corticosteroids and acetaminophen).

In another embodiment, the zerovalent sulfur-rich composition is transformed and stored as sulfane sulfur. Sulfane sulfur is conveniently used by the body as highly versatile precursor of hydrogen sulfide which readily releases hydrogen sulfide whenever and wherever this species is needed to activate protective genes, block inflammation, and protect cells from free-radical damage.

In yet another preferred embodiment, the maximum human life span may be increased beyond the previous limit by providing compositions of the invention as paravitamins, glutathione levels will be restored to a normal level in the cells of the immune system thereby normalizing the function of the immune system and restoring health and well-being.

Antidotes

The present invention also relates to highly bioavailable zerovalent-sulfur-rich compositions as antidotes for various poisons and drug overdose. The composition of the invention can be used as an antidote for cyanide poisoning. Cyanide poisoning can occur from inhalation and/or ingestion of poisonous cyanide compounds (e.g., hydrogen cyanide gas, potassium cyanide, and sodium cyanide), constant exposure to pesticides and insecticides containing poisonous cyanide compounds, tobacco smoke, inhalation of smoke from building fires and foods including almonds, apricot kernel, cassava, yucca, manioc, and apple seeds. Signs of cyanide poisoning can include but are not limited to permanent paralysis, nervous lesions, hypothyroidism, miscarriages, weakness, mild liver damage, and mild kidney damage.

The composition of the invention can be used as an antidote for drug overdoses including but not limited to acetaminophen overdose and sulfa drug overdose (e.g., sulfamethoxazole, fulfisomidine, dichlorophenamide, acetazolamide, bumetanide, chlorthalidone, clopamide, furosemide, hydrochlorothiazide, mefruside, metolazone, xipamide, acetazolamide, ethoxolamide, sultiame, zonisamide, mafenide, sumatriptan, fulfasalazine, tipranavir, and probenecid).

Combination Therapies

Pharmaceutical compositions of the invention can be administered in combination therapy, i.e., combined with other agents (e.g., an antiplatelet drug, a $\beta$ blocker, an ACE inhibitor or ARB, a statin, fibrates, biguanides, blood pressure lowering agents, cytokines, cholesterol lowering agents, erectile dysfunction drugs, anti-inflammatory drugs, anti-thrombosis drugs, anticancer drugs, anti-diabetic drugs, and/or dietary supplements) depending on the condition to be treated.

Prevention Drugs for Cardiovascular Diseases

Compositions of the invention can be administered in combination with one or more drugs that are used as secondary prevention drugs for cardiovascular diseases. Examples of preventative drugs include, but are not limited to, $\beta$ blockers (e.g., nonselective agents, e.g., alprenolol, carteolol, oxprenolol, sotalol, timolol, e.g., $\beta_1$-selective agents, e.g., acebutolol, betaxolol, celiprolol, metoprolol, e.g., $\beta_2$-selective agents, e.g., butaxamine, e.g., $\beta_3$-selective agents, e.g., SR 59230A), statins (e.g., atorvastatin, cerivastatin, fluvastatin, lovastatin, mevastatin, pravastatin, simvastatin, and rosuvastatin), fibrates (e.g., bezafibrate, ciprofibrate, clofibrate, gemfibrozil, and fenofibrate), biguanides (e.g., metformin, phenformin, buformin, and proguanil), and/or ACE inhibitors (e.g., sulfhydryl-containing agents, e.g., captopril, zofenopril, e.g., dicarboxylate-containing agents, e.g., enalapril, ramipril, quinapril, perindopril, imidapril, e.g., phosphate-containing agents, e.g., fosinopril).

Drugs for Treatment of Erectile Dysfunction

The highly bioavailable zerovalent-sulfur-rich composition of the invention can be administered in combination with one or more drugs for treatment of erectile dysfunction. Examples of drugs for treatment of erectile dysfunction include, but are not limited to: sildenafil, tadalafil, vardenafil, alprostadil, avanafil, and yohimbine.

Anti-Neurodegenerative Drugs

The highly bioavailable zerovalent-sulfur-rich composition of the invention can be administered in combination with one or more anti-neurodegenerative drugs. Examples of anti-neurodegenerative drugs include, but are not limited to, acetylcholinesterase inhibitors (e.g., donepezil, galantamine, and rivastigmine), anti-glutamate agent (e.g., amantadine, GABA-ergic, valproic acid), reserpine, tetrabenazine, typical/atypical neuroleptics, tricyclic antidepressants, SSRIs, carbamazepine, baclofen, tizanidine, and lamotrigine.

Anti-Inflammatory Drugs

The highly bioavailable zerovalent-sulfur-rich composition of the invention can be administered in combination with one or more anti-inflammatory drugs. Examples of anti-inflammatory drugs include, but are not limited to, steroids (e.g., glucocorticoids, e.g., corticosteroids), non-steroidal anti-inflammatory drugs (NSAIDs) (e.g., aspirin, diflunisal, salsalate, ibuprofen, naproxen, fenoprofen, ketoprofen, flurbiprofen, sulindac, etodolac, ketorolac, nabumetone, piroxicam, meloxicam, tenoxicam, mefenamic acid, flufenamic acid, tolfenamic acid, celecoxib, rofecoxib, parecoxib, etoricoxib, firocoxib, nimesulide, and licofelone), immune selective anti-inflammatory derivatives (ImSAIDs) (e.g., phenylalanine-glutamine-glycine (FEG) and its D-isomeric form (feG)), and/or herbs (e.g., Harpagophytum, hyssop, ginger, turmeric, Arnica montana, and willow bark).

Dietary Supplements

The composition of the invention can be administered in combination with one or more dietary supplements to promote and/or maintain general health. Examples of dietary supplements include, but are not limited to, a vitamin (e.g., Vitamin A, Vitamin $B_1$, $B_2$, $B_3$, $B_5$, $B_6$, $B_7$, $B_9$, $B_{12}$, Vitamin C, Vitamin D, Vitamin E, and Vitamin K), a mineral (e.g., potassium, chlorine, sodium, calcium, magnesium, phosphorus, zinc, iron, manganese, copper, iodine, selenium, and molybdenum), an herb or botanical (e.g., St. John's-wort, kava, Shilajit, and Chinese herbal medicines), an amino acid (e.g., glycine, serine, methionine, cysteine, aspartic acid, glutamic acid, glutamine, tryptophan, and phenylalanine), and a concentrate, constituent, extract, and/or a combination of any of the above.

Anticancer/Anti-Proliferative Drugs

The highly bioavailable zerovalent-sulfur-rich composition can be formulated or administered in combination with one or more anticancer drugs. Examples of anticancer agents include, but are not limited to: chemotherapeutic agents (e.g., arsenic trioxide, cisplatin, carboplatin, chlorambucil, melphalan, nedaplatin, oxaliplatin, triplatin tetranitrate, satraplatin, imatinib, nilotinib, dasatinib, and radicicol), immunomodulatory agents (e.g., methotrexate, leflunomide, cyclophosphamide, cyclosporine A, minocycline, azathioprine, antibiotics (e.g., tacrolimus), methylprednisolone, corticosteroids, steroids, mycophenolate mofetil, rapamycin, mizoribine, deoxyspergualin, brequinar, T cell receptor modulators, and cytokine receptor modulators), antiangiogenic agents (e.g., bevacizumab, suramin, and etrathiomolybdate), mitotic inhibitors (e.g., paclitaxel, vinorelbine, docetaxel, abazitaxel, ixabepilone, larotaxel, ortataxel, tesetaxel, vinblastine, vincristine, vinflunine, and vindesine), nucleoside analogs (e.g., gemcitabine, azacitidine, capecitabine, carmofur, cladribine, clofarabine, cytarabine, decitabine, floxuridine, fludarabine, fluorouracil, mercaptopurine, pentostatin, tegafur, and thioguanine), DNA intercalating agents (e.g., doxorubicin, actinomycin, bleomycin, mitomycin, and plicamycin), topoisomerase inhibitors (e.g., irinotecan, aclarubicin, amrubicin, belotecan, camptothecin, daunorubicin, epirubicin, etoposide, idarubicin, mitoxantrone, pirarubicin, pixantrone, rubitecan, teniposide, topotecan, valrubicin, and zorubicin), folate antimetabolites (e.g., pemetrexed, aminopterin, methotrexate, pralatrexate, and raltitrexed), mitocans (e.g., sodium dichloroacetate and 3-bromopyruvic acid), and other targeting agents (e.g., agents that target particular enzymes or proteins involved in cancer or agents that target particular organs or types of cancers), and combinations thereof.

EXAMPLES

The highly bioavailable zerovalent sulfur-rich compositions of the invention and their uses will now be illustrated by means of the following non-limiting examples. These examples are set forth merely for illustrative purposes and many other variations may be used.

Experimental Methods

Human Blood Samples from Heart Failure Patients

Serum samples were obtained from a cardiac tissue and blood biorepository at the University of Louisville. All procedures were approved by the Institutional Review Board of the University of Louisville. The samples procured after informed consent from patients with advanced heart failure undergoing LV assist device placement. Additional serum samples from control patients were obtained from a commercial vendor (Innovative Research).

Experimental Animals

CSE deficient (KO) mice (C57/Sv129 background) and cardiac restricted (αMHC) CSE Tg mice (C57BL/6J background) were developed as described in Levy et al., *The New England Journal of Medicine.* 322:1561-1566, 1990; Heineke et al., *Nature reviews. Molecular Cell Biology.* 7:589-600, 2006. Male C57BL/6J mice 8-10 weeks of age were purchased from The Jackson Laboratory (Bar Harbor, Me.). All experimental protocols were approved by the Institute for Animal Care and Use Committee at Emory University School of Medicine and conformed to the Guide for the Care and Use of Laboratory Animals, published by the National Institutes of Health (NIH Publication No. 86-23, revised 1996), and with federal and state regulations.

Transverse Aortic Constriction (TAC) Protocol

To create pressure overload, the TAC procedure was performed in 10-14 week old mice. Mice were anesthetized with Ketamine (100 mg/kg) and Xylazine (8 mg/kg) and the core body temperature was maintained in normal range (36-37° C.). Mice were then orally intubated and placed on a rodent ventilator to maintain respiration during the surgical procedure. The second intercostal muscle was incised to visualize the aortic arch. Following identification and dissection of the aortic arch, 7-0 silk suture was placed around the aortic arch between the brachiocephalic trunk and the left carotid artery and ligated around a 27 G blunt needle. The needle was immediately removed after ligation. The chest was surgically closed and mice were put in a recovery chamber with 100% oxygen along with a surgical warming pad to maintain core body temperature within normal limits. At the end of the experimental protocol (i.e., 6 or 12 weeks following TAC surgery) mice were euthanized and heart, lung and blood samples were collected.

Hydrogen Sulfide Donor

A zerovalent-sulfur-rich composition (SG-1002, containing about 99% zerovalent sulfur, melting between 119 and 120° C.) was administered in the diet to mice to achieve dosages of 20 mg/kg/day in C57BL/6J mice or 40 mg/kg/day in CSE KO mice at one week prior to TAC procedure and was continued up to 12 weeks following TAC. In addition, some C57BL/6J mice receiving SG-1002 diet were placed on the control diet at 1 week or 3 weeks following TAC.

Echocardiography

At 2 days prior to TAC procedure, baseline transthoracic echocardiogram was performed using 30-MHz probe on a Vevo 2100 (Visualsonics) under anesthesia with isoflurane (0.25 to 0.50%) supplemented with 100% $O_2$. Following TAC procedure, echocardiography was also performed in the same manner for up to 12 weeks. To determine cardiac structure and function, intraventricular septal end diastolic dimension (IVSd), LV end diastolic dimension (LVEDD), LV end systolic dimension (LVESD), and LV ejection fraction (LVEF) were analyzed from M-mode images.

Measurement of Hydrogen Sulfide and Sulfane Sulfur

Hydrogen sulfide and sulfane sulfur levels were measured in heart and blood according to methods known in the art. For heart tissue, the amount of $H_2S$ is reported as nmol/mg wet weight. For the blood, the amount of $H_2S$ is reported as μm.

Western Blot Analysis

Western blot analysis was performed as described in Li et al., *Annu. Rev. Pharmacol. Toxicol.* 51:169-187, 2011. Equal amounts of protein were loaded into lanes of polyacrylamide-SDS gels. The gels were electrophoresed, followed by transfer of the protein to a PVDF membrane. The membrane was then blocked and probed with primary antibodies overnight at 4° C. Immunoblots were next processed with secondary antibodies (anti-rabbit, anti-chicken, or anti-mouse, Cell Signaling) for 1 hour at room temperature. Immunoblots were then probed with an ECL+Plus chemiluminescence reagent kit (GE Healthcare) to visualize signal, followed by exposure to X-ray film (Denville Scientific). The film was scanned to make a digital copy and densitometric analysis was performed to calculate relative intensity with ImageJ software from the National Institutes of Health (version 1.40 g) using the Rodbard function. The membranes were incubated with the phospho-specific antibody first. Membranes were then stripped and incubated with the total-specific antibody. Results are presented as the ratio of the expression of phosphorylated protein to total protein. All experiments were performed in triplicate. For each membrane the relative intensity of each band was normalized to the value of the weakest band (smallest intensity). The values for each individual sample were averaged to obtain one value for each sample. The values for each group were then averaged and subsequently normalized to the mean of the control group (Sham).

Myocardial Measurement of NO Metabolites

Nitrite ($NO_2^-$) and nitrate ($NO_3^-$) analysis of cardiac tissue was determined by ion chromatography (ENO20 Analyzer, Eicom) as previously described in Li et al., *Annu. Rev. Pharmacol. Toxicol.* 51:169-187, 2011.

Serum Measurements of VEGF and BNP

Serum levels of VEGF (VEGF ELISA kit, R&D Systems) and brain natriuretic peptide (BNP) (BNP EIA kit, Phoenix Pharmaceuticals, Inc.) were determined by ELISA at 6 and/or 12 weeks following TAC.

Cardiac Mitochondrial Respiration Assay

The myocardial mitochondria were isolated and mitochondrial respiratory capacity was assessed using methods known in the art. Mice were euthanized by cervical dislocation, and hearts were quickly excised and placed in ice-cold isolation buffer (300 mM sucrose, 20 mM Tris, 2 mM EGTA, 1 mM ATP, 5 mM $MgCl_2$, and 1% fat free BSA). Hearts were finely chopped and homogenized with a Tissue Tearor (Biospec Products, Bartlesville, Okla.) on low to medium speed for ~10 s. Homogenates were centrifuged for 3 min at 2,500 rpm. The supernatant was collected and centrifuged for 5 min at 9,000 rpm. The supernatant was discarded, and the pellet was resuspended in isolation buffer and centrifuged for 5 min at 10,000 rpm and repeated two additional times. The final pellet was suspended in 100 μL isolation buffer. Protein concentration was determined by a Lowry protein assay kit (Bio-Rad Laboratories, Hercules, Calif.). The $O_2$ consumption of isolated mitochondria (500 μg/mL) was monitored using a Clark-type oxygen electrode (Hansatech Instruments, Amesbury, Mass.). Mitochondria were incubated in respiration buffer (100 mM KCl, 25 mM sucrose, 5 mM $KH_2PO_4$, 1 mM $MgCl_2$, 1 mM EGTA, 10 mM HEPES, 10 mM glutamate, and 2.5 mM malate), and the respiratory capacity was assessed by measuring state 3 (i.e., ADP-dependent) and state 4 (i.e., ADP-independent) respiration. The respiratory control ratio (RCR) was calculated as the ratio of state 3 and state 4 respiration rates.

8-Isoprostane Assay

Concentrations of 8-isoprostane in the plasma and heart were determined by 8-isoprostane EIA kit according to manufacture instruction (Cayman Chemicals, Michigan).

Histology

For histological analysis, hearts were collected at the indicated times, fixed in 10% buffered formalin, and embedded in paraffin. Serial 5 μm heart sections from each group were stained with Masson's trichrome and Picrosirius Red (to detect fibrosis). Digital images of the slides were then captured and analyzed using ImageJ. For each heart, we analyzed multiple sections taken from the mid-ventricle and then averaged these numbers to obtain a single % fibrosis/LV measurement for each animal.

Statistical Analysis

All data are expressed as mean±SEM. Statistical significance was evaluated using unpaired Student's t test for comparison between 2 means and ANOVA (1-way or 2-way) for comparison among 3 or more means using Prism 5 (Graph Pad Software Inc). For the ANOVA, if a significant result was found, the Tukey (1-way ANOVA) or Bonferroni (2-way ANOVA) test was used as the posthoc analysis. For all data, a value of $p<0.05$ denotes statistical significance.

Clinical Studies and Statistical Analysis

A prospective, randomized, double blind study evaluated and approved by the Ethics Committee of the Universidad Autónoma de Nuevo León University Hospital (Monterrey, Mexico) with registration number BR09-001 was conducted. The study included patients who attended the Reproductive Biology Clinic of the University Hospital from July 2009 to September 2010 who desired to be pregnant and met the inclusion criteria. Patients between 20 and 45 years of age with a diagnosis of idiopathic oligoasthenozoospermia wishing to participate in the study after signing informed consent were included. The diagnosis of oligoasthenozoospermia was reached by performing two semen analyses on different dates with an interval of three weeks in between. To make the diagnosis, the results of the semen analyses needed to report less than 25% type A sperm motility or less than 50% type A+B sperm motility as detailed in the World Health Organization Laboratory Manual for the Examination of Human Semen and Semen-Cervical Mucus Interaction, $4^{th}$ ed. New York: Cambridge University Press, 1999. Type A Motility comprised rapid progression; type B motility comprised medium progression; type C mobility comprised slow or clumsy progression; and type D mobility comprised immotile. Oligozoospermia was defined as a concentration of less than 20 million sperm per milliliter, according to the criteria of the World Health Organization. Oligoasthenozoospermia was defined as the presence of oligozoospermia and asthenozoospermia in the same patient. In each semen analysis, morphology was manually assessed using Kruger strict criteria.

Infertile patients with normal findings on semen analysis, patients who were chronic smokers or those who had been taking antioxidants in the last 6 months prior to study entry were excluded. Patients with chronic degenerative diseases such as diabetes or high blood pressure or with hormonal abnormalities were also excluded. All study subjects who did not comply with medication given as prescribed, who discontinued the drug or were hypersensitive to it were eliminated.

A complete medical history and physical examination was obtained for all patients. All study participants underwent a second semen analysis to confirm the diagnosis after a sexual abstinence of 3 to 5 days. This semen analysis was considered baseline (sample 1). On a second visit this new semen analysis was reviewed to confirm oligoasthenozoospermia and one of the 3 substances to be taken was randomly prescribed for 75 days. The substances given were 1.5 g of hydrogen sulfide prodrug as an antioxidant, 50 mg of resveratrol as an antioxidant, and 1.5 g of microcrystalline cellulose as a placebo.

Randomization of the substance given to each patient was performed by placing in a drawer at random all the containers having exactly the same color, size, and shape with the three separate substances (hydrogen sulfide prodrug, resveratrol, and placebo) without any kind of reference as to the content. Each container had a label with a serial number. The attending physician and the patient were unaware of the contents of the container. A third researcher had a log and database for each label and the contents of the container. Each patient was asked to take a container at random and the container number was recorded in the patient's medical record. At the end of the study, before statistical analysis, we obtained the relationship between the numbers on the labels and the contents, grouping patients according to the substance. Each patient was given a treatment adherence form (a patient log) in order to count the days of medication and record adverse events, if these occurred, including the type and frequency.

The patients were scheduled one month after starting treatment (third visit) in order to document adverse effects and adherence to treatment. If the patient did not attend the event data were collected by phone.

In the next scheduled consultation (fourth visit), carried out 75 days after starting treatment; adherence was verified and adverse effects were reported. For this visit, the patients presented with 3 to 5 days of sexual abstinence for post-treatment semen analysis (sample 2). Sperm concentration and motility were evaluated, and carried out entirely with an automated IVOS (Integrated Visual Optical System) device and manually confirmed by lab technicians, who were blinded to the treatment group that each patient in. The morphology of each semen analysis was manually assessed, according to Kruger criteria.

Traditional descriptive data, such as measures of central tendency (means, median and mode) and in the case of quantitative variables, measures of dispersion (variance, standard deviation and coefficient of variation) were studied for each variable, together with the frequencies observed in qualitative variables.

The study subjects were divided according to the group assigned and the statistical variables mentioned were analyzed. The results of each variable by group using hypothesis tests for means ($x^2$) and proportions, according to each type of variable (quantitative and qualitative, respectively) at a confidence interval of 95%, with a statistically significant $p<0.05$, were also compared and evaluated.

Example 1

Sulfide Levels are Declined after Heart Failure in Patients and Mice

Previous studies suggest that both exogenous and endogenously derived $H_2S$ exhibit potent cytoprotective effects in models of acute myocardial I/R and ischemia-induced heart failure. However, the role of endogenous $H_2S$ in pressure overload-induced heart failure has not been fully elucidated. In the current study, a number of novel findings regarding the role of CSE-derived $H_2S$ on the severity of heart failure following TAC have been identified and important insights into the mechanism by which oral $H_2S$ therapy attenuates TAC-induced heart failure are provided.

Figure 1B:
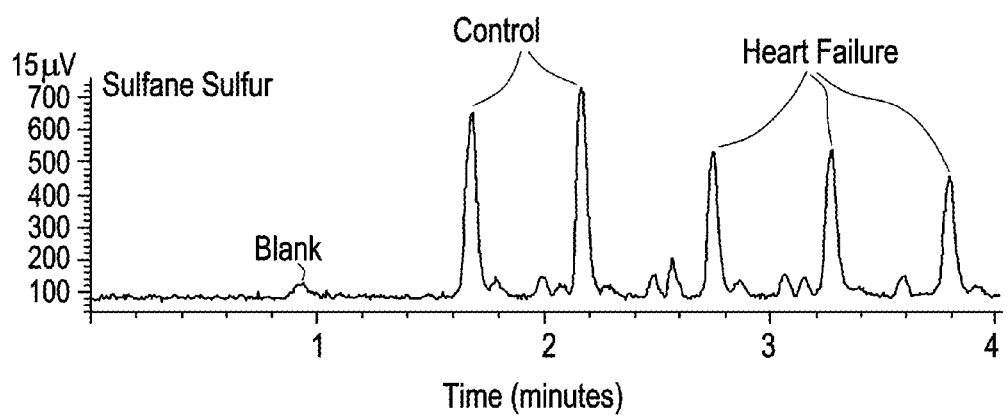
Figure 1C:
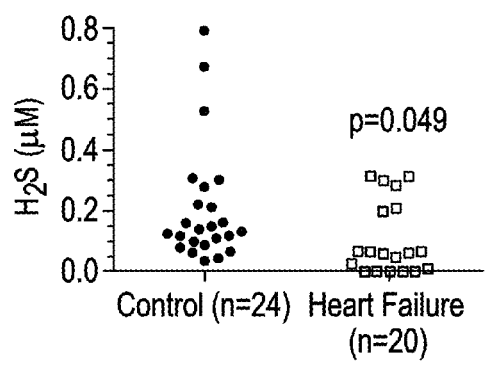
Figure 1D:
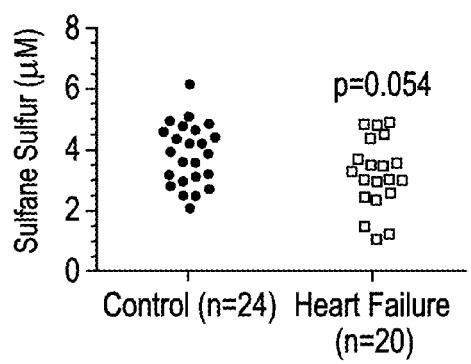
Figure 1E:
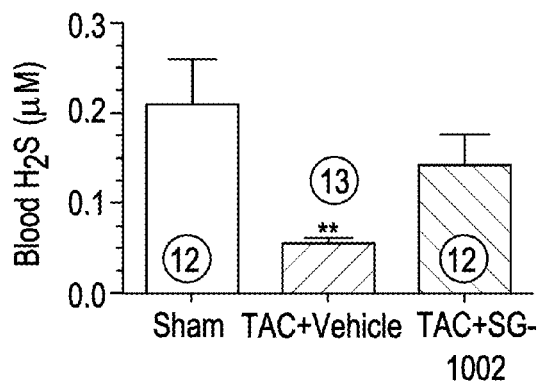
Figure 1F:
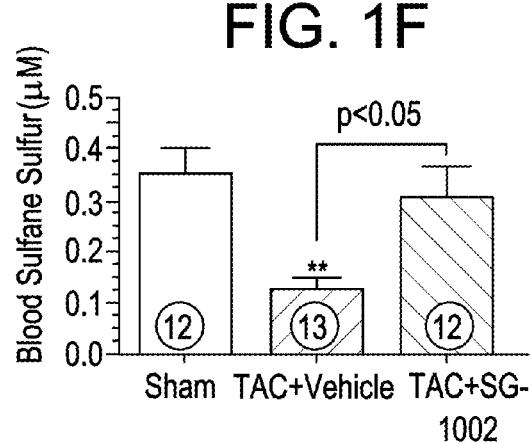
Figure 1G:
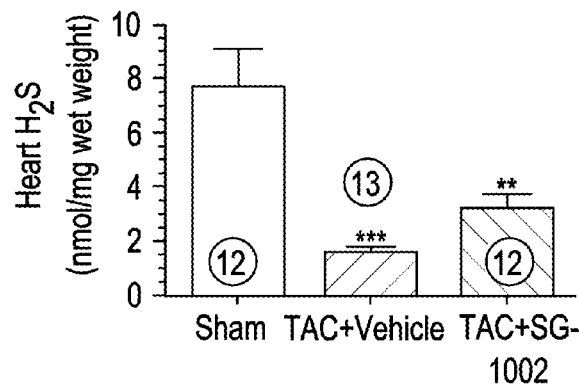
Figure 1H:
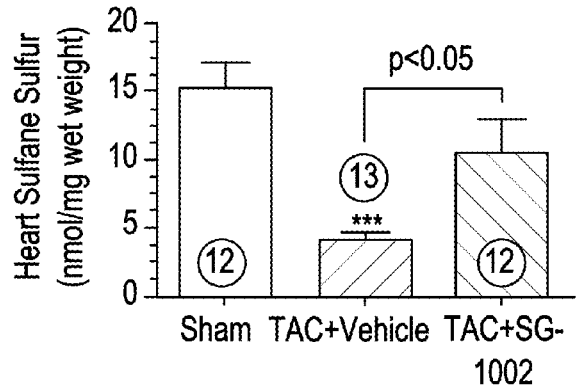
Figure 8A:
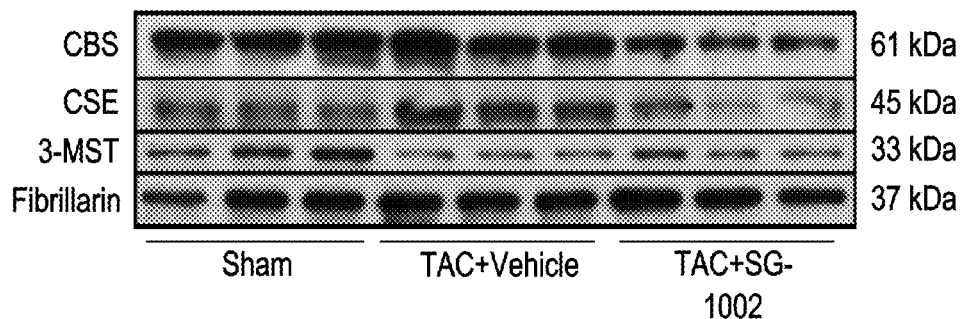
FIGS. 8A-8D.
Figure 8B:
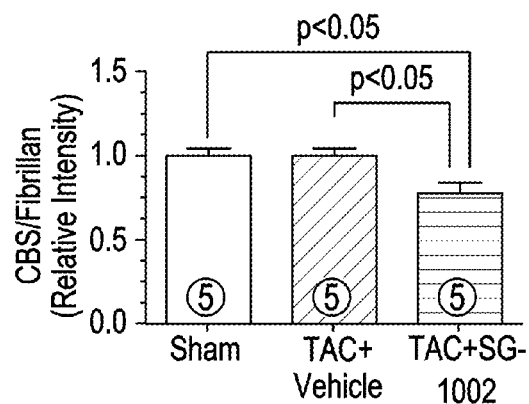
Figure 8C:
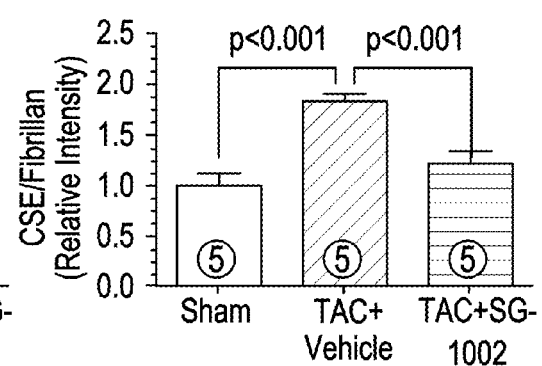
Figure 8D:
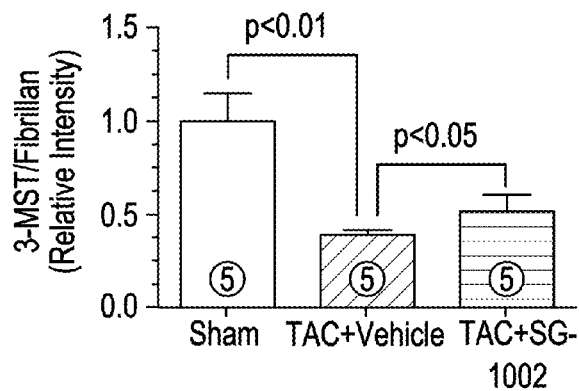
Figure 9A:
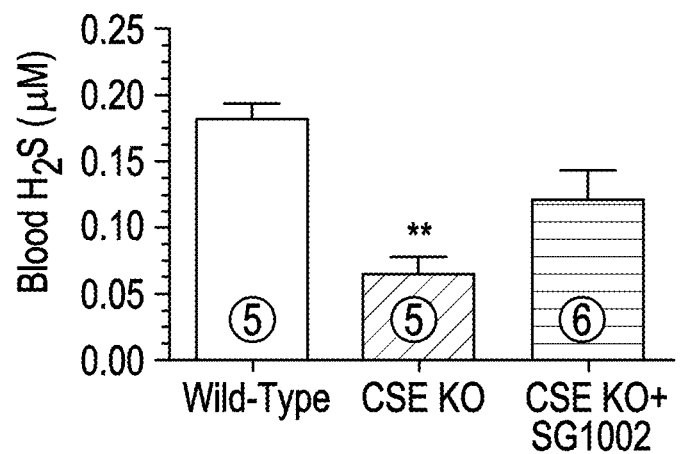
FIGS. 9A-9D.
Figure 9B:
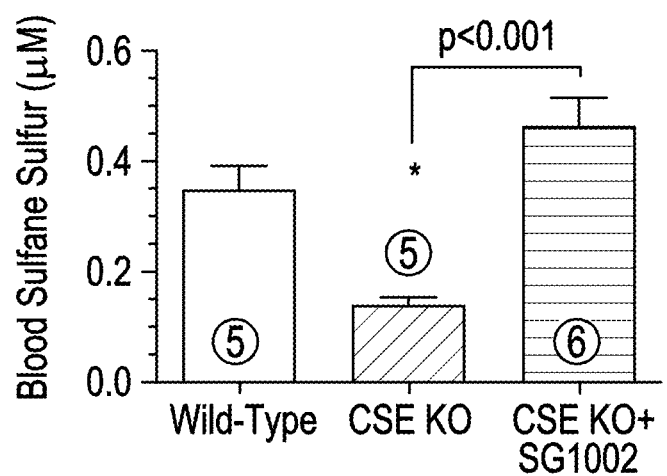
Figure 9C:
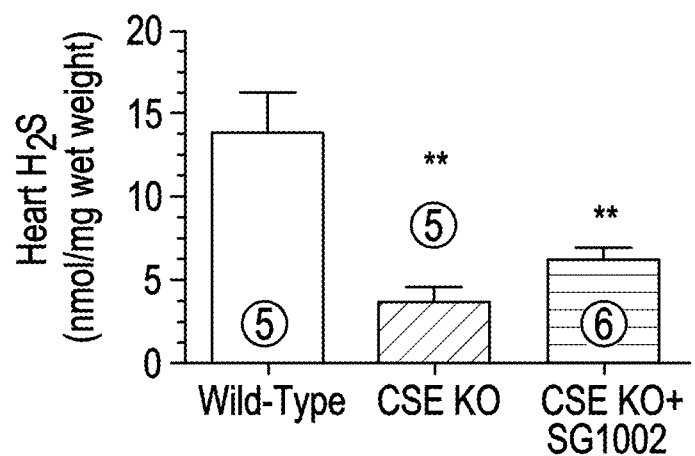
Figure 9D:
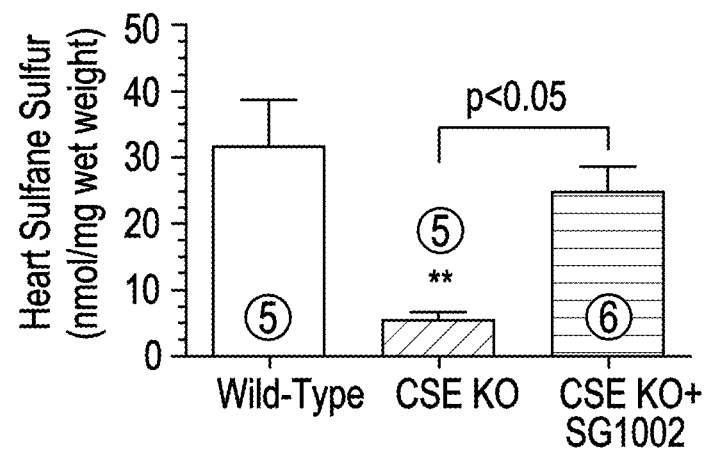

Circulating sulfide levels (free $H_2S$ and sulfane sulfur) in 20 heart failure patients and 24 aged-matched controls were examined. The detailed description of these patients is given in Table 7. As shown by the representative gas chromatograph peaks and summarized data in FIGS. 1A and 1C, free $H_2S$ levels were significantly lower in the heart failure patients as compared to the controls (p=0.049), whereas sulfane sulfur levels trended to be lower in the heart failure patients FIGS. 1B and D; p=0.054). Next, the effects of TAC-induced heart failure on the myocardial expression of the three known $H_2S$-producing enzymes were examined, as well as the levels of circulating and myocardial sulfide levels at 6 weeks of TAC. The analysis revealed that the expression of CBS was unaltered (FIGS. 8A and 8B). However, CSE expression was upregulated in the vehicle mice compared to the sham (FIGS. 8A and 8C; p<0.001), whereas 3-MST expression was significantly downregulated compared to Sham levels (FIGS. 8A and 8D; p<0.01). Interestingly, free $H_2S$ and sulfane sulfur levels were significantly lower in the blood (p<0.01) and heart (p<0.001) of TAC+Vehicle mice when compared to Sham-operated mice (FIGS. 1E-1H).

TABLE 7

|  | Control | Heart Failure |
|---|---|---|
| Number | 24 | 20 |
| Age (average years) | 51 ± 10 | 53 ± 13 |
| Gender |  |  |
| Males (%) | 16 (67%) | 18 (90%) |
| Females (%) | 8 (33%) | 2 (10%) |
| NYHA Classification |  |  |
| III (%) | — | 5 (25%) |
| IIIb (%) | — | 2 (10%) |
| IV (%) | — | 13 (65%) |

Example 2

CSE Deficiency Exacerbates Cardiac Dysfunction Following TAC

Figure 2A:
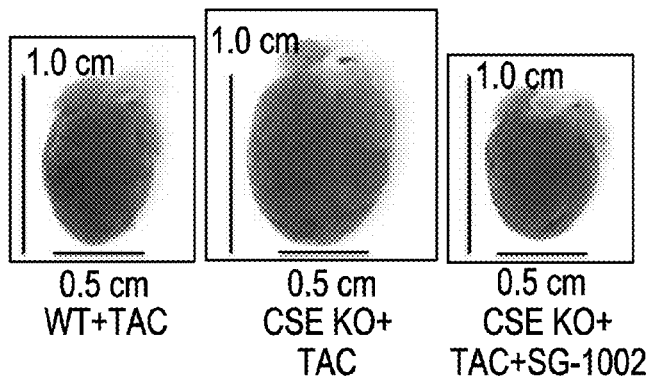
FIGS. 2A-2F are data showing that deficiency of cystathionine gamma lyase (CSE) exacerbates cardiac dysfunction following TAC.
Figure 2B:
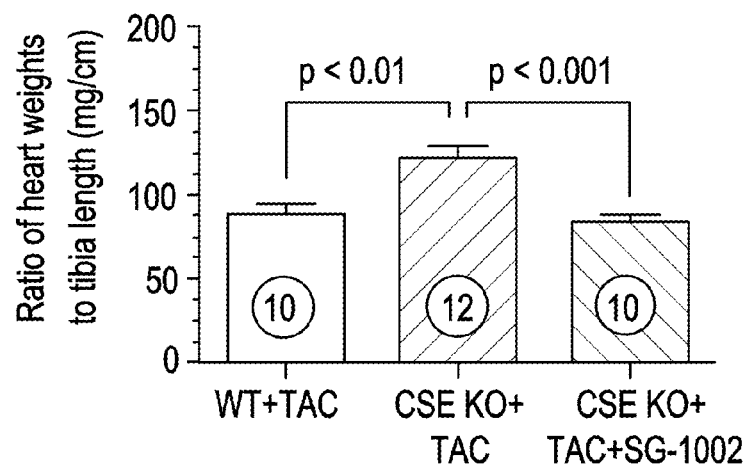
Figure 2B:
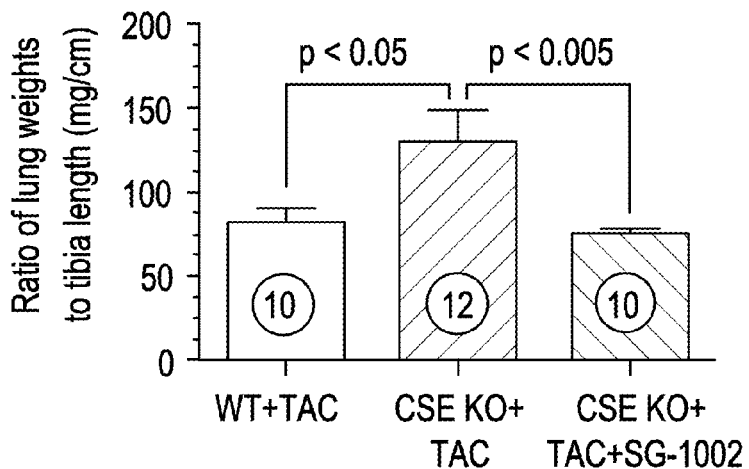
Figure 2C:
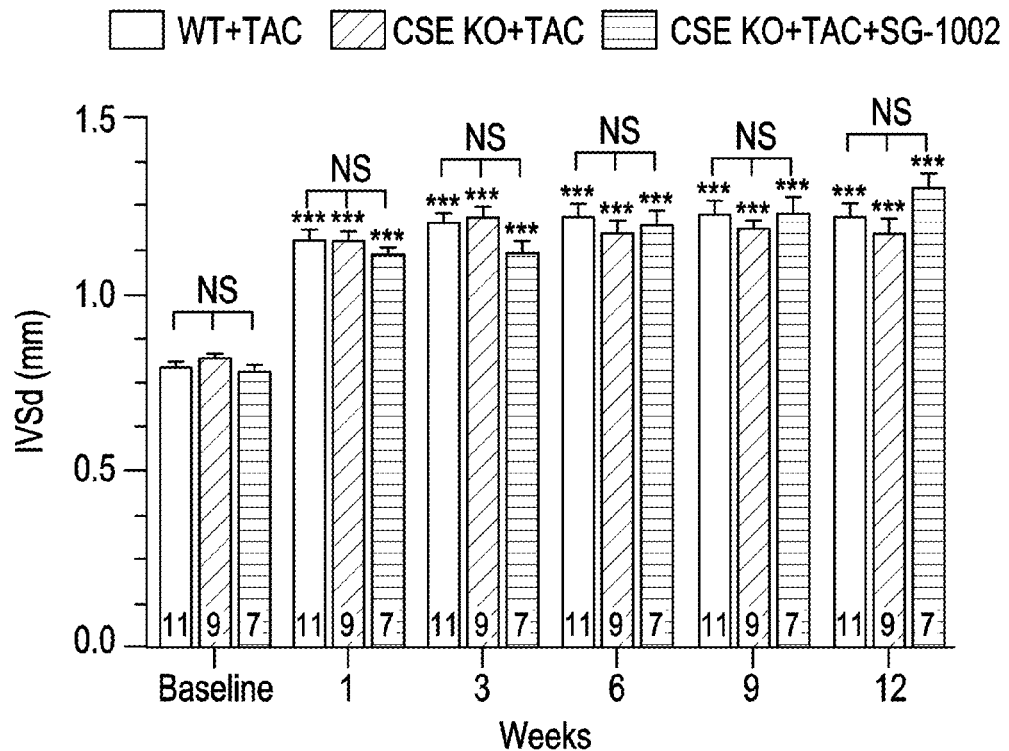
Figure 2D:
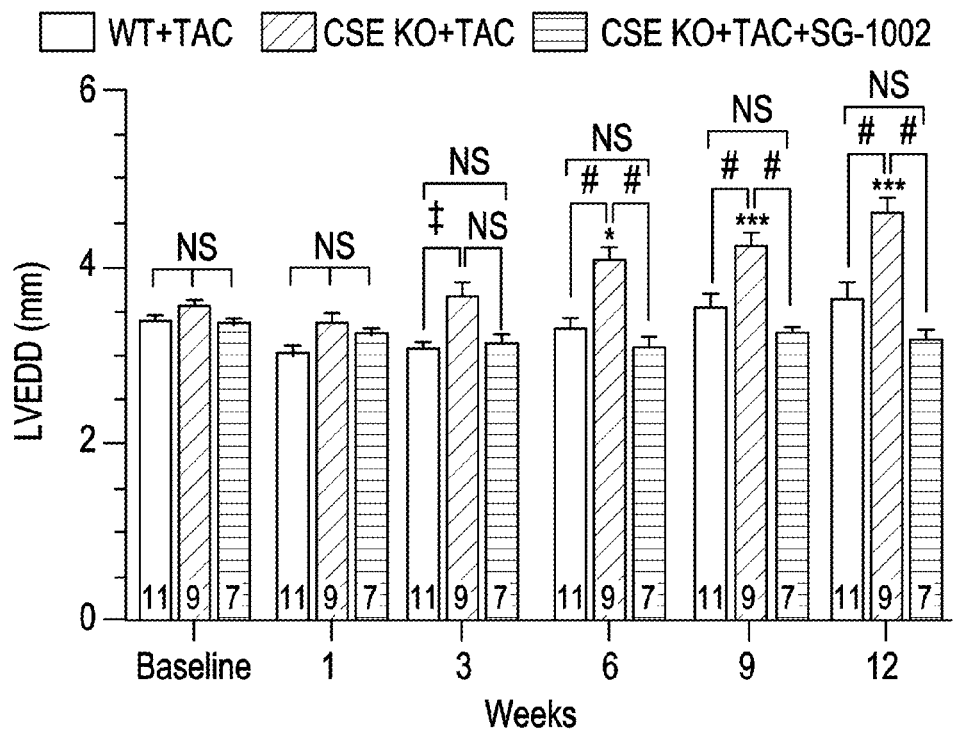
Figure 2E:
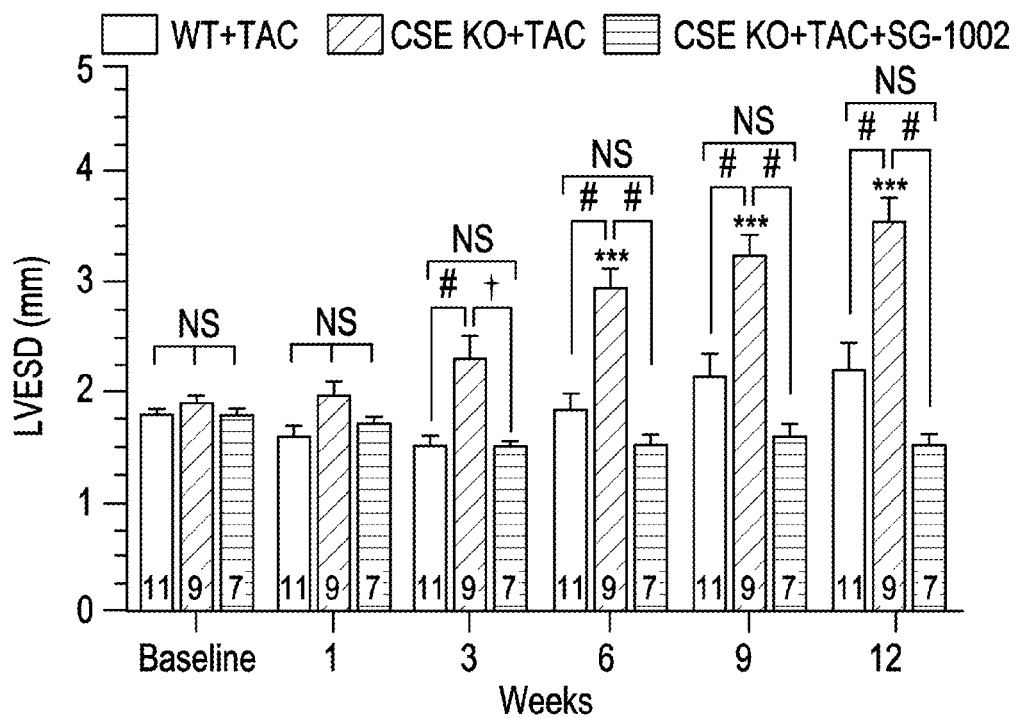
Figure 2F:
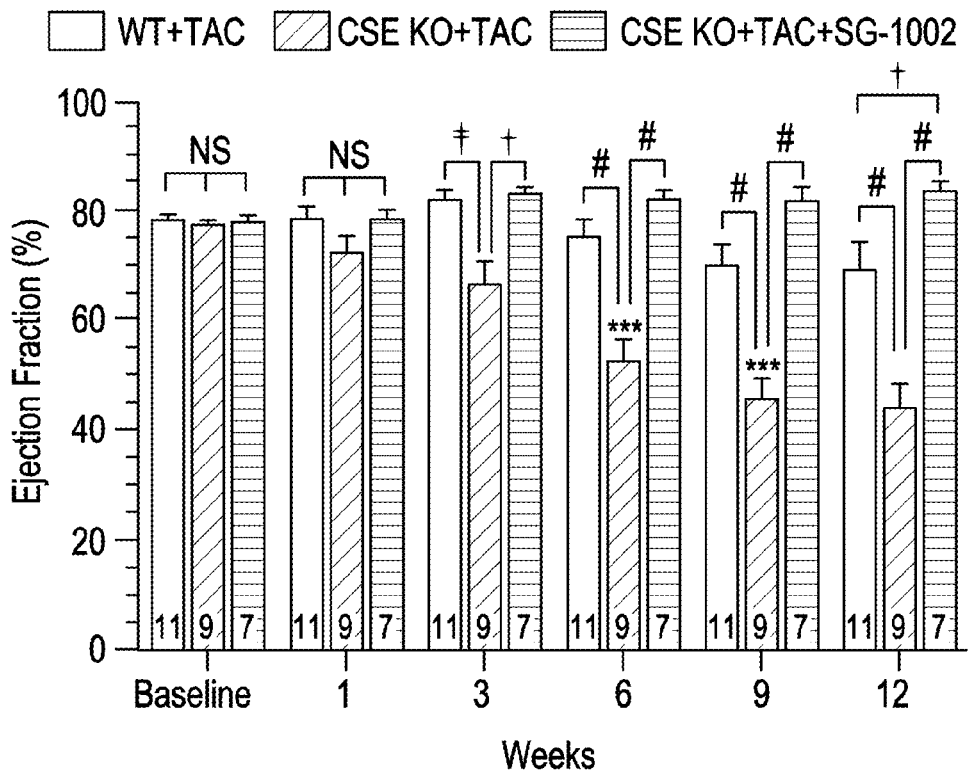
Figure 10A:
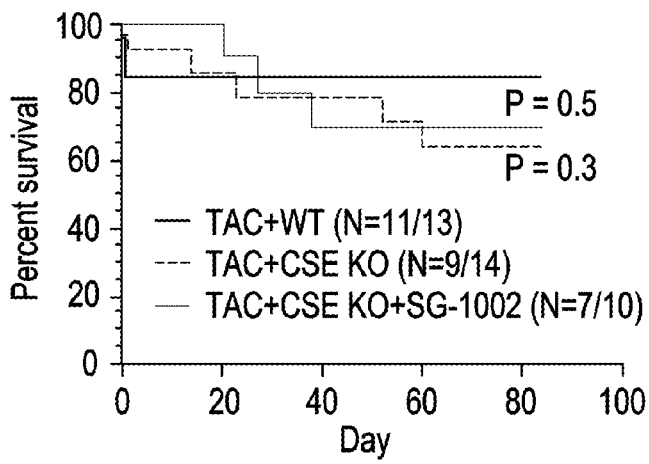
FIGS. 10A-10C.

To investigate the role of endogenous $H_2S$ in pressure overload, we performed TAC surgery in CSE KO mice and evaluated cardiac structure and function using echocardiography were performed. Initially, it was confirmed that CSE KO mice exhibited lower free $H_2S$ and sulfane sulfur levels in the blood and heart compared to WT mice (FIGS. 9A-9D; p<0.05). CSE KO mice exhibited significantly greater cardiac enlargement and pulmonary edema at 12 weeks following TAC compared to WT mice (FIGS. 2A-2B). Both groups showed similar degrees of increased IVSd thickness from 1 week to 12 weeks following TAC (FIG. 2C). However, CSE KO mice exhibited significant LV cavity dilatation, as seen by increases in both LVEDD and LVESD, and exhibited exacerbated cardiac dysfunction from 3 weeks to 12 weeks following TAC compared to WT mice (FIGS. 2D-2F). Despite the increased cardiac structure and functional changes in the CSE KO mice, no difference in the mortality was observed after TAC when compared to the WT mice (FIG. 10A).

Example 3

Figure 3A:
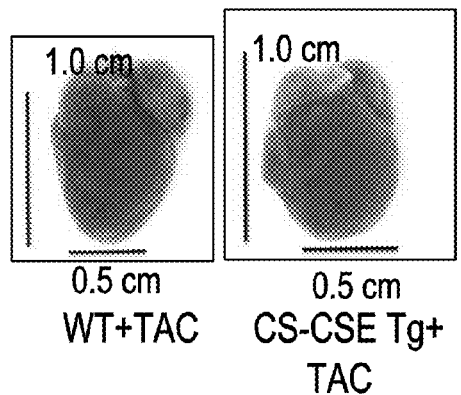
FIGS. 3A-3F are data showing cardiac specific overexpression of CSE attenuates cardiac dilatation and cardiac dysfunction following TAC.
Figure 3B:
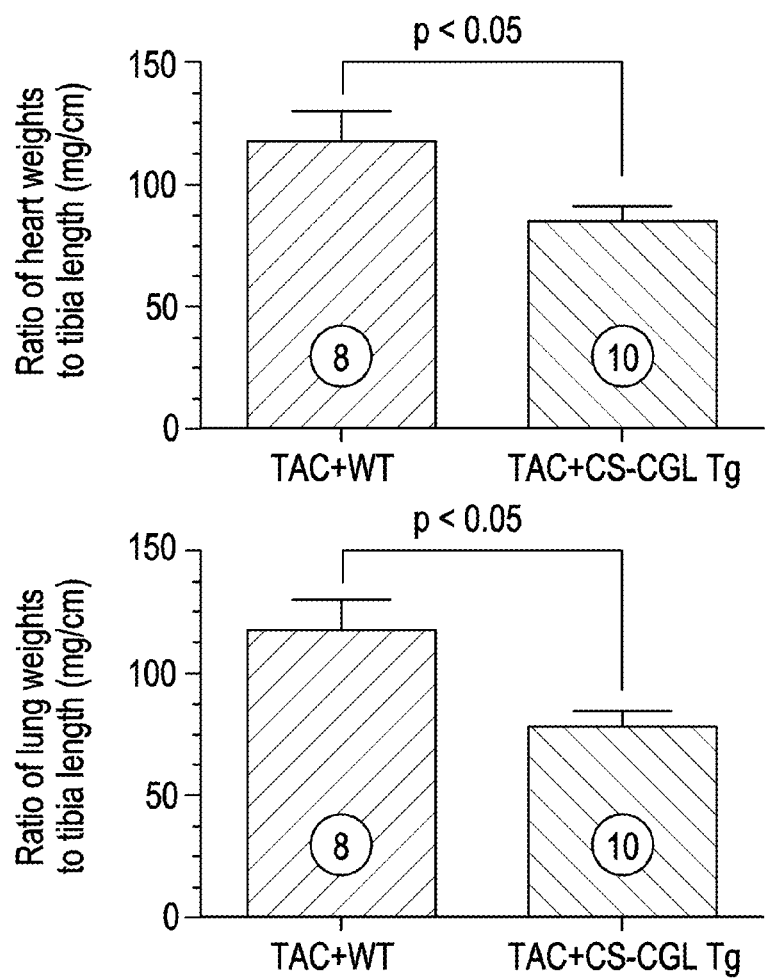
Figure 3C:
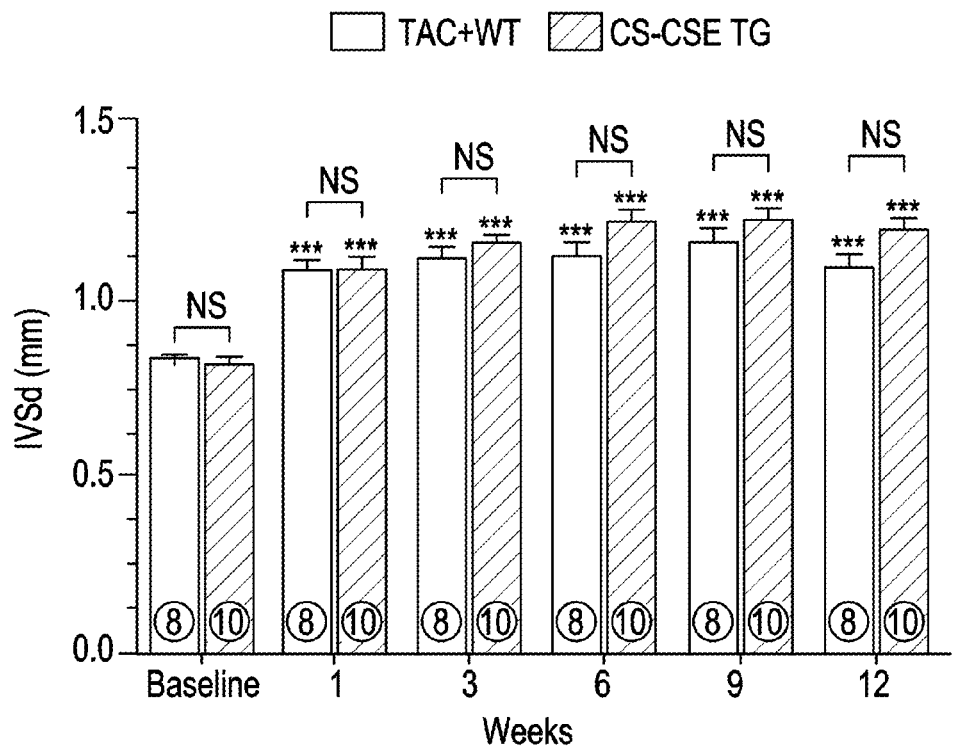
Figure 3D:
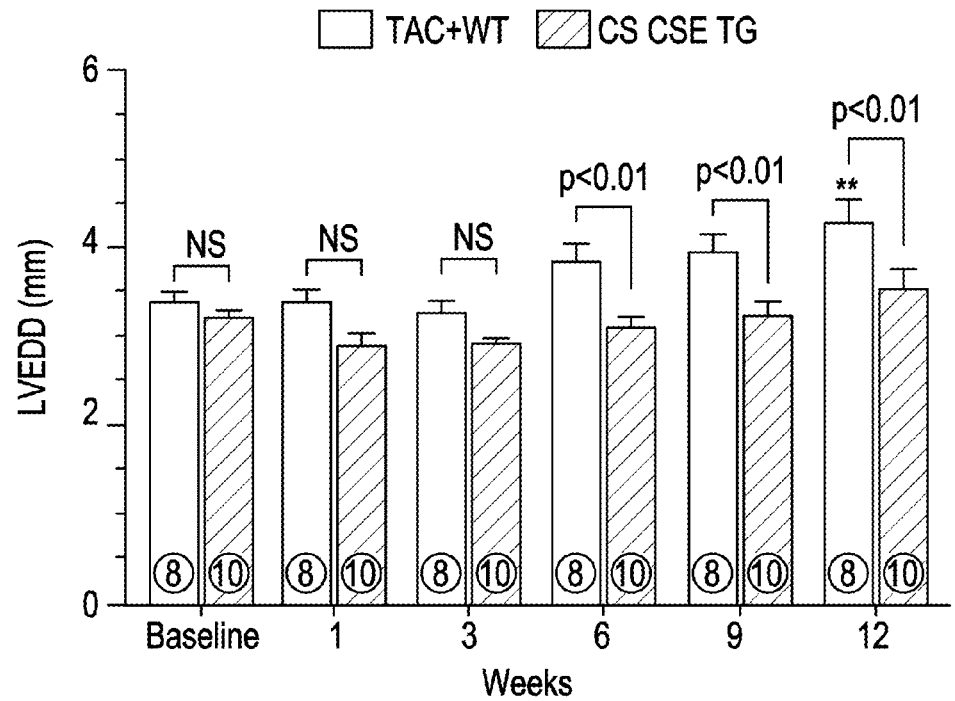
Figure 3E:
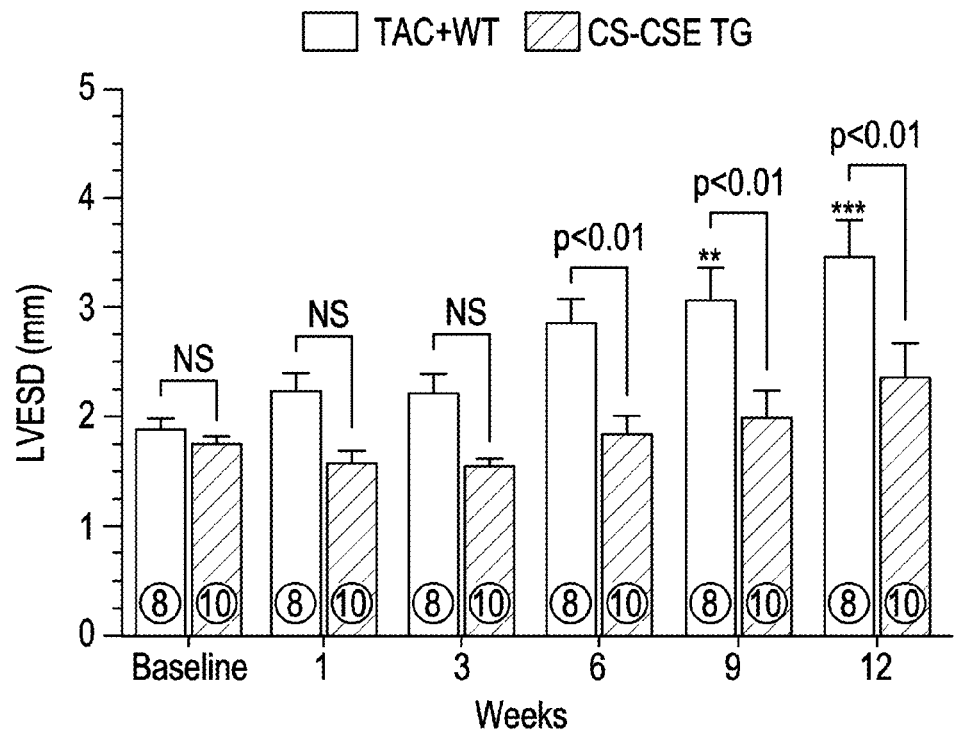
Figure 3F:
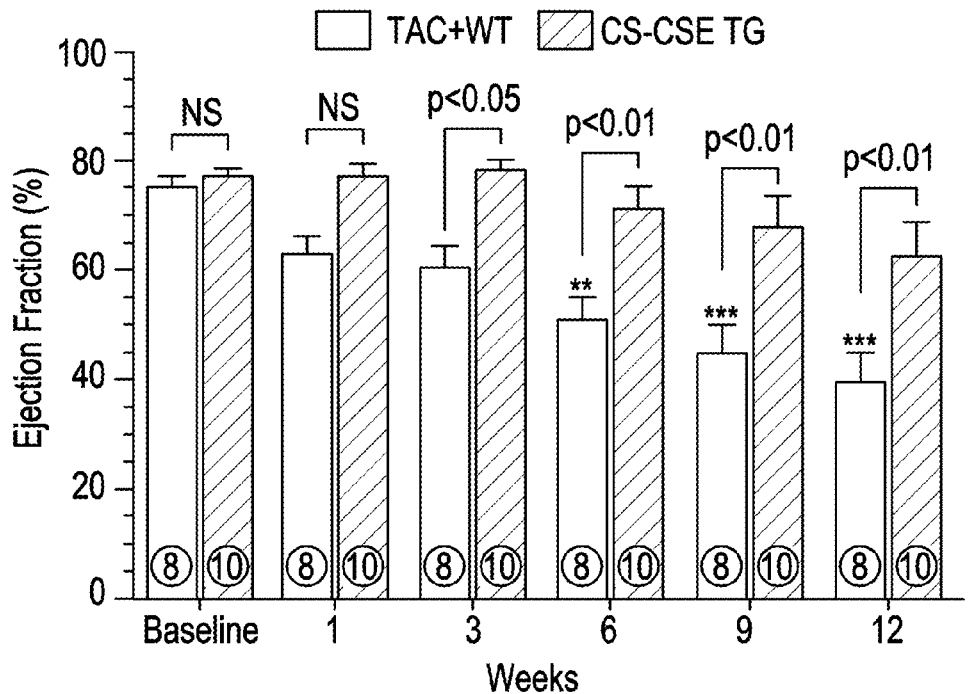
Figure 10B:
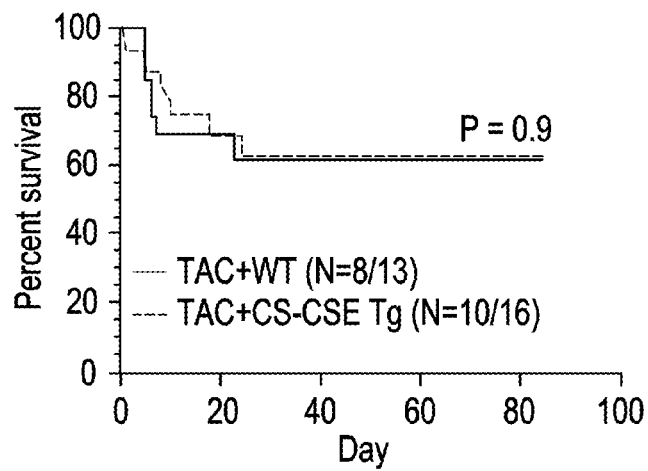
Figure 11:
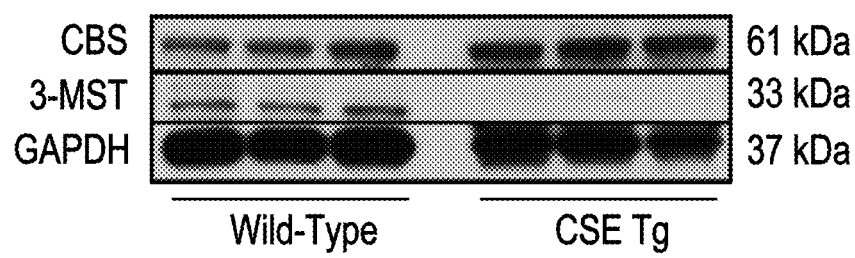
FIG. 11 is representative immunoblots of cystathionine beta synthase (CBS), and 3-mercaptopyruvate sulfutransferase (3-MST) from the hearts of Wild-type and CS-CSE transgenic mice.

Myocardial Overexpression of CSE Attenuates Cardiac Dysfunction without Preventing Cardiac Hypertrophy Following TAC Overexpression of CSE has been shown to increase $H_2S$ production in the heart without alteration in CBS expression. In the present studies, no alteration in cardiac CBS expressions in CS-CSE Tg mice were observed, but CS-CSE Tg mice exhibited less 3-MST expression compared to WT mice (FIG. 11). It was examined whether overexpression of CSE specifically within the cardiac myocyte would attenuate cardiac hypertrophy and/or dysfunction following TAC using CS-CSE Tg mice. CS-CSE Tg mice exhibited significantly less cardiac enlargement and pulmonary edema, as assessed by the ratio of heart and lung weights to tibia length (mg/cm) when compared to WT controls (FIGS. 3A-3B). Furthermore, echocardiography analysis revealed that while CS-CSE Tg mice exhibited no difference in IVSd thickness when compared to WT mice, they did exhibit less cardiac dilatation and dysfunction from 6 weeks to 12 weeks following TAC (FIGS. 3C-3F). Again, no difference in mortality was observed between the two groups (FIG. 10B).

Together, this data indicates that endogenous $H_2S$ generated enzymatically by CSE plays an important role in the maintenance of cardiac function following pressure overload-induced hypertrophy independently of the regulation of cardiac myocyte hypertrophy.

Example 4

Figure 4A:
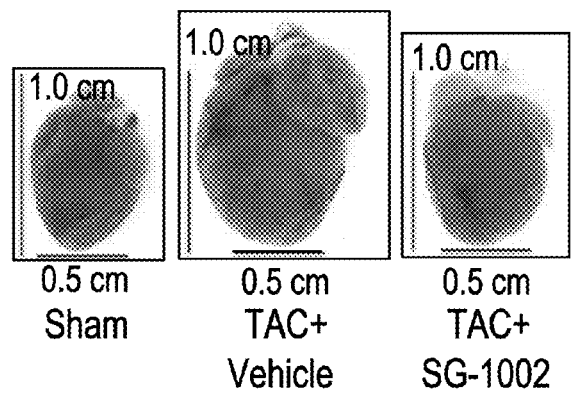
FIGS. 4A-4H are data showing exogenous $H_2S$ therapy prevents cardiac dilatation and dysfunction following TAC.
Figure 4B:
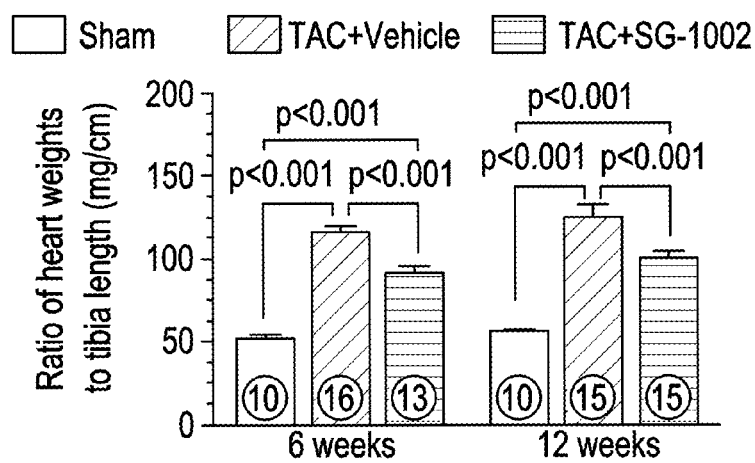
Figure 4C:
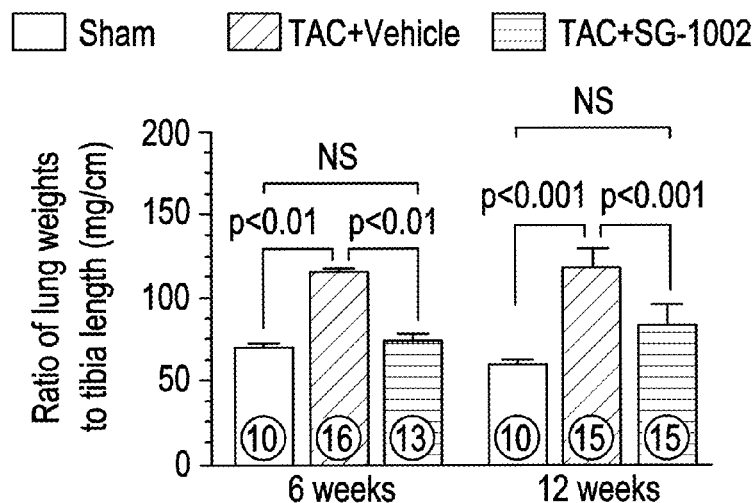
Figure 4D:
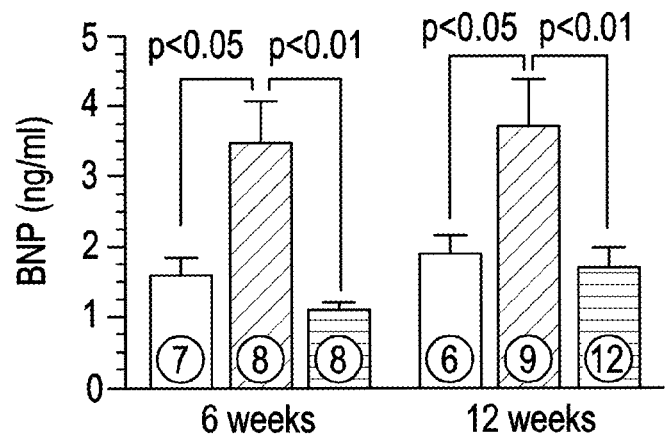
Figure 4E:
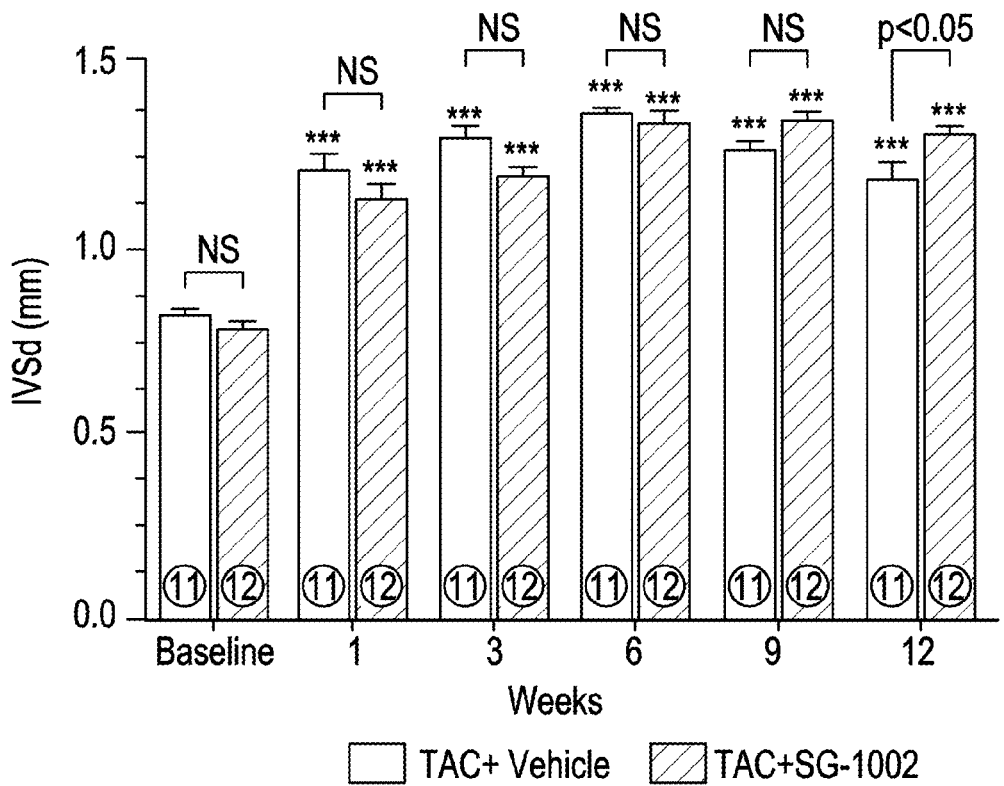
Figure 4F:
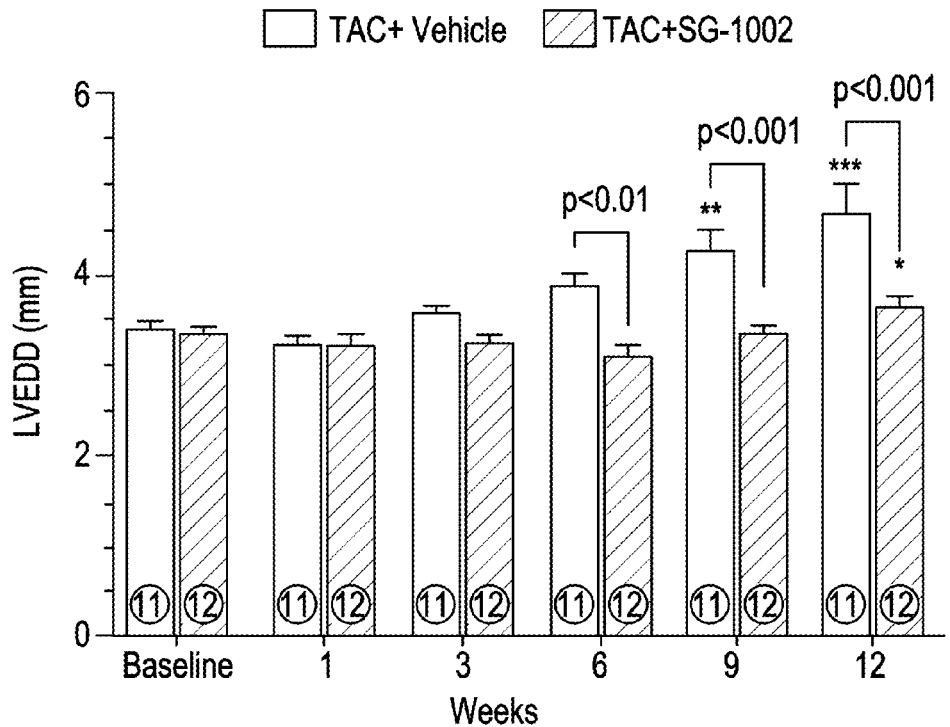
Figure 4G:
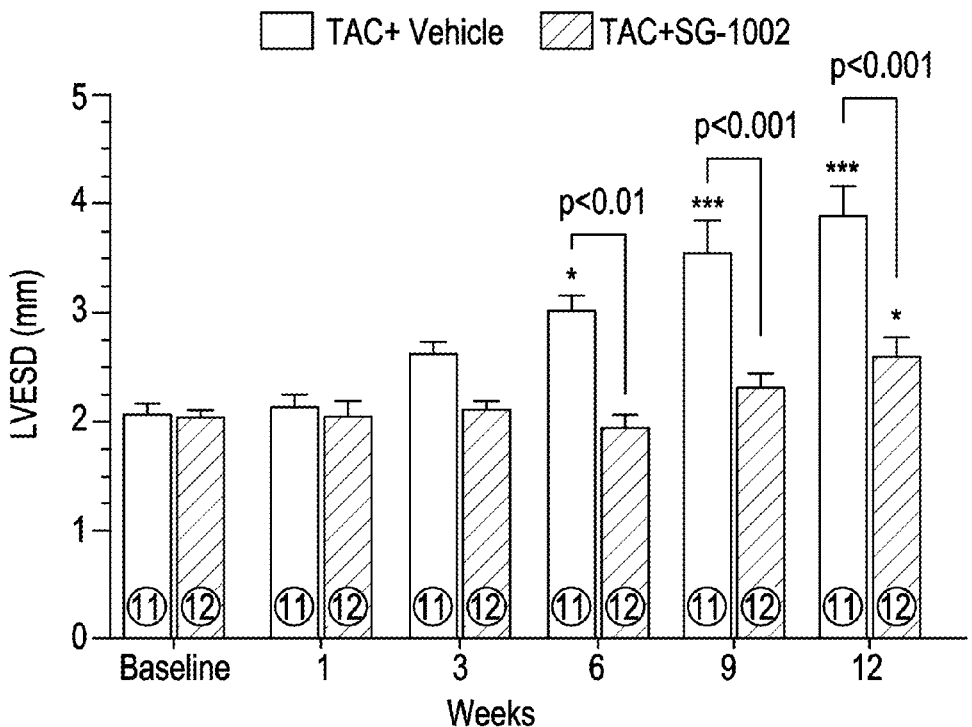
Figure 4H:
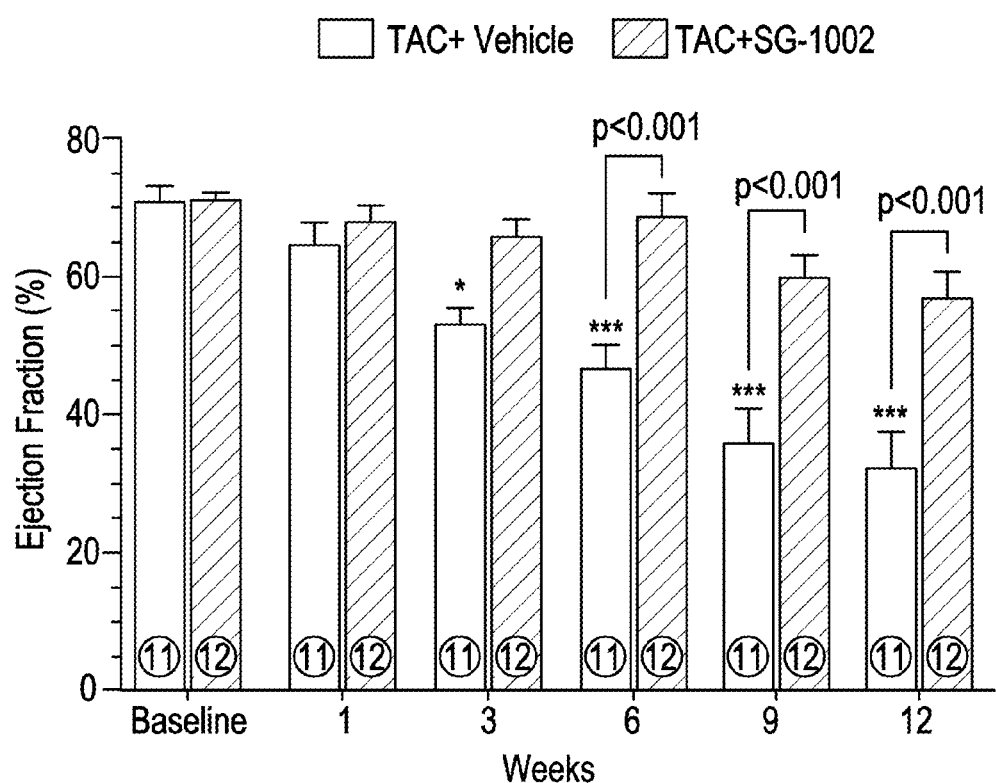
Figure 5A:
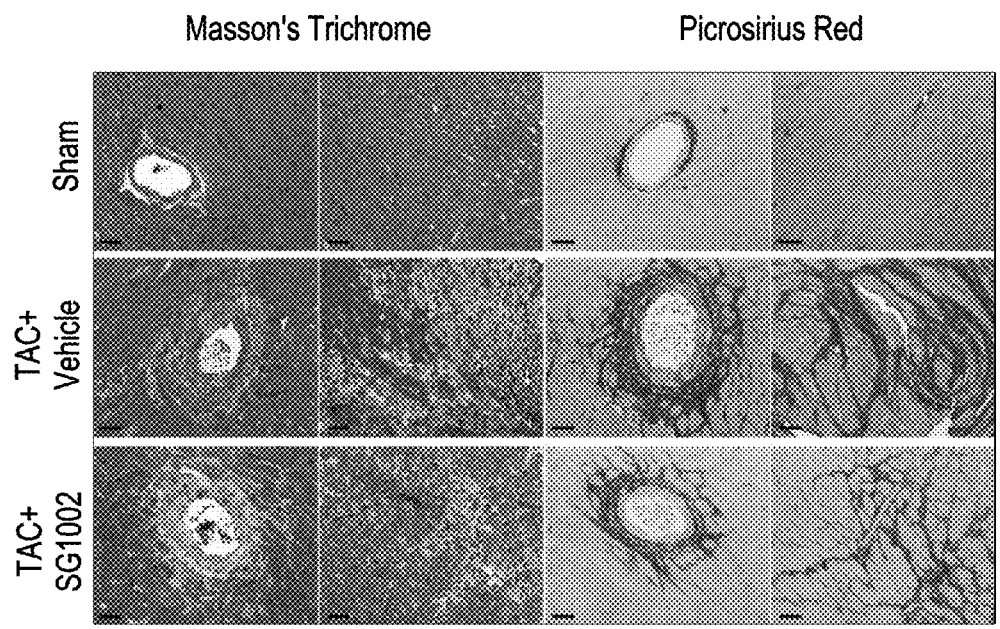
FIGS. 5A-5C are data showing $H_2S$ attenuates the intermuscular and perivascular fibrosis following TAC.
Figure 5B:
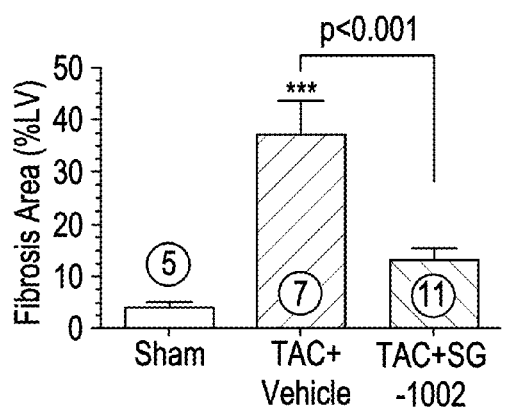
Figure 5C:
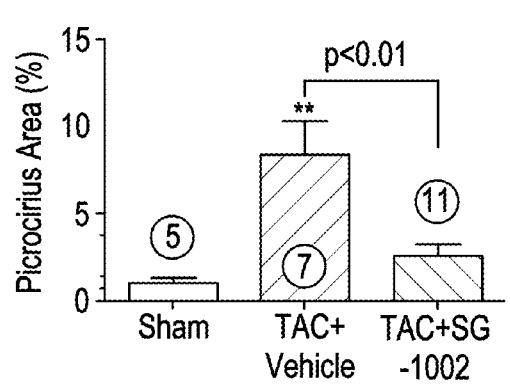
Figure 10C:
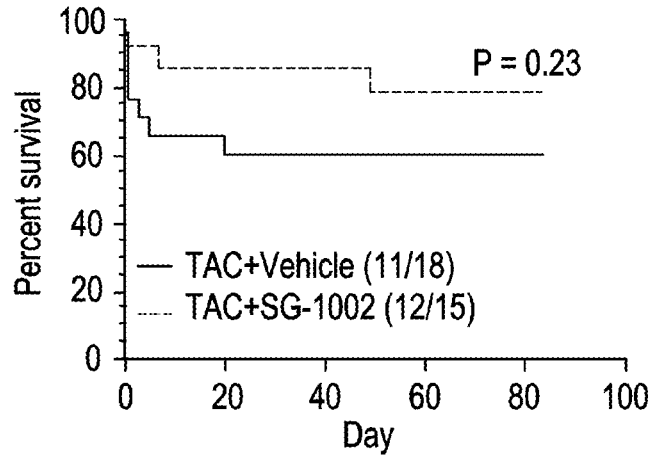

Administration of Exogenous $H_2S$ Prevents Cardiac Enlargement, Preserves LV Function, and Reduces Fibrosis Following TAC Next, the effects of administration of oral $H_2S$ therapy on pressure overload-induced cardiac hypertrophy and dysfunction (FIGS. 4A-4H) were examined in wild-type C57BL/6J mice. For these experiments we administered SG-1002 (20 mg/kg/day) in the chow. Initial studies found that SG-1002 treatment partially restored free $H_2S$ and significantly restored sulfane sulfur levels in the blood (FIGS. 1E-1F; $p<0.05$ vs. TAC+Vehicle) and heart (FIGS. 1G-1H; $p<0.05$ vs. TAC+Vehicle). Gross morphologic analysis at 12 weeks following TAC, revealed that hearts from vehicle mice enlarged to a greater extent compared to SG-1002 treated mice (FIG. 4A). This was confirmed by heart weight/tibia length ratios, which found that the hearts of both vehicle and SG-1002 treated mice, were significantly increased compared to Sham mice at 6 and 12 weeks following TAC (FIG. 4B; $p<0.001$). However, SG-1002 treated mice showed significantly less of an increase compared to vehicle mice (FIG. 4B; $p<0.001$). In addition, SG-1002 treated mice displayed significantly less pulmonary edema when compared to vehicle mice at both time points (FIG. 4C). Moreover, circulating BNP levels as an indication of heart failure severity following TAC were evaluated. BNP levels increased significantly ($p<0.01$) in vehicle mice at 6 and 12 weeks compared to sham mice, but SG-1002 treatment significantly inhibited BNP ($p<0.01$ vs. TAC+Vehicle) levels following TAC (FIG. 4D). Echocardiography analysis (FIG. 4F) revealed that SG-1002 treatment did not alter the increase in IVSd thickness following TAC (FIG. 4E), but did prevent cardiac dilatation (FIGS. 4F-4G; $p<0.01$ vs. TAC+Vehicle) and cardiac contractile dysfunction (FIG. 4H; $p<0.001$ vs. TAC+Vehicle) from 6 weeks to 12 weeks following TAC. Histological analysis of Masson's Trichrome and Picrosirius Red stained sections at 12 weeks following TAC revealed extensive areas of intermuscular and perivascular fibrosis in hearts from TAC+ Vehicle mice (FIGS. 5A-5C; $p<0.01$ vs. sham). Although fibrosis was evident in the sections taken from TAC+SG-1002 heart, it was significantly less when compared to the TAC+ Vehicle hearts ($p<0.001$ for Masson's Trichrome and $p<0.01$ for Picrosirius Red). Finally, SG-1002 treated mice exhibited a better, but not statistically significant improved survival rate compared to vehicle mice (80% vs. 61%, $p=0.23$) (FIG. 10C).

Further analysis revealed that the administration of SG-1002 to CSE KO mice slightly, but not significantly, increased free $H_2S$ levels in the blood and heart, whereas administration of SG-1002 did significantly increase sulfane sulfur levels in both the blood ($p<0.001$) and the heart ($p<0.05$) as compared to CSE KO mice fed a control diet (FIGS. 9A-9D). The administration of SG-1002 also completely diminished LV cavity dilatation in CSE KO mice when compared to CSE KO mice fed a control diet (FIGS. 2D-2E; $p<0.05$). Interestingly, SG-1002 treated CSE KO mice maintained cardiac ejection fraction following TAC as compared to not only control diet-fed CSE KO mice but also WT mice at 12 weeks following TAC (FIG. 2F; $p<0.001$ vs. CSE KO+TAC and $p<0.05$ vs. WT+TAC). However, no difference in mortality was observed between the CSE KO groups (FIG. 10A).

Together, the results up to this point indicate that endogenous $H_2S$ bioavailability is markedly attenuated in heart failure following pressure overload even though CSE and CBS expression levels are maintained or upregulated. Moreover, augmentation of $H_2S$ levels by genetic or pharmacological approaches prevents the transition from compensated to decompensated cardiac hypertrophy.

Example 5

Figure 12A:
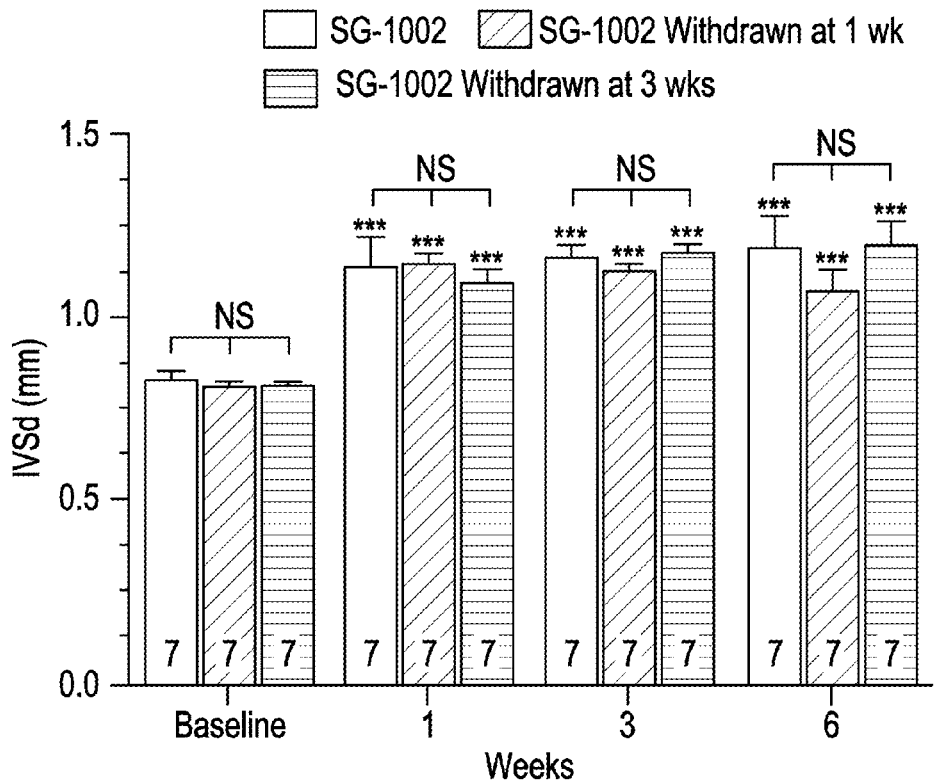
FIGS. 12A-12D.
Figure 12B:
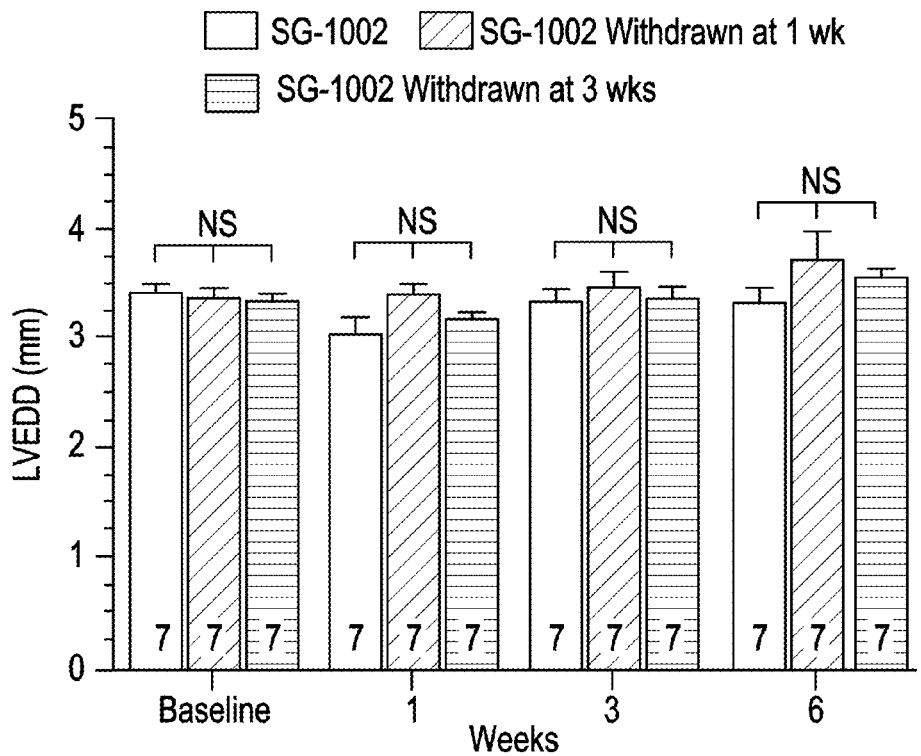
Figure 12C:
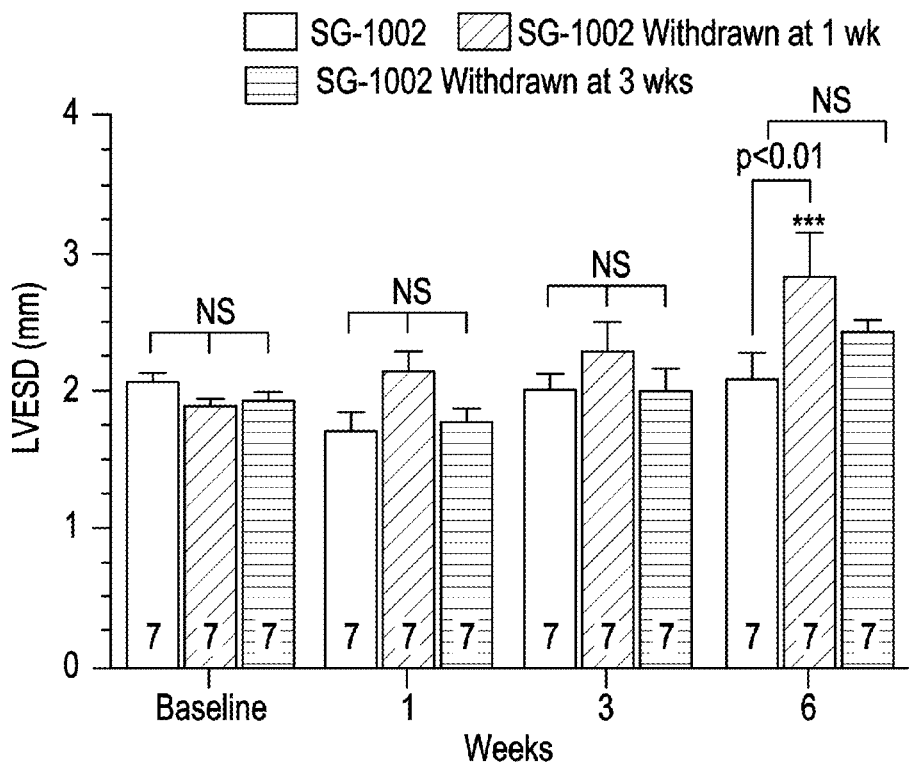
Figure 12D:
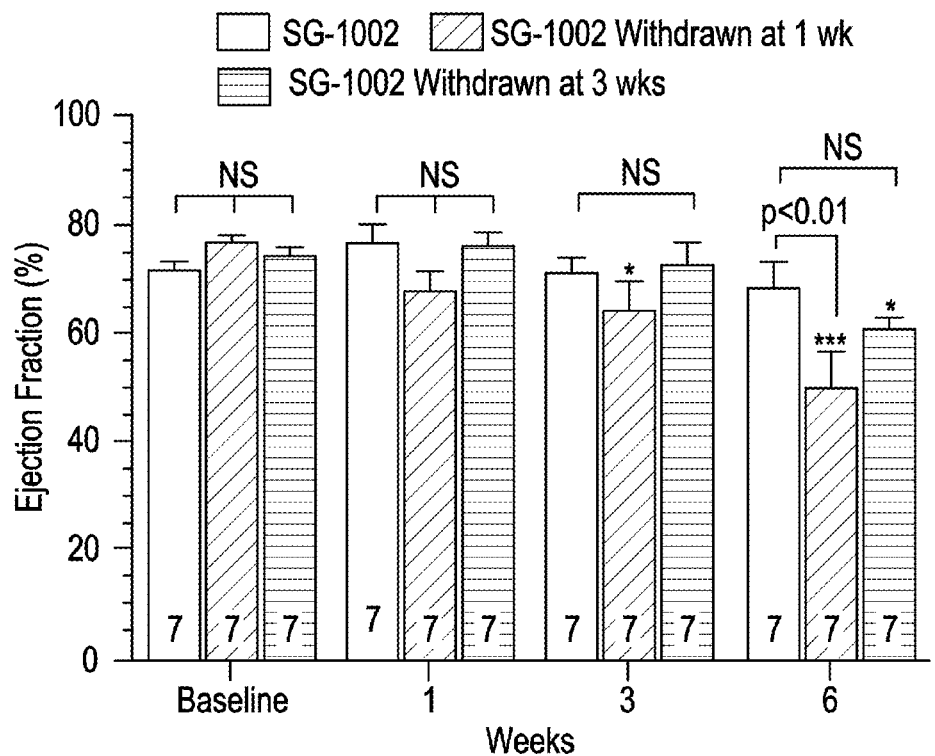

Withdrawal of SG-1002 Leads to Development of Cardiac Dilatation and Dysfunction Experiments were then conducted to determine how withdrawal of SG-1002 from the chow would affect the development of cardiac dilatation and dysfunction after TAC. For these experiments, SG-1002 was administered in the chow for 1 week and then subjected different groups of mice to 6 weeks of TAC: (1) Mice received SG-1002 in the chow for 6 weeks following TAC, (2) Mice received SG-1002 in the chow for 1 week following TAC and then received normal chow for 5 weeks; (3) Mice received SG-1002 in the chow for 3 weeks following TAC and then received normal chow for 3 weeks. Echocardiography analysis revealed that all three groups of mice displayed similar degrees of increased IVSd thickness, as well as similar LVEDD diameters from 1 week to 6 weeks following TAC (FIGS. 12A-12B). Withdrawal of SG-1002 after 1 week of TAC resulted in a larger increase in LVESD and a larger decrease in ejection fraction at 6 weeks of TAC when compared to the non-withdrawal group (FIGS. 12C-12D; $p<0.01$ vs. SG-1002). Withdrawing SG-1002 at 3 weeks of TAC resulted in a non-significant increase in both of these parameters at 6 weeks of TAC when compared to the non-withdrawal group. These data indicate that the withdrawal of SG-1002 early following the onset of pressure-overload does not prevent the development of cardiac dilatation and dysfunction, suggesting that the benefits of SG-1002 are achieved when the diet is maintained throughout the follow-up period.

Example 6

$H_2S$ Therapy Augments VEGF-Akt-eNOS-Nitric Oxide Signaling Following TAC

Figure 6A:
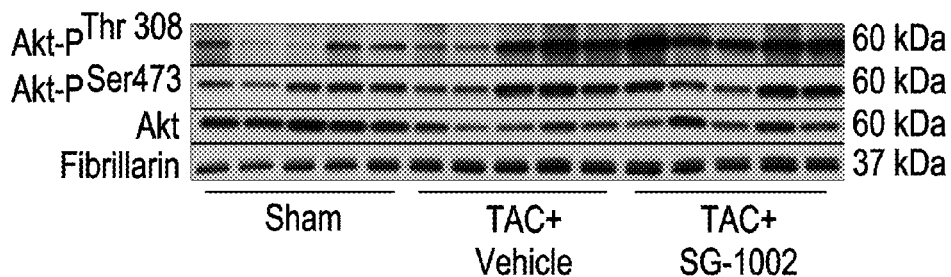
FIGS. 6A-6H are data showing $H_2S$ upregulates Akt phosphorylation, VEGF expression, and activates the eNOS-NO pathway following TAC.
Figure 6B:
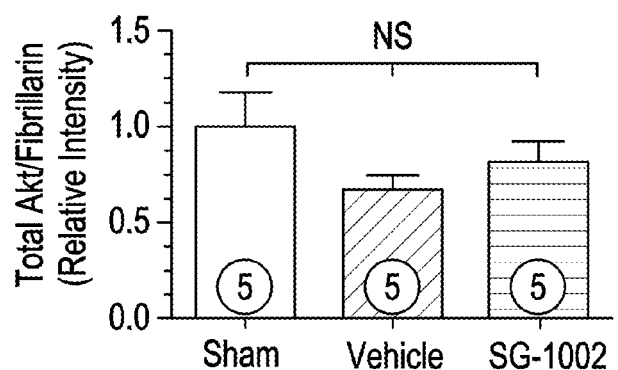
Figure 6C:
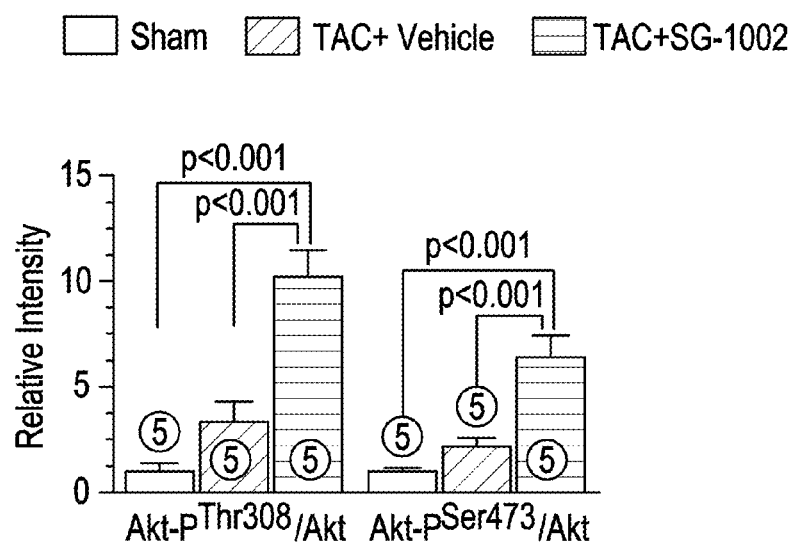
Figure 6D:
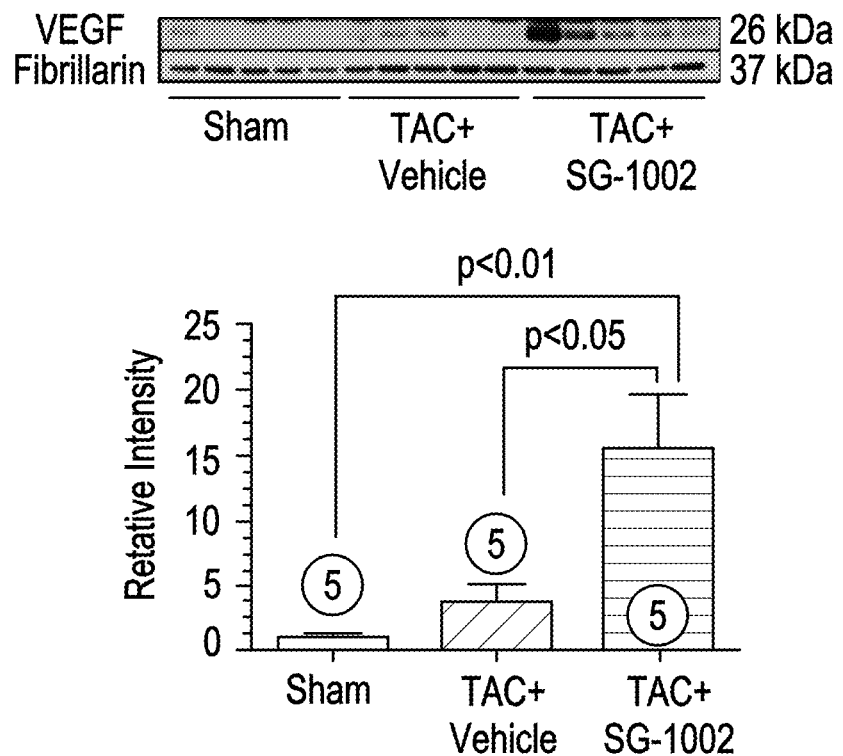
Figure 6E:
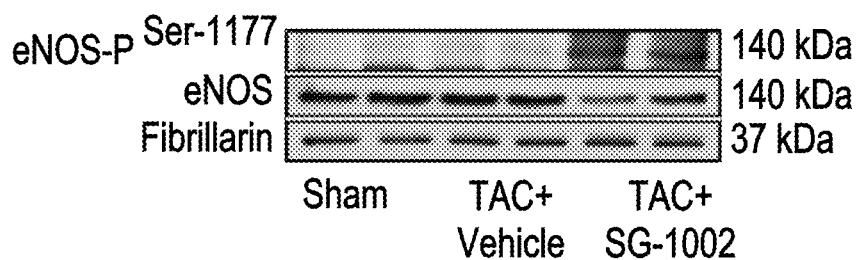
Figure 6F:
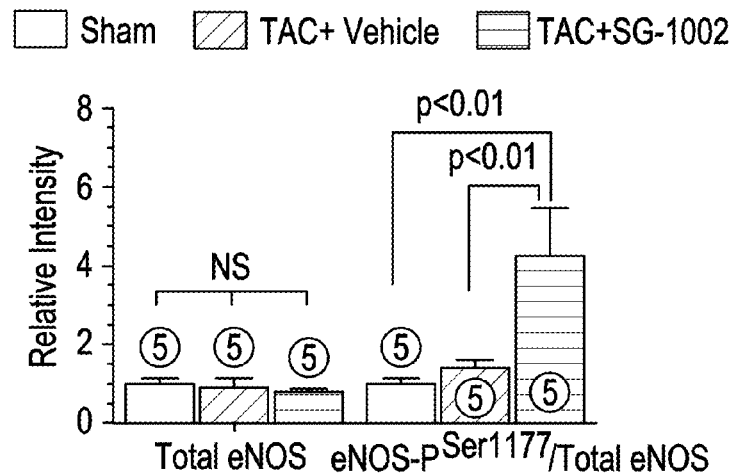
Figure 6G:
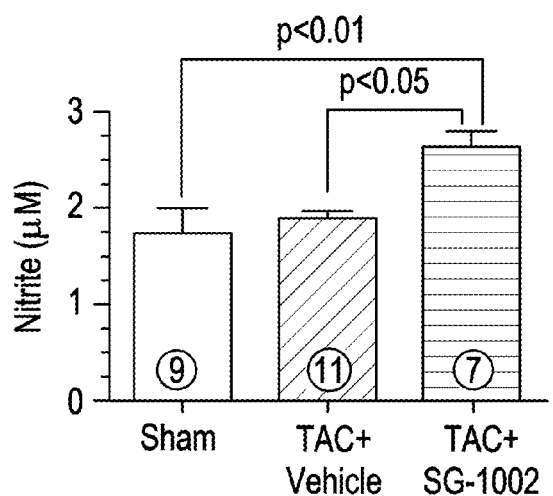
Figure 6H:
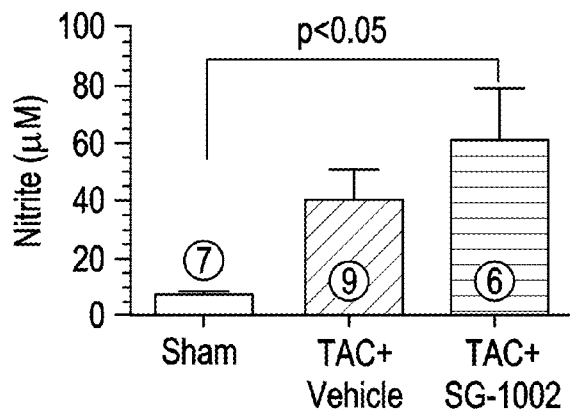

The serine/threonine kinase Akt regulates cardiac growth, myocardial angiogenesis, and survival in cardiac myocytes. SG-1002 treatment was examined to see whether activation Akt phosphorylation was activated in the heart following TAC. Representative Western blots for Akt phosphorylation status in the heart at 6 weeks following TAC are shown in FIG. 6A. SG-1002 treatment did not alter total Akt expression in the heart (FIG. 6B) but did significantly increase the expression of phosphorylated Akt at threonine residue 308 (Akt-$P^{Thr308}$) ($p<0.001$) and serine residue 473 (Akt-$P^{Ser473}$) when compared to vehicle mice (FIG. 6e; $p<0.001$). Next, SG-1002 treatment was examined to determine if VEGF, a potent angiogenic and cytoprotective cytokine in the myocardium was upregulated. At 6 weeks following TAC, SG-1002 treated mice showed significantly greater VEGF protein expression levels in the heart (FIG. 6D; $p<0.01$ vs. Sham and $p<0.05$ vs. TAC+Vehicle), but not in the systemic circulation (FIG. 13A).

Nitric oxide (NO) generated from endothelial nitric oxide synthase (eNOS) is known to promote vascular and myocardial cell cytoprotection during ischemic conditions. To investigate the potential involvement of eNOS in SG-1002 induced cardioprotection following TAC, the expression and the phosphorylation status of eNOS at serine residue 1177 (eNOS-$P^{Ser1177}$) were assessed by Western blot analysis in the hearts of Sham, vehicle, and SG-1002 treated mice.

There were no differences in total eNOS expression in the heart among all groups (FIGS. 6 E-6F). However, the eNOS activation site (eNOS—$P^{Ser1177}$) exhibited significantly greater phosphorylation following SG-1002 when compared to Sham and TAC+Vehicle mice (FIGS. 6E-6F; $p<0.01$). Furthermore, SG-1002 treatment increased cardiac NOx (nitrite and nitrate) levels, following TAC compared to Sham mice (FIG. 6 G-H; $p<0.05$), which is indicative of increased NO bioavailability following $H_2S$ therapy. Myocardial expression of both nNOS and iNOS in mice subjected to TAC that received either vehicle or SG-1002 (FIGS. 13B-13D) was also investigated. nNOS expression in the both vehicle and SG-1002 treated mice trended to be higher than the Sham, but did not reach statistical significance. Interestingly, iNOS expression in the TAC+Vehicle group was upregulated compared to the Sham group ($p<0.01$), but SG-1002 mice diminished this upregulation ($p<0.01$ vs. TAC+Vehicle).

Example 7

Figure 7A:
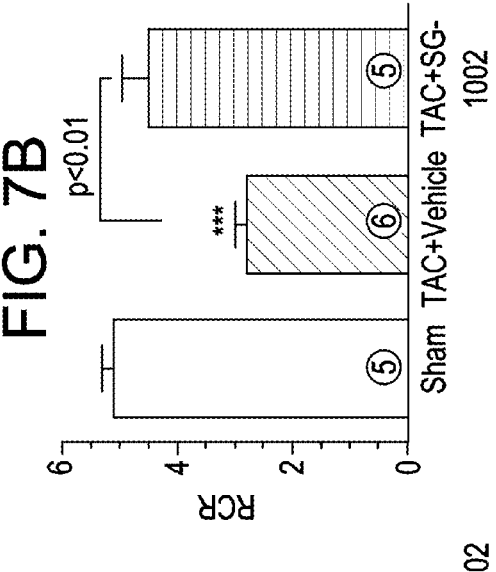
FIGS. 7A-7F are data showing H2S preserves mitochondrial respiratory function and attenuates oxidative stress following TAC.
Figure 7B:
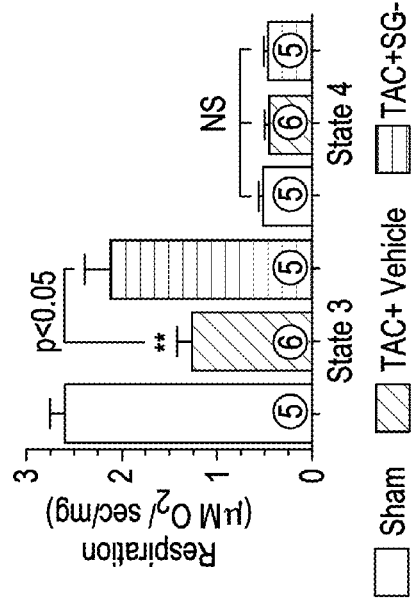

$H_2S$ Therapy Attenuates Mitochondrial Respiratory Dysfunction and Oxidative Stress Following TAC Mitochondrial energetic failure is considered one of the central pathological mechanisms in heart failure resulting from cardiac hypertrophy. Therefore, respiratory function of isolated mitochondria obtained from mouse hearts at 6 weeks following TAC was investigated. A significant decrease in State 3 respiration rates (FIG. 7A; $p<0.01$) and RCR (FIG. 7B; $p<0.001$) was observed in the TAC+Vehicle mice compared to the Sham mice. However, SG-1002 treatment preserved mitochondrial respiratory function when compared to TAC+Vehicle mice ($p<0.05$ for State 3 and $p<0.01$ for RCR). No difference in State 4 respiration was observed among any of the study groups (FIG. 7A).

Figure 7C:
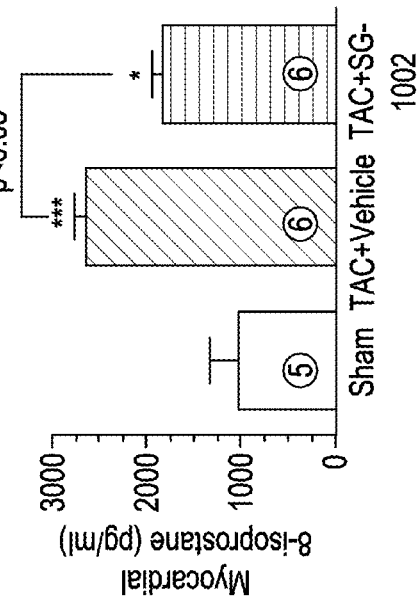
Figure 7D:
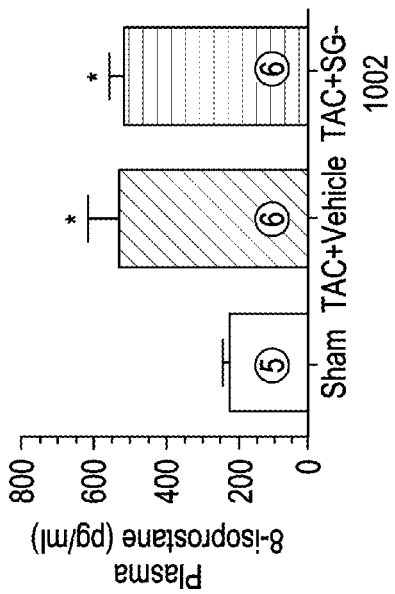
Figure 7E:
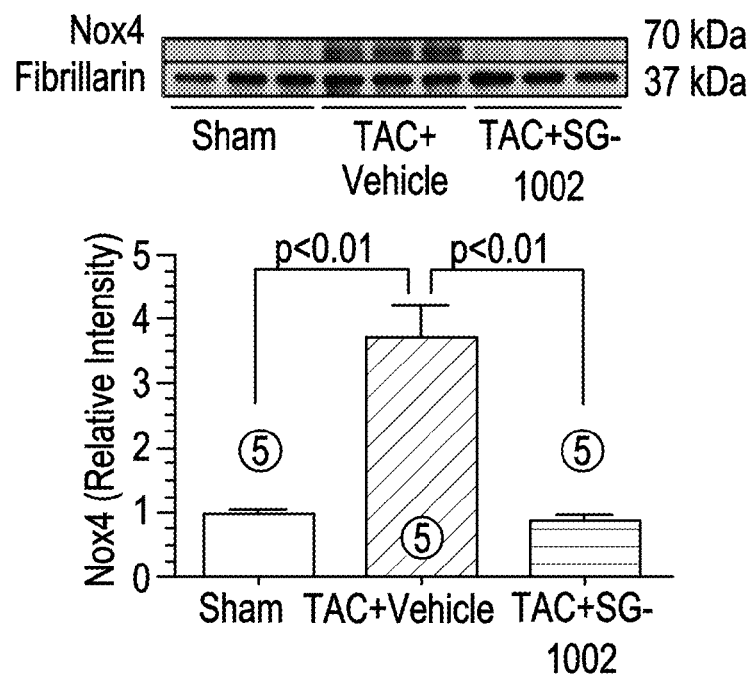
Figure 7F:
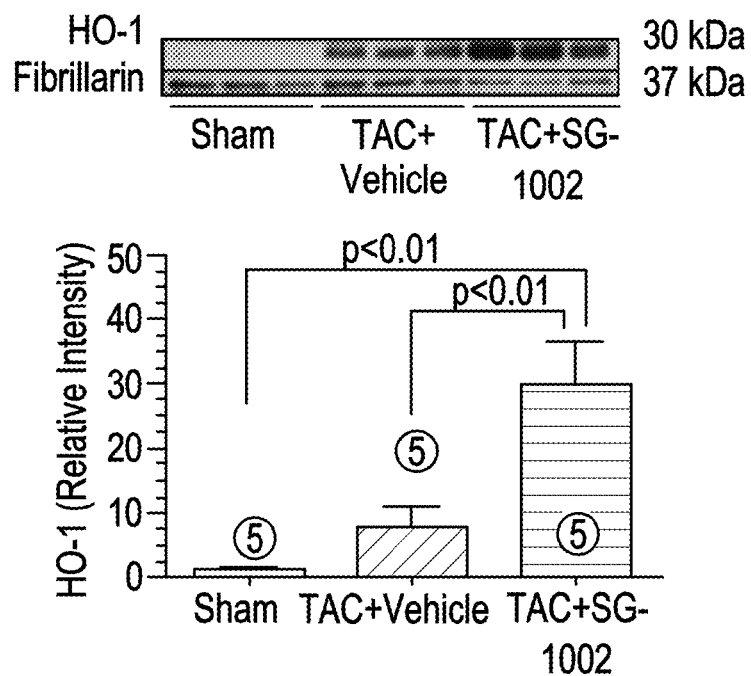

Mitochondrial dysfunction leads to impaired ATP production and increased reactive oxygen species (ROS) generation that can result in increased apoptosis. Therefore, 8-isoprostane levels were examined as a marker of antioxidant deficiency and oxidative stress in both the plasma and heart at 6 weeks following TAC. Both the TAC+Vehicle and TAC+SG-1002 treated mice exhibited higher plasma levels of 8-isoprostane compared to sham mice (FIG. 7C; $p<0.05$). However, TAC+Vehicle mice exhibited significantly higher 8-isoprostane levels in the heart compared to sham mice ($p<0.001$), whereas the administration of SG-1002 attenuated the TAC-induced increase in 8-isoprostane levels (FIG. 7D; $p<0.05$ vs. TAC+Vehicle). Next, cardiac Nox4 expression was assessed as another marker of oxidative stress. At 6 weeks following TAC, myocardial NADPH oxidase 4 (Nox4) expression was significantly upregulated in the TAC+Vehicle mice compared to Sham mice (FIG. 7E; $p<0.01$). However, SG-1002 treatment significantly inhibited the upregulation of Nox4 ($p<0.01$ vs. TAC+Vehicle). Additional analysis revealed that SG-1002 treatment resulted in an upregulation in the expression of the antioxidant heme oxygenase 1 (HO1) in the heart following TAC (FIG. 7F; $p<0.01$ vs. Sham and TAC+Vehicle).

The examples described in examples 1-7 provide several lines of evidence to support the idea that sulfide levels may be an important predictor of heart failure severity. First, in agreement with previous clinical studies, further evidence is provided showing that circulating levels of sulfide are lower in heart failure patients. Second, data is provided showing that this is mirrored in an experimental model of pressure overload-induced heart failure, as evidenced by the finding that both myocardial and circulating levels of free $H_2S$ and sulfane sulfur are significantly reduced after TAC. Third, it is demonstrated that a deficiency in endogenously produced $H_2S$ results in an exacerbation of cardiac dysfunction following TAC, whereas genetic overexpression of CSE significantly preserved left ventricular function. Finally, chronic administration of a $nH_2S$ donor provides protection against the adverse remodeling associated with TAC by increasing circulating and cardiac sulfide levels. While the mechanisms responsible for the heart failure-induced decline in sulfide levels are currently not known, this finding strongly suggests that a deficiency of $H_2S$ may contribute to the pathophysiology and progression of heart failure. These findings also suggest that increasing the bioavailability of $H_2S$ with oral $H_2S$ donor therapy significantly preserves cardiac function in the setting of heart failure.

One of the main findings of the current study is that administration of SG-1002 significantly preserved cardiac function following TAC. Given that $H_2S$ is a physiological gas that freely diffuses into multiple intracellular compartments independently of specific receptors, it can be postulated that $H_2S$ targets multiple pathological cascades simultaneously. One potential target is VEGF, which is among the most potent angiogenic and cytoprotective cytokines. Givvimani et al., *J. Appl. Physiol.* 110:1093-1100, 2011 previously reported that sodium hydrogen sulfide (NaHS) in the drinking water augmented angiogenesis via increasing VEGF expression and inhibition of antiangiogenic factors (angiostatin and endostatin). Short-term Akt activation in inducible transgenic mice induces physiological hypertrophy with maintained vascular density, whereas deficiency in Akt results in exacerbated cardiac dysfunction due to lack of exercise-induced cardiac hypertrophy. In this study, SG-1002 treatment was demonstrated to activate a VEGF-Akt-eNOS-NO signaling pathway at 6 weeks following the induction of TAC (a time point when cardiac hypertrophy and left ventricular dysfunction are significant).

An increase in oxidative stress and/or a deficiency in the endogenous antioxidant reserve can also cause contractile dysfunction. The cardioprotective effects of $H_2S$ against myocardial I/R are mediated by antioxidant signaling. In addition, $H_2S$ directly scavenges reactive oxygen species (ROS) in vitro. Therefore, endogenous $H_2S$ may directly and/or indirectly contribute to modulation of oxidative stress in the setting of pressure overload-induced hypertrophy. Here, it was demonstrated that $H_2S$ attenuates the TAC-induced increase in oxidative stress, as evidenced by the finding that SG-1002 decreases cardiac 8-isoprostane levels. In terms of mechanism, it was determined that SG-1002 attenuates the TAC-induced upregulation of Nox4, a member of the NADPH oxidase family that is a major source of ROS-related cardiac dysfunction in the setting of pressure overload. It was also determined that SG-1002 upregulated the expression of HO-1 and preserved mitochondrial respiratory function. Since, mitochondrial respiratory dysfunction in the heart leads to metabolic remodeling, deficit cardiac energetics, and increased oxidative stress, the preserved mitochondrial respiratory function observed in the current study could be an additional mechanism to explain the inhibition of oxidative stress by $H_2S$ following TAC.

It has been generally thought that $H_2S$ and NO exert their biological effects via independent signaling pathways. Recent experimental evidence suggests that there is crosstalk between the $H_2S$ and NO signaling pathways, which could provide synergistic and additional regulatory effects. For example, H$_2$S upregulates NO production in endothelial cells through the activation of eNOS in an Akt-dependent manner. Likewise, NO has been shown to enhance the production of H$_2$S from vascular tissue and more recently, Coletta et al., Proc. Natl. Acad. Sci. USA. 109:9161-9166, 2012, demonstrated that NO and H$_2$S are mutually required for the control of vascular function. Therefore, another major finding of the current study is the evidence that exogenous H$_2$S therapy very potently activates eNOS and increases NO bioavailability within the myocardium. This is important for two reasons: (1) it further corroborates the evidence that there is crosstalk between the H$_2$S and NO systems and (2) provides evidence for the first time that H$_2$S increases the bioavailability of NO in an in vivo model of disease. Consequently the activation of eNOS by SG-1002 may serve as an important mechanism for the observed protective effects against TAC. In terms of its effects on hypertrophy, NO produced from eNOS has been shown to have antihypertrophic effects in the heart as evidenced by the findings that eNOS KO mice have hypertension and cardiac hypertrophy and exhibit exacerbated cardiac dysfunction due to pressure overload induced hypertrophy compared to WT mice. Moreover, cardiac specific overexpression of eNOS prevents isoproterenol induced cardiac hypertrophy. However, in sharp contrast, Takimoto et al., J. Clin. Invest. 115:1221-1231, 2011 suggested that pressure overload results in eNOS-uncoupling resulting in increased myocardial oxidant production and exacerbated cardiac function. In spite of this, physicians have been successfully using drugs which are able to activate eNOS, (i.e. ACE-1, ARB, and β-blockers) in the treatment of heart failure. Therefore, controversy still remains in regards to the utility and effectiveness of NO-based therapies in the treatment of heart failure, which warrants further investigation to resolve these issues. Additionally, both NO and H$_2$S are known to increase HO-1 levels, an enzyme that produces carbon monoxide (CO). This suggests that the activation of one of the endogenously produced gases can lead to the activation of the other two. Under these conditions, the three gases have the ability to synergize to produce antiapoptotic, antioxidant, anti-inflammatory, and antihypertrophic effects, which ultimately can lead to cardioprotection.

Figure 14:
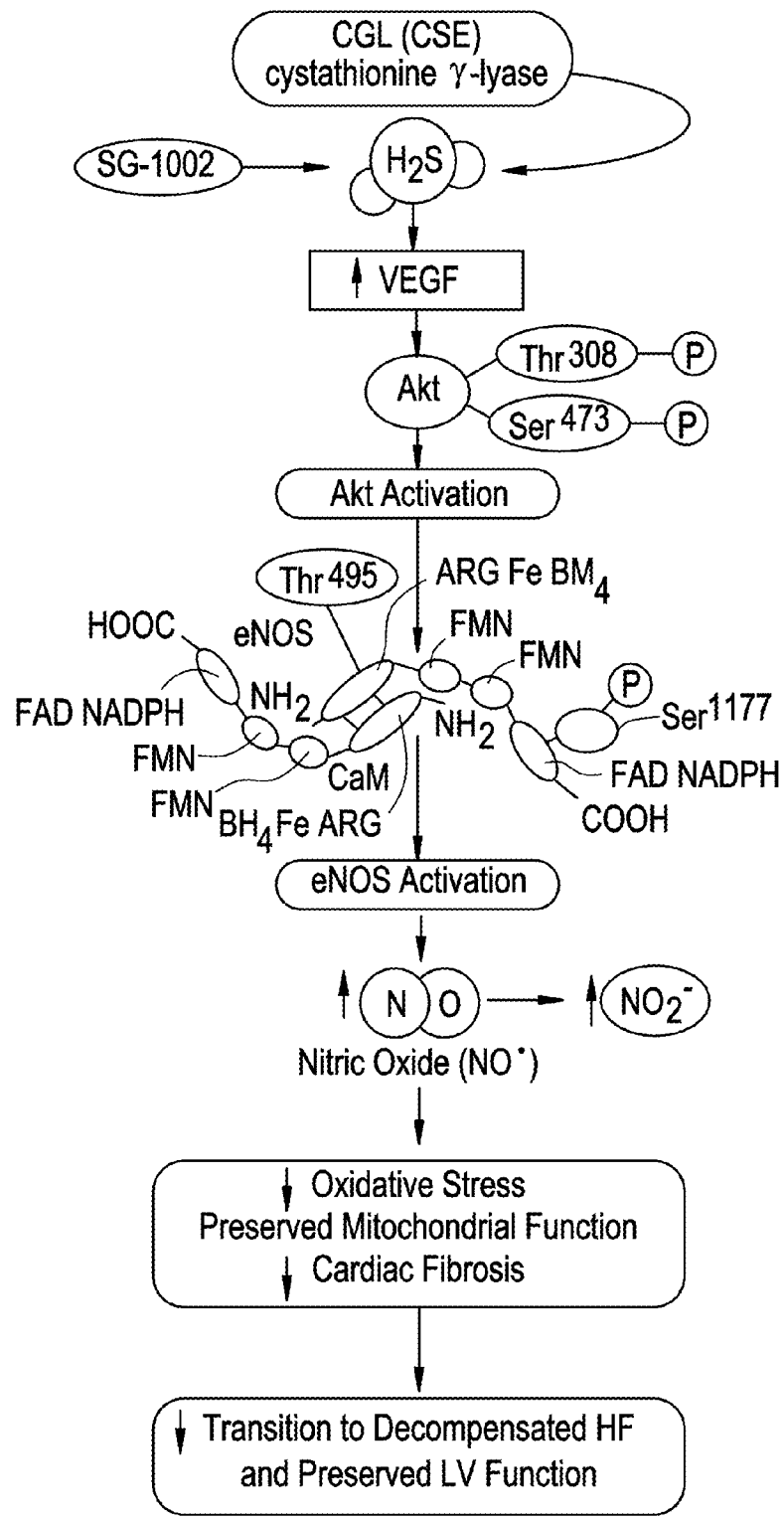
FIG. 14 is a schematic diagram highlighting the proposed mechanism by which cystathionine gamma lyase (CSE) or exogenous hydrogen sulfide protects the heart following transverse aortic constriction (TAC). Our data suggest (CSE) or hydrogen suflide donor therapy with SG-1002 activates vascular endothelial growth factor (VEGF) and subsequently phosphorylates Akt. Akt activation results in phosphorylation and activation of eNOS. Following eNOS activation nitric oxide (NO) bioavailability and nitrite levels are increased. These molecular signals result in reduced myocardial oxidative stress and injury, improvements in mitochondrial respiration, and decreased cardiac fibrosis. Ultimately, these cytoprotective actions prevent the transition from compensated to decompensated heart failure and left ventricular (LV) ejection fraction is preserved.

The findings of the current study indicate that preserving sulfide levels during the development of pressure overload-induced heart failure preserves cardiac function and prevents the transition from compensated to decompensated cardiac hypertrophy. Furthermore, the current study indicates that administration of a novel oral H$_2$S donor facilitates these protective effects by activating a VEGF-Akt-eNOS-NO signaling pathway significantly increasing NO bioavailability (FIG. 14). This cardioprotective signaling cascade ultimately results in the inhibition of oxidative stress, attenuated cardiac fibrosis, preservation of mitochondrial respiration, and preserved left ventricular function. The study suggests that endogenously produced H$_2$S plays an important role in the preservation of cardiac function in heart failure and that oral H$_2$S therapy may be a therapeutic option for the treatment of LV dysfunction in the setting of pressure overload-induced hypertrophy.

Example 8

Treatment with a Highly Bioavailable Zerovalent Sulfur-Rich Composition (SG-1002, Containing about 99% Zerovalent Sulfur) Increases Sperm Concentration and Sperm Motility in Infertile Men Between July 2009 and September 2010, a total of 435 men, of which 125 (28.73%) had oligoasthenozoospermia were evaluated at the University Center for Reproductive Medicine. Seventy-two patients who agreed to enter the study were recruited; of these 18 were eliminated for various reasons (five did not present a combination of oligozoospermia and asthenozoospermia in the second semen analysis before treatment, eight had a chronic degenerative disease, three were chronic smokers, and two had taken antioxidants two months before the study). Fifty-four patients were included in the study who started treatment. Three dropped out (one mentioned "strange" smelling sweat, one referred nausea and flatulence during the first three days of ingestion of the hard gelatin capsules, each containing 400 mg of SG-1002 (5 capsules per day) and one argued that there were too many capsules to take per day). When the patients were seen at the end of the 75 days of treatment, four did not attend despite insisting by telephone.

Information from 47 patients who complied with the protocol was analyzed. Mean age of the patients was 34.23 years, with 32 years being the most frequent. Patients were divided into three groups (hydrogen sulfide prodrug, resveratrol and placebo), maintaining a similar relationship between groups. Sixteen patients were included in the resveratrol group, 16 in the hydrogen sulfide prodrug group, and 15 in the placebo group. Two evaluations were made, a baseline sample and after treatment. In each of the two evaluations, variables such as concentration, motility, and morphology in fresh semen and post-capacitation were analyzed. The baseline characteristics of the three groups were similar. The average age of patients in each group was 34.6 years for hydrogen sulfide prodrug group, 35 years for the resveratrol group, and 33.07 years for the placebo group.

Mean sperm baseline concentration was 10.84 million per milliliter, with 0.5 million per milliliter being the lowest concentration and 19.9 million per milliliter, the highest concentration. The mean concentration in the first sample was 11.02, 10.9 and 10.64 million per milliliter for the hydrogen sulfide prodrug, resveratrol, and placebo groups, respectively. As for sperm motility recorded at baseline, A+B type motility had a mean of 13.43%, 14.43%, and 8.33% for the hydrogen sulfide prodrug, resveratrol and placebo groups, respectively. The morphology recorded in sample 1 was also similar in the three groups: 31.6% for the hydrogen sulfide prodrug group, 32.06% for the resveratrol group, and 30.06% for the placebo group with no statistically significant difference. The mobile forms recovered (MFR) obtained post-sperm capacitation were 0.579, 0.40 and 0.371 million for the hydrogen sulfide prodrug, resveratrol and placebo group, respectively (Table 8).

TABLE 8

Characteristics of the first sample in the three groups

| Characteristic | Hydrogen sulfide prodrug | Resveratrol | Placebo |
|---|---|---|---|
| Sperm concentration | $11.02 \times 10^6$ | $10.9 \times 10^6$ | $10.64 \times 10^{6a,b}$ |
| Motility A + B (%) | 13.43 | 14.43 | $8.33^{a,b}$ |
| Normal morphology (%) | 31.6 | 32.06 | $30.06^{a,b}$ |
| MFR | $0.579 \times 10^6$ | $0.40 \times 10^6$ | $0.371 \times 10^{6a,b}$ |

Note:
statistical analysis was performed using $x^2$
MFR: Mobile Forms Recovery, post sperm capacitation
[a] no statistically significant differences were found between placebo and hydrogen sulfide prodrug
[b] no statistically significant differences were found between placebo and resveratrol The data obtained from the first samples of the placebo group were compared with data obtained from the hydrogen sulfide prodrug. No statistically significant differences were found between the placebo group and the hydrogen sulfide prodrug group. Samples that were collected after treatment showed different data among the groups. The sperm concentration for the hydrogen sulfide prodrug group was 17.01 vs. 11.18 million for the placebo group (p=0.038). A+B motility for the hydrogen sulfide prodrug group was 20.06% vs. 10.06% in the placebo group (p=0.037). The morphology obtained was 36.3% for the hydrogen sulfide prodrug group compared to the placebo group with 30.4% (p=0.088). The MFR post-capacitation for the hydrogen sulfide prodrug group was $1.62 \times 10^6$ vs. $0.338 \times 10^6$ in the placebo group (p=0.035) (Table 9).

TABLE 9

Characteristics of the 2$^{nd}$ sample (post-treatment) between the hydrogen sulfide prodrug and placebo group

| Characteristic | Hydrogen sulfide prodrug | Placebo | P |
|---|---|---|---|
| Sperm concentration | $17.01 \times 10^6$ | $11.18 \times 10^6$ | 0.038 |
| Motility A + B (%) | 20.06 | 10.06 | 0.037 |
| Normal morphology (%) | 36.3 | 30.4 | 0.088 |
| MFR | $1.62 \times 10^6$ | $0.338 \times 10^6$ | 0.035 |

Note:
statistical analysis was performed using $x^2$
MFR: Mobile Forms Recovery, post sperm capacitation The results of this study provide support for using therapy with antioxidants such as SG1002 (i.e., agents that act not only as free radical/reactive oxygen species scavengers but also as indirect antioxidants that induce genes to generate other small-molecule antioxidants, antioxidant enzymes and enzymes that regulate lipid metabolism) as a valid method for improving spermatogenesis in carefully selected patients. This is the first prospective, controlled, randomized, double blind clinical trial that shows that hydrogen sulfide prodrug therapy improves some seminal parameters.

An increase in sperm concentration was observed in the hydrogen sulfide prodrug group, this was the only group with a statistically significant increase. These findings demonstrate and confirm the data obtained in other studies where antioxidant therapy appears to be effective in the management of patients with oligoasthenozoospermia.

In summary, this study demonstrates that hydrogen sulfide prodrugs such as SG1002 are well tolerated by the human body, without developing significant adverse effects at the doses used and can increase the sperm count, motility, normal morphology, and MFR post-capacitation.

Example 9

Treatment with a Highly Bioavailable Zerovalent Sulfur-Rich Composition (SG-1002) in Patients with Osteosarcoma Two trials were conducted on patients diagnosed with different forms of osteosarcoma. In one study, the patient was 11 years old. The baseline condition was characterized as osteoblastic osteosarcoma of the left distal femur, presented with a pathological fracture and important tumor-related swelling and loss of function of the adjacent joint. The patient's physical examination was remarkable for the presence of a soft tissue mass and redness at the site of the primary tumor. No evidence of lung metastasis was recorded. The patient received four cycles of chemotherapy with cisplatin, doxorubicin, ifosfamide, and etoposide with no apparent clinical response. Chemotherapy was stopped before treatment with the highly bioavailable zerovalent sulfur-rich composition. The treatment regimen consisted of administration of nine hard gelatin capsules (each containing 400 mg SG-1002) per day of the highly bioavailable zerovalent sulfur-rich composition for 12 weeks. By the end of the second week, the patient began to feel better, the pain subsided and the inflammation also began to decline. The X-ray showed reduction of the limb soft tissue surrounding the tumor. At the end of the fourth week, inflammation of the extremity had fallen dramatically to almost disappearance. There was no pain and the X-ray radiograph showed signs of growth of the cortical bone. At the end of the eighth week, the inflammation had completely disappeared. The mood of the patient was excellent. There was no pain and the X-ray radiograph showed greater cohesion bone. At the end of the twelfth week, the X-ray radiograph clearly showed greater cohesion bone. The bone was consolidated with angulation, product of the original pathological fracture.

In the second study, the patient was 13 years old. The baseline condition was characterized as telangiectasis osteosarcoma of the left proximal humerus presented with a pathological fracture and important tumor-related swelling and loss of function of the left shoulder. His physical examination was remarkable for the presence of a soft tissue mass and redness at the site of the primary tumor. At the time of diagnosis, there was evidence of bilateral lung metastases. Conventional X-rays showed a cystic, lucent lesion with a soft tissue mass with periosteal reaction. The patient received six cycles of chemotherapy with cisplatin, doxorubicin, high dose methotrexate, ifosfamide, and etoposide with modest clinical response. At the end of the sixth cycle chemotherapy was stopped. The treatment regimen consisted of administration of 9 capsules per day of the highly bioavailable zerovalent sulfur-rich composition for 12 weeks. By the end of the third week, the patient began to feel better, the pain subsided and the inflammation also began to decline. By the end of the fourth week, the X-ray radiograph showed reduction of the limb soft tissue surrounding the tumor. The CAT scan showed no improvement of the pulmonary metastases although metastases no longer progressed. At the end of the eighth week, the limb inflammation had decreased, although still noticeable. The patient had no pain and the X-ray radiograph showed that the tumor had not progressed. At the end of the twelfth week, the soft tissue swelling persisted. The mood of the patient was excellent. There was no pain and the X-ray radiograph showed no progression of the cancer in the bone. The CAT scan showed no new pulmonary metastases.

Example 10

Treatment with a Highly Bioavailable Zerovalent Sulfur-Rich Composition (SG-1002) in Patients with Conditions Associated with Hydrocephalus Three trials were conducted on patients showing signs of hydrocephalus. In the first trial, the patient was 3 years old. Her baseline condition was characterized by non specific signs of hydrocephalus. An MRI showed a mass in the posterior fossa. Surgery was planned and an incomplete resection was performed. Pathology results showed an infratentorial atypical tertoid/rabdoid tumor with leptomeningeal dissemination. She was treated at that time with various cycles of chemotherapy with very modest response. Chemotherapy was suspended and the patient was placed on palliative care. A treatment regimen consisting of administration of 6 hard gelatin capsules (each containing 400 mg SG-1002) per day of the highly bioavailable zerovalent sulfur-rich composition was started for a period of 12 weeks. The patient began to show signs of improvement at the end of the second week. The sleepiness improved and by the end of the eighth week the patient was fully conscious and without clinical evidence of headache, vomiting or irritability. The patient had an important neurological recovery and at the end of the twelfth week, the patient was able to stand and walk a few steps. The radiological evidence of the tumor disappeared and the patient could walk unaided and eat normally in the next few weeks.

In the second trial, the patient was 2 years old. She was presented with insidious, non localizing signs of increased intracranial pressure with hydrocephalus. MRI showed an intraventricular mass in the lateral ventricle. Surgery was planned, a CSF shunt was placed, and an incomplete resection was performed. Pathology results showed an anaplastic tumor consistent with choroid plexus carcinoma. She was treated at that time with various cycles of chemotherapy, with very modest response. The parents decided at that time not to give their child further treatment. A treatment regimen consisting of administration of 3 hard gelatin capsules (each containing 400 mg SG-1002) per day of the highly bioavailable zerovalent sulfur-rich composition was then initiated for a period of 12 weeks. The patient began to show signs of improvement at the end of the second week. The sleepiness was improved and by the end of the eighth week the patient was fully conscious and without clinical evidence of headache, vomiting, or irritability. The patient had an important neurological recovery at the end of the twelfth week and the patient was able to stand and walk a few steps. The radiological evidence of the residual tumor decreased but did not disappear.

The third trial was conducted on a patient who was 5 years old. She presented with non specific signs of increased intracranial pressure with hydrocephalus, vomiting, headaches, somnolence, and upward gaze palsy. MRI showed an enlarged pineal heterogeneous mass with calcifications. Surgery was planned, a CSF shunt was placed, and an incomplete resection was performed. Pathology results were consistent with pinealoblastoma. She was treated at that time with various cycles of medulloblastoma type chemotherapy with initial good response but months later showed evidence of relapse. The parents of the patient decided at that time not to give their child further treatment. A treatment regimen consisting of administration of 6 hard gelatin capsules (each containing 400 mg SG-1002) per day of the highly bioavailable zerovalent sulfur-rich composition was then initiated for a period of 12 weeks. The patient began to show improvement by the third week. The sleepiness was improved and at the end of the twelfth week the patient was fully conscious and without clinical evidence of headache, vomiting, or irritability. Radiological evidence of the residual tumor decreased but did not disappear.

Example 11

Treatment of a Patient with Ependymoma with the Highly Bioavailable Zerovalent-Sulfur-Rich Composition (SG-1002)

A trial was conducted on a 6 year old patient diagnosed with supratentorial ependymoma. She was presented in bad clinical condition with signs of increased intracranial pressure with hydrocephalus, vomiting, headaches, somnolence and papilledema. MRI showed a locally invasive tumor infiltrating adjacent to the brain at the thalamic region. Pathology review slides were consistent with a diagnosis of ependymoma. She was treated at that time with incomplete surgery and different cycles of chemotherapy. No radiotherapy was accepted and the parents decided not to give their child further treatment. She began a treatment regimen of administration of six hard gelatin capsules (each containing 400 mg SG-1002) per day of the highly bioavailable zerovalent-sulfur-rich composition for 12 weeks. The patient showed improvement by the third week. The somnolence improved gradually and by the end of the twelfth week the patient had improved considerably with large decrease in headache, vomiting, and irritability. The radiological evidence of residual tumor decreased and the clinical condition improved markedly.

Example 12

Treatment of a Patient with Macrocephaly with the Highly Bioavailable Zerovalent-Sulfur-Rich Composition (SG-1002)

An 18 month old patient with evidence of macrocephaly and lethargy alternating with irritability was treated with the highly bioavailable sulfur-rich composition. MRI prior to treatment showed hydrocephalus and a tumor mass localized in the posterior fossa. Surgery was planned, a CSF shunt was placed and a partial resection was performed. Pathology results were consistent with ependymoma. Her signs of intracraneal pressure improved because of the shunt and her hemiparesis was almost resolved. No further treatment was accepted by the parents. Four months later a MRI showed that the tumor size was increasing and the patient started complaining again of headaches, somnolence, and progressive hemiparesis. Treatment regimen consisted of administration of six hard gelatin capsules (each containing 400 mg SG-1002) per day of the highly bioavailable zerovalent-sulfur-rich composition for 12 weeks. The patient showed a slight improvement by the third week. Headache and drowsiness improved but did not disappear. By the end of the twelfth week the patient felt better, had occasional headache, no vomiting, and the hemiparesis did not progress. The radiological evidence of residual tumor after $14^{th}$ weeks showed that there was no increase in the size compared to the last study.

Example 13

Treatment of a Patient with Hemiparesis with the Highly Bioavailable Zerovalent-Sulfur-Rich Composition (SG-1002)

A 5 year old patient presented initially with progressive signs of hemiparesis at the age of three was treated with the highly bioavailable zerovalent-sulfur-rich composition of the invention for 12 weeks with administration of six hard gelatin capsules (each containing 400 mg SG-1002) per day. The patient's baseline condition consisted of non specific signs of increased intracranial pressure with morning vomiting, headaches, and somnolence. MRI showed a supratentorial tumor mass with signs of hemorrage and calcifications. Surgery was planned, a CSF shunt was placed, and a partial resection was performed. Pathology results were consistent with anaplastic ependymoma. Her signs of intracraneal pressure improved because of the shunt and her hemiparesis was almost resolved. She started chemotherapy and received 12 cycles with almost complete resolution of her signs and symptoms. MRI showed improvement with no macroscopic evidence of tumor. Four months later a MRI showed regional tumor invasion and the patient started complaining again of headaches, somnolence, and progressive hemiparesis. No further treatment was accepted by the parents. Upon administration of the highly bioavailable sulfur-rich composition, the patient showed slight improvement by the third week. Headache and drowsiness improved. By the end of the twelfth week the patient felt better, had no vomiting, and the hemiparesis did not progress. Radiological evidence of the residual tumor after 14 weeks showed no increase in the size compared to the last study.

Example 14

Treatment of a Patient with Medulloblastoma with the Highly Bioavailable Zerovalent-Sulfur-Rich Composition (SG-1002)

A trial was conducted on a 14 year old patient with recurrent medulloblastoma and pelvic dissemination of his original tumor through CSF shunt. He presented initially with abdominal pain, swelling of the extremities, and urinary symptoms as well as headaches, morning nauseas, and ataxia. He started chemotherapy with modest results. Treatment of the highly bioavailable zerovalent-sulfur-rich composition was initiated for 12 weeks by administration of nine hard gelatin capsules (each containing 400 mg SG-1002) per day. The patient showed improvement by the third week. The waist circumference decreased and the urinary symptoms disappeared. Headache and ataxia improved, but did not disappear. By the end of the twelfth week the patient felt better, the abdominal/pelvic tumor had decreased significantly. The headache and ataxia was greatly improved. The radiological evidence of the meduloblastoma recurrent in the posterior fossa did not increase in size compared to previous studies.

Example 15

Treatment of a Patient with Squamous Cell Carcinoma with the Highly Bioavailable Zerovalent-Sulfur-Rich Composition (SG-1002)

A trial was conducted on a 57 year old patient with rectal bleeding and pain due to recurrent squamous cell carcinoma of the anal canal treated with surgery, chemotherapy, and radiation therapy. His condition recurred three months after his last radiation treatment and he refused further treatment. The patient was put on a treatment regimen of nine hard gelatin capsules (each containing 400 mg SG-1002) per day of the highly bioavailable zerovalent-sulfur-rich composition of the invention. The patient showed improvement in pain in 4 or 5 days after the start of the treatment regimen. By the third week, the pain was gone and the rectal bleeding had subsided. The patient decided to restart a program of salvage chemotherapy along with the treatment regimen of the highly bioavailable sulfur-rich composition.

Example 16

Treatment of a Patient with Leukemia with the Highly Bioavailable Zerovalent-Sulfur-Rich Composition (SG-1002)

A trial was conducted on a 13 year old patient diagnosed with pre-B-calla (+) acute lymphoblastic leukemia. She was in first remission and was taking medication according to protocol BFM 85. After 6 months of treatment she started taking hydrogen sulfide precursor capsules and said she felt much better and was capable of doing exercise with better tolerance. She was running, hiking during weekends, and attending school regularly. Her treatment regimen consisted of administration of six hard gelatin capsules (each containing 400 mg SG-1002) per day. The patient was able to compare how she felt before and after the intake of the precursor of hydrogen sulfide. Her physical and intellectual capacity improved. Now she can tolerate extreme exercises, such as walking cross-country and running a 5-10 km marathon. Her mood has also improved.

Example 17

Treatment of a Patient Diagnosed with Heart Failure with the Highly Bioavailable Zerovalent-Sulfur-Rich Composition (SG-1002)

A trial was conducted on a 47 year old patient diagnosed with heart failure at the age of 46 after having increasing shortness of breath after moderate activities or exercise and chest pain. After a couple of months of ignoring his symptoms he had a heart attack. He already has a coronary angioplasty. The patient did not smoke but has a family history of diabetes and high cholesterol levels. His ejection fraction was less than 40%. He started a treatment regimen of six hard gelatin capsules (each containing 400 mg SG-1002) per day of the highly bioavailable zerovalent-sulfur-rich composition. The treatment regimen lasted for four months. By the end of the second week the patient began to feel better, blood sugar levels regularized even though the patient continued use of glibenclamide every 12 hours. The breathlessness improved by the third week. By the eighth week sugar levels were stable and the use of glibenclamide was reduced to one tablet per day without impact. Shortness of breath with exercise decreased just as chest pain. At the end of the fourth month a ventricular ejection fraction study came above 40% and the patient felt better and had better tolerance for exercise.

Example 18

Treatment of a Patient with Type 2 Diabetes with the Highly Bioavailable Zerovalent-Sulfur-Rich Composition (SG-1002)

A trial was conducted on a 44 year old obese male patient with type 2 diabetes. He was diagnosed with type 2 diabetes since he was 30 years old. Since then he has been taking glibenclamide with regular sugar control. At the age of 41 he started noticing regular coughing, shortness of breath, and orthopnea. He had a heart attack at the age of 42 and his ejection fraction after that was less than 40%. He started a treatment regimen of six hard gelatin capsules (each containing 400 mg SG-1002) per day of the highly bioavailable zerovalent-sulfur-rich composition. The treatment regimen lasted for three months. By the third week the patient began to feel better, blood sugar levels regularized even though the patient continued to use glibenclamide. Lack of air began to improve by the end of the seventh week. At the end of the third month the patient only took glibenclamide in the mornings but his glycaemia was practically normal.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A composition produced by:
   a) providing a first inorganic compound comprising sulfur in the −2 oxidation state; and
   b) reacting said first inorganic compound with a second inorganic compound comprising sulfur in the +4 oxidation state at an acidic pH, wherein said reacting produces a composition comprising:
   i) 90-99% (w/w) elemental alpha sulfur and 0.01 to 10% (w/w) highly polar components; and
   ii) wherein said composition comprises at least 96% bioactive zerovalent sulfur that readily undergoes bioconversion into hydrogen sulfide.

2. The composition of claim 1, wherein said highly polar components are selected from the group consisting of sodium polythionate, potassium polythionate, ammonium polythionate, calcium polythionate, polythionic acids, sodium thiosulfate, potassium thiosulfate, ammonium thiosulfate, calcium thiosulfate, sodium sulfate, potassium sulfate, and ammonium sulfate.

3. The composition of claim 1, wherein said composition is formulated for enteral administration and said elemental alpha sulfur and said highly polar components are present together in an amount of about 400 mg.

4. The composition of claim 3, wherein said composition is in a capsule.

* * * * *